US009468511B2

(12) United States Patent
Garrigues et al.

(10) Patent No.: US 9,468,511 B2
(45) Date of Patent: Oct. 18, 2016

(54) ELECTRONIC TOOTHBRUSH WITH VIBRATION DAMPENING

(71) Applicant: Water Pik, Inc., Fort Collins, CO (US)

(72) Inventors: Jeffrey M. Garrigues, Firestone, CO (US); Harold A. Luettgen, Windsor, CO (US)

(73) Assignee: Water Pik, Inc., Fort Collins, CO (US)

( * ) Notice: Subject to any disclaimer, the term of this patent is extended or adjusted under 35 U.S.C. 154(b) by 583 days.

(21) Appl. No.: 13/833,897

(22) Filed: Mar. 15, 2013

(65) Prior Publication Data

US 2014/0259469 A1   Sep. 18, 2014

(51) Int. Cl.
*A61C 17/34* (2006.01)
*A46B 13/02* (2006.01)

(52) U.S. Cl.
CPC ........... *A61C 17/3481* (2013.01); *A46B 13/02* (2013.01); *A61C 17/34* (2013.01); *A61C 17/3409* (2013.01); *A61C 17/3418* (2013.01)

(58) Field of Classification Search
CPC .............. A61C 17/34; A61C 17/3409; A61C 17/3481; A46B 13/00; A46B 13/02
USPC ........................................................ 15/22.1
See application file for complete search history.

(56) References Cited

U.S. PATENT DOCUMENTS

| 669,402 A | 3/1901 | Rose |
|---|---|---|
| 684,951 A | 10/1901 | Rothkranz |
| 914,501 A | 3/1909 | McEachern |
| 933,718 A | 9/1909 | Mahoney |
| 958,371 A | 5/1910 | Danek |
| 1,018,927 A | 2/1912 | Sarrazin |
| 1,033,819 A | 7/1912 | McMann |
| 1,059,426 A | 4/1913 | Barnes |
| D45,199 S | 2/1914 | McDonagh et al. |
| D45,572 S | 4/1914 | Sarrazin |
| 1,128,139 A | 2/1915 | Hoffman |
| D49,472 S | 8/1916 | Dierke |
| 1,251,250 A | 12/1917 | Libby |
| 1,268,544 A | 6/1918 | Cates |
| 1,278,225 A | 9/1918 | Schamberg |
| 1,296,067 A | 3/1919 | Fuller |
| D53,453 S | 7/1919 | Lloyd |

(Continued)

FOREIGN PATENT DOCUMENTS

| CH | 435553 | 10/1967 |
|---|---|---|
| CH | 609238 | 2/1979 |

(Continued)

OTHER PUBLICATIONS

Sonex International: Brushing with the Ultima—The World's Only Dual-Frequency Ultrasonic Toothbrush, Jul. 28, 1999, published at Sonipic.com.

(Continued)

*Primary Examiner* — Michael Jennings
(74) *Attorney, Agent, or Firm* — Dorsey & Whitney LLP

(57) ABSTRACT

An electronically powered toothbrush. The toothbrush includes a brush head including a plurality of bristles, a motor, and an output shaft connected to the brush head and the motor. The output shaft is selectively rotated by the motor. The toothbrush further includes a bumper assembly connected to the output shaft and configured to conserve kinetic energy from the output shaft during rotation and reapply the kinetic energy to the output shaft.

6 Claims, 33 Drawing Sheets

(56) References Cited

U.S. PATENT DOCUMENTS

| | | |
|---|---|---|
| 1,313,490 A | 8/1919 | Larson |
| 1,337,173 A | 4/1920 | White |
| 1,355,037 A | 10/1920 | Dziuk |
| D57,327 S | 3/1921 | Gibson |
| 1,382,681 A | 6/1921 | Segal |
| 1,424,879 A | 8/1922 | Carlstedt |
| 1,440,785 A | 1/1923 | Levis |
| 1,456,535 A | 5/1923 | Cartwright |
| 1,488,214 A | 3/1924 | Mason |
| 1,494,448 A | 5/1924 | Sookne |
| 1,497,495 A | 6/1924 | Fincke |
| 1,517,320 A | 12/1924 | Stoddart |
| 1,527,853 A | 2/1925 | Ferdon |
| 1,588,785 A | 6/1926 | Van Sant |
| 1,639,880 A | 8/1927 | Butler |
| 1,657,450 A | 1/1928 | Barnes |
| 1,676,703 A | 7/1928 | Nuyts |
| 1,696,835 A | 12/1928 | Burnett |
| 1,703,642 A | 2/1929 | Sticht |
| 1,794,711 A | 3/1931 | Jacobs |
| 1,796,641 A | 3/1931 | Zimmerman et al. |
| 1,800,993 A | 4/1931 | Funk |
| 1,832,519 A | 11/1931 | Wheat et al. |
| 1,880,617 A | 10/1932 | White |
| 1,916,641 A | 7/1933 | Seeliger |
| 1,927,365 A | 9/1933 | Frolio |
| 1,943,225 A | 1/1934 | McIntyre |
| 1,992,770 A | 2/1935 | Rathbun |
| 2,016,597 A | 10/1935 | Drake |
| 2,016,644 A | 10/1935 | Luball |
| 2,042,239 A | 5/1936 | Planding |
| 2,044,863 A | 6/1936 | Sticht |
| D101,080 S | 9/1936 | Cosad |
| 2,114,947 A | 4/1938 | Warsaw |
| D113,743 S | 3/1939 | Kahn |
| D113,744 S | 3/1939 | Kahn |
| 2,158,738 A | 5/1939 | Baker et al. |
| 2,168,964 A | 8/1939 | Strasser |
| 2,206,726 A | 7/1940 | Lasater |
| 2,209,173 A | 7/1940 | Russell |
| 2,218,072 A | 10/1940 | Runnels |
| 2,226,663 A | 12/1940 | Hill et al. |
| 2,244,098 A | 6/1941 | Busick |
| 2,246,523 A | 6/1941 | Kulik |
| 2,273,717 A | 2/1942 | Millard et al. |
| 2,278,365 A | 3/1942 | Daniels |
| 2,279,355 A | 4/1942 | Wilensky |
| 2,282,700 A | 5/1942 | Bobbroff |
| 2,312,828 A | 3/1943 | Adamsson |
| D136,156 S | 8/1943 | Fuller |
| D139,532 S | 11/1944 | Trecek |
| D141,350 S | 5/1945 | Alexander et al. |
| D144,163 S | 3/1946 | Dolnick |
| 2,401,186 A | 5/1946 | Price |
| 2,405,029 A | 7/1946 | Gallanty et al. |
| D146,271 S | 1/1947 | Stavely |
| 2,414,775 A | 1/1947 | Stavely |
| 2,429,740 A | 10/1947 | Aufsesser |
| 2,450,635 A | 10/1948 | Dembenski |
| D154,598 S | 7/1949 | Gass |
| D155,668 S | 10/1949 | Zandberg et al. |
| D157,669 S | 3/1950 | Graves, Jr. |
| D160,101 S | 9/1950 | MacDonald |
| 2,533,345 A | 12/1950 | Bennett |
| 2,543,999 A | 3/1951 | Voss |
| D163,707 S | 6/1951 | Pifer |
| 2,558,332 A | 6/1951 | Artale |
| 2,567,080 A | 9/1951 | Pifer |
| 2,577,597 A | 12/1951 | Wright et al. |
| 2,583,750 A | 1/1952 | Runnels |
| 2,598,275 A | 5/1952 | Lakin |
| 2,618,003 A | 11/1952 | Robey |
| D169,131 S | 3/1953 | Fay |
| 2,651,068 A | 9/1953 | Seko |
| D170,680 S | 10/1953 | Del Mas |
| D172,693 S | 7/1954 | Wibbelsman et al. |
| D173,616 S | 12/1954 | Hernandez |
| 2,705,335 A | 4/1955 | Glassman et al. |
| 2,709,227 A | 5/1955 | Foley et al. |
| 2,722,703 A | 11/1955 | Green |
| 2,728,928 A | 1/1956 | Beeren |
| 2,734,139 A | 2/1956 | Murphy |
| 2,806,235 A | 9/1957 | Carstairs et al. |
| 2,819,482 A | 1/1958 | Applegate |
| 2,868,215 A | 1/1959 | Mechem |
| 2,875,458 A | 3/1959 | Tsuda |
| 2,917,758 A | 12/1959 | Held et al. |
| 2,931,371 A | 4/1960 | Petitta |
| 2,946,072 A | 7/1960 | Filler et al. |
| 2,962,033 A | 11/1960 | Lew |
| 2,977,614 A | 4/1961 | Demanuele |
| 2,977,682 A | 4/1961 | Flatray |
| 3,103,027 A | 9/1963 | Birch |
| 3,104,405 A | 9/1963 | Perrinjaquet |
| 3,106,216 A | 10/1963 | Kirby |
| D197,048 S | 12/1963 | Troy |
| D197,208 S | 12/1963 | Cassidy et al. |
| 3,143,697 A | 8/1964 | Springer |
| 3,145,404 A | 8/1964 | Fiedler |
| D199,560 S | 11/1964 | Thompson |
| D199,893 S | 12/1964 | Bond et al. |
| 3,159,859 A | 12/1964 | Rasmussen |
| 3,160,902 A | 12/1964 | Aymar |
| 3,168,834 A | 2/1965 | Smithson |
| 3,181,189 A | 5/1965 | Leyden |
| 3,183,538 A | 5/1965 | Hubner |
| 3,195,537 A | 7/1965 | Blasi |
| D202,873 S | 11/1965 | Husted |
| 3,220,039 A | 11/1965 | Dayton et al. |
| 3,229,318 A | 1/1966 | Clemens |
| 3,230,562 A | 1/1966 | Birch |
| D204,127 S | 3/1966 | Syvertson |
| 3,258,805 A | 7/1966 | Rossnan |
| 3,270,416 A | 9/1966 | Massa |
| 3,278,963 A | 10/1966 | Bond |
| 3,289,681 A | 12/1966 | Chambers |
| 3,311,116 A | 3/1967 | Foster |
| 3,316,576 A | 5/1967 | Urbrush |
| 3,335,443 A | 8/1967 | Parisi et al. |
| 3,346,748 A | 10/1967 | McNair |
| 3,358,309 A | 12/1967 | Richardson |
| 3,358,314 A | 12/1967 | Matibag |
| 3,359,588 A | 12/1967 | Kobler |
| 3,364,576 A | 1/1968 | Kern, Jr. |
| D210,066 S | 2/1968 | Johnson |
| 3,369,265 A | 2/1968 | Halberstadt et al. |
| 3,371,260 A | 2/1968 | Jackson et al. |
| D210,349 S | 3/1968 | Boldt |
| 3,375,820 A | 4/1968 | Kuris et al. |
| D212,208 S | 9/1968 | Rogers |
| 3,418,552 A | 12/1968 | Holmes |
| 3,421,524 A | 1/1969 | Waters |
| 3,430,279 A | 3/1969 | Hintze |
| 3,463,994 A | 8/1969 | Spohr |
| 3,466,689 A | 9/1969 | Aurelio et al. |
| 3,472,045 A | 10/1969 | Nelsen et al. |
| 3,472,247 A | 10/1969 | Borsum et al. |
| 3,474,799 A | 10/1969 | Cappello |
| 3,509,874 A | 5/1970 | Stillman |
| 3,535,726 A | 10/1970 | Sawyer |
| 3,536,065 A | 10/1970 | Moret |
| 3,538,359 A | 11/1970 | Barowski |
| 3,552,022 A | 1/1971 | Axelsson |
| 3,559,292 A | 2/1971 | Weissman |
| 3,563,233 A | 2/1971 | Bodine |
| 3,588,936 A | 6/1971 | Duve |
| 3,590,814 A | 7/1971 | Bennett et al. |
| D221,823 S | 9/1971 | Cook |
| 3,608,548 A | 9/1971 | Lewis |
| 3,642,344 A | 2/1972 | Corker |
| 3,651,576 A | 3/1972 | Massa |
| 3,660,902 A | 5/1972 | Axelsson |
| 3,667,483 A | 6/1972 | McCabe |
| 3,672,378 A | 6/1972 | Silverman |

(56) References Cited

U.S. PATENT DOCUMENTS

| | | |
|---|---|---|
| 3,676,218 A | 7/1972 | Sawyer |
| 3,685,080 A | 8/1972 | Hubner |
| 3,722,020 A | 3/1973 | Hills |
| 3,742,549 A | 7/1973 | Scopp et al. |
| 3,759,274 A | 9/1973 | Warner |
| 3,760,799 A | 9/1973 | Crowson |
| 3,792,504 A | 2/1974 | Smith |
| 3,809,977 A | 5/1974 | Balamuth et al. |
| 3,831,611 A | 8/1974 | Hendricks |
| 3,840,932 A | 10/1974 | Balamuth et al. |
| 3,847,167 A | 11/1974 | Brien |
| 3,851,984 A | 12/1974 | Crippa |
| D234,518 S | 3/1975 | Gerlich |
| 3,882,364 A | 5/1975 | Wright et al. |
| 3,902,510 A | 9/1975 | Roth |
| 3,903,601 A | 9/1975 | Anderson et al. |
| 3,939,599 A | 2/1976 | Henry et al. |
| 3,967,617 A | 7/1976 | Krolik |
| 3,973,558 A | 8/1976 | Stouffer et al. |
| 3,978,852 A | 9/1976 | Annoni |
| 3,980,906 A | 9/1976 | Kuris et al. |
| 4,004,344 A | 1/1977 | Gold et al. |
| 4,005,722 A | 2/1977 | Bragg |
| 4,008,728 A | 2/1977 | Sanchez |
| 4,010,509 A | 3/1977 | Huish |
| 4,014,354 A | 3/1977 | Garrett |
| 4,019,522 A | 4/1977 | Elbreder |
| 4,033,008 A | 7/1977 | Warren et al. |
| 4,048,723 A | 9/1977 | Thorup |
| 4,051,571 A | 10/1977 | Ayers |
| 4,064,883 A | 12/1977 | Oldham |
| 4,133,339 A | 1/1979 | Naslund |
| 4,141,352 A | 2/1979 | Ebner et al. |
| 4,156,620 A | 5/1979 | Clemens |
| 4,177,434 A | 12/1979 | Ida |
| D254,162 S | 2/1980 | Barker |
| 4,192,035 A | 3/1980 | Kuris |
| 4,203,431 A | 5/1980 | Abura et al. |
| 4,205,664 A | 6/1980 | Baccialon |
| 4,219,619 A | 8/1980 | Zarow |
| 4,235,253 A | 11/1980 | Moore |
| 4,245,658 A | 1/1981 | Lecouturier |
| RE30,536 E | 3/1981 | Perdreaux, Jr. |
| 4,255,693 A | 3/1981 | Keidl |
| 4,265,257 A | 5/1981 | Salyer |
| 4,268,933 A | 5/1981 | Papas |
| 4,271,382 A | 6/1981 | Maeda et al. |
| 4,271,384 A | 6/1981 | Beiling et al. |
| 4,271,854 A | 6/1981 | Bengtsson |
| 4,275,363 A | 6/1981 | Mishiro et al. |
| 4,288,883 A | 9/1981 | Dolinsky |
| 4,289,486 A | 9/1981 | Sargeant |
| 4,303,064 A | 12/1981 | Buffa |
| 4,307,740 A | 12/1981 | Florindez et al. |
| 4,319,377 A | 3/1982 | Tarrson et al. |
| 4,319,595 A | 3/1982 | Ulrich |
| 4,326,547 A | 4/1982 | Verplank |
| 4,326,548 A | 4/1982 | Wagner |
| 4,326,549 A | 4/1982 | Hinding |
| 4,331,422 A | 5/1982 | Heyman |
| 4,333,197 A | 6/1982 | Kuris |
| 4,336,622 A | 6/1982 | Teague, Jr. et al. |
| D265,515 S | 7/1982 | Levine |
| 4,338,957 A | 7/1982 | Meibauer |
| D265,698 S | 8/1982 | Roth |
| 4,346,492 A | 8/1982 | Solow |
| 4,347,839 A | 9/1982 | Youngclaus, Jr. |
| 4,353,141 A | 10/1982 | Teague, Jr. et al. |
| 4,356,585 A | 11/1982 | Protell et al. |
| 4,381,478 A | 4/1983 | Saijo et al. |
| 4,395,665 A | 7/1983 | Buchas |
| 4,397,327 A | 8/1983 | Hadary |
| D270,972 S | 10/1983 | Rosofsky |
| D272,565 S | 2/1984 | Levine |
| D272,680 S | 2/1984 | Stocchi |
| 4,429,997 A | 2/1984 | Matthews |
| 4,432,729 A | 2/1984 | Fattaleh |
| 4,434,806 A | 3/1984 | Givens |
| 4,442,830 A | 4/1984 | Markau |
| D274,018 S | 5/1984 | Usui |
| 4,450,599 A | 5/1984 | Scheller et al. |
| 4,455,704 A | 6/1984 | Williams |
| 4,458,702 A | 7/1984 | Grollimund |
| 4,488,327 A | 12/1984 | Snider |
| 4,490,114 A | 12/1984 | Kleesattel |
| 4,505,678 A | 3/1985 | Andersson |
| 4,517,701 A | 5/1985 | Stanford, Jr. |
| 4,519,111 A | 5/1985 | Cavazza |
| 4,522,355 A | 6/1985 | Moran |
| 4,522,595 A | 6/1985 | Selvidge |
| 4,543,679 A | 10/1985 | Rosofsky et al. |
| D281,202 S | 11/1985 | Thompson |
| 4,562,413 A | 12/1985 | Mishiro et al. |
| 4,564,794 A | 1/1986 | Kilen et al. |
| 4,571,768 A | 2/1986 | Kawashima |
| 4,576,190 A | 3/1986 | Youssef |
| 4,577,649 A | 3/1986 | Shimenkov |
| 4,578,033 A | 3/1986 | Mossle et al. |
| D283,374 S | 4/1986 | Cheuk-Yiu |
| 4,585,415 A | 4/1986 | Hommann |
| 4,586,521 A | 5/1986 | Urso |
| D284,236 S | 6/1986 | Collet |
| D284,528 S | 7/1986 | Jurado |
| 4,603,448 A | 8/1986 | Middleton et al. |
| 4,605,025 A | 8/1986 | McSpadden |
| 4,608,019 A | 8/1986 | Kumabe et al. |
| 4,610,043 A | 9/1986 | Vezjak |
| 4,617,695 A | 10/1986 | Amos et al. |
| 4,617,718 A | 10/1986 | Andersson |
| D287,073 S | 12/1986 | Thompson |
| 4,634,376 A | 1/1987 | Mossle et al. |
| 4,644,937 A | 2/1987 | Hommann |
| 4,655,198 A | 4/1987 | Hommann |
| 4,672,706 A | 6/1987 | Hill |
| D292,448 S | 10/1987 | Vianello |
| 4,698,869 A | 10/1987 | Mierau et al. |
| 4,706,322 A | 11/1987 | Nicolas |
| 4,706,695 A | 11/1987 | Urso |
| D294,885 S | 3/1988 | Mollenhoff |
| 4,729,142 A | 3/1988 | Yoshioka |
| D297,467 S | 8/1988 | McCann |
| 4,766,630 A | 8/1988 | Hegemann |
| 4,776,054 A | 10/1988 | Rauch |
| 4,787,847 A | 11/1988 | Martin et al. |
| 4,791,940 A | 12/1988 | Hirshfeld et al. |
| 4,800,608 A | 1/1989 | Key |
| 4,802,255 A | 2/1989 | Breuer et al. |
| 4,811,445 A | 3/1989 | Lagieski et al. |
| 4,820,153 A | 4/1989 | Romhild et al. |
| 4,820,154 A | 4/1989 | Romhild et al. |
| 4,827,550 A | 5/1989 | Graham et al. |
| 4,827,551 A | 5/1989 | Maser et al. |
| 4,827,552 A | 5/1989 | Bojar et al. |
| 4,832,063 A | 5/1989 | Smole |
| D301,770 S | 6/1989 | Bethany |
| 4,844,104 A | 7/1989 | Martin |
| 4,845,795 A | 7/1989 | Crawford et al. |
| 4,856,133 A | 8/1989 | Sanchez |
| 4,864,676 A | 9/1989 | Schaiper |
| D303,876 S | 10/1989 | Clemens et al. |
| 4,871,396 A | 10/1989 | Tsujita et al. |
| 4,873,496 A | 10/1989 | Ohgihara et al. |
| 4,875,265 A | 10/1989 | Yoshida |
| 4,877,934 A | 10/1989 | Spinello |
| 4,879,781 A | 11/1989 | Desimone |
| 4,880,382 A | 11/1989 | Moret et al. |
| 4,887,052 A | 12/1989 | Murakami et al. |
| 4,892,191 A | 1/1990 | Nakamara |
| 4,908,902 A | 3/1990 | McNab et al. |
| 4,913,133 A | 4/1990 | Tichy |
| 4,913,176 A | 4/1990 | DeNiro |
| 4,922,936 A | 5/1990 | Buzzi et al. |
| D308,765 S | 6/1990 | Johnson |
| 4,974,278 A | 12/1990 | Hommann |

(56) References Cited

U.S. PATENT DOCUMENTS

| | | |
|---|---|---|
| 4,984,173 A | 1/1991 | Imam et al. |
| 4,989,287 A | 2/1991 | Scherer |
| 4,991,249 A | 2/1991 | Suroff |
| 4,995,403 A | 2/1991 | Beckman et al. |
| 5,000,684 A | 3/1991 | Odrich |
| 5,002,487 A | 3/1991 | Tichy |
| 5,007,127 A | 4/1991 | Paolo |
| 5,016,660 A | 5/1991 | Boggs |
| 5,020,179 A | 6/1991 | Scherer |
| 5,033,150 A | 7/1991 | Gross et al. |
| D318,918 S | 8/1991 | Hartwein |
| D319,363 S | 8/1991 | Uemura et al. |
| 5,046,212 A | 9/1991 | O'Conke |
| 5,050,625 A | 9/1991 | Siekmann |
| 5,054,149 A | 10/1991 | Si-Hoe et al. |
| D321,285 S | 11/1991 | Hirabayashi |
| 5,062,797 A | 11/1991 | Gonser |
| 5,067,223 A | 11/1991 | Bruno |
| D321,986 S | 12/1991 | Snyder et al. |
| 5,068,939 A | 12/1991 | Holland |
| 5,069,233 A | 12/1991 | Ritter |
| 5,069,621 A | 12/1991 | Paradis |
| 5,071,348 A | 12/1991 | Woog |
| 5,072,477 A | 12/1991 | Pai |
| 5,072,482 A | 12/1991 | Bojar et al. |
| 5,077,855 A | 1/1992 | Ambasz |
| 5,085,236 A | 2/1992 | Odneal et al. |
| 5,088,145 A | 2/1992 | Whitefield |
| D324,957 S | 3/1992 | Piano |
| 5,094,256 A | 3/1992 | Barth |
| 5,095,470 A | 3/1992 | Oka et al. |
| 5,100,321 A | 3/1992 | Coss et al. |
| 5,120,225 A | 6/1992 | Amit |
| 5,123,841 A | 6/1992 | Millner |
| 5,125,837 A | 6/1992 | Warrin et al. |
| 5,133,661 A | 7/1992 | Euvrard |
| 5,138,733 A | 8/1992 | Bock |
| 5,145,369 A | 9/1992 | Lustig et al. |
| 5,146,643 A | 9/1992 | Bojar et al. |
| 5,150,492 A | 9/1992 | Suroff |
| 5,151,030 A | 9/1992 | Comeaux |
| D330,116 S | 10/1992 | Crawford et al. |
| D330,286 S | 10/1992 | Curtis et al. |
| D330,458 S | 10/1992 | Curtis et al. |
| 5,152,394 A | 10/1992 | Hughes |
| 5,163,375 A | 11/1992 | Withers et al. |
| 5,165,131 A | 11/1992 | Staar |
| 5,167,193 A | 12/1992 | Withers et al. |
| 5,169,313 A | 12/1992 | Kline |
| 5,170,809 A | 12/1992 | Imai et al. |
| 5,174,314 A | 12/1992 | Charatan |
| 5,176,157 A | 1/1993 | Mazza |
| 5,177,826 A | 1/1993 | Vrignaud et al. |
| 5,180,363 A | 1/1993 | Idemoto et al. |
| D332,873 S | 2/1993 | Hall |
| 5,183,063 A | 2/1993 | Ringle et al. |
| 5,183,156 A | 2/1993 | Bruno |
| 5,184,368 A | 2/1993 | Holland |
| 5,184,632 A | 2/1993 | Gross et al. |
| 5,186,191 A | 2/1993 | Loubier |
| 5,188,133 A | 2/1993 | Romanus |
| 5,189,751 A | 3/1993 | Giuliani et al. |
| 5,193,678 A | 3/1993 | Janocik et al. |
| 5,198,732 A | 3/1993 | Morimoto |
| D334,472 S | 4/1993 | Curtis et al. |
| 5,201,092 A | 4/1993 | Colson |
| D335,579 S | 5/1993 | Chuang |
| 5,207,773 A | 5/1993 | Henderson |
| 5,213,434 A | 5/1993 | Hahn |
| 5,214,819 A | 6/1993 | Kirchner |
| 5,217,031 A | 6/1993 | Santoro |
| 5,224,500 A | 7/1993 | Stella |
| 5,226,206 A | 7/1993 | Davidovitz et al. |
| 5,236,358 A | 8/1993 | Sieffert |
| 5,245,117 A | 9/1993 | Withers et al. |
| 5,246,022 A | 9/1993 | Israel et al. |
| 5,247,716 A | 9/1993 | Bock |
| 5,253,382 A | 10/1993 | Beny |
| 5,261,430 A | 11/1993 | Mochel |
| 5,263,218 A | 11/1993 | Giuliani et al. |
| D341,943 S | 12/1993 | Si-Hoe |
| D342,160 S | 12/1993 | Curtis et al. |
| D342,161 S | 12/1993 | Curtis et al. |
| D342,162 S | 12/1993 | Curtis et al. |
| 5,267,579 A | 12/1993 | Bushberger |
| D343,064 S | 1/1994 | Reno |
| 5,279,314 A | 1/1994 | Poulos et al. |
| 5,289,604 A | 3/1994 | Kressner |
| 5,293,886 A | 3/1994 | Czapor |
| 5,294,896 A | 3/1994 | Kjellander et al. |
| D346,212 S | 4/1994 | Hosl |
| 5,299,723 A | 4/1994 | Hempel |
| 5,305,492 A | 4/1994 | Giuliani et al. |
| D346,697 S | 5/1994 | O'Conke |
| 5,309,590 A | 5/1994 | Giuliani et al. |
| 5,309,591 A | 5/1994 | Hägele et al. |
| 5,311,632 A | 5/1994 | Center |
| 5,311,633 A | 5/1994 | Herzog et al. |
| 5,315,731 A | 5/1994 | Millar |
| D347,943 S | 6/1994 | Perry |
| 5,323,796 A | 6/1994 | Urso |
| 5,335,389 A | 8/1994 | Curtis et al. |
| 5,337,435 A | 8/1994 | Krasner et al. |
| 5,339,482 A | 8/1994 | Desimone et al. |
| 5,341,534 A | 8/1994 | Serbinski et al. |
| 5,341,537 A | 8/1994 | Curtis et al. |
| 5,351,358 A | 10/1994 | Larrimore |
| 5,353,460 A | 10/1994 | Bauman |
| 5,354,246 A | 10/1994 | Gotman |
| 5,355,638 A | 10/1994 | Hoffman |
| 5,358,328 A | 10/1994 | Inoue et al. |
| D352,396 S | 11/1994 | Curtis et al. |
| D352,829 S | 11/1994 | Perry |
| 5,359,747 A | 11/1994 | Amakasu |
| 5,365,627 A | 11/1994 | Jousson et al. |
| D353,490 S | 12/1994 | Hartwein |
| 5,369,831 A | 12/1994 | Bock |
| 5,371,915 A | 12/1994 | Key |
| 5,373,602 A | 12/1994 | Bang |
| D354,168 S | 1/1995 | Hartwein |
| 5,378,153 A | 1/1995 | Giuliani et al. |
| 5,383,242 A | 1/1995 | Bigler et al. |
| 5,392,483 A | 2/1995 | Heinzelman et al. |
| 5,393,229 A | 2/1995 | Ram |
| 5,396,678 A | 3/1995 | Bredall et al. |
| 5,398,368 A | 3/1995 | Elder |
| 5,400,811 A | 3/1995 | Meibauer |
| 5,404,608 A | 4/1995 | Hommann |
| 5,406,664 A | 4/1995 | Hukuba |
| 5,406,965 A | 4/1995 | Levine |
| D358,486 S | 5/1995 | Loew |
| D358,713 S | 5/1995 | Perry |
| D358,801 S | 5/1995 | Vos |
| 5,411,041 A | 5/1995 | Ritter |
| 5,412,827 A | 5/1995 | Muller et al. |
| 5,416,942 A | 5/1995 | Baldacci et al. |
| 5,419,346 A | 5/1995 | Tipp |
| 5,419,703 A | 5/1995 | Warrin et al. |
| D358,938 S | 6/1995 | Schneider et al. |
| 5,421,726 A | 6/1995 | Okada |
| 5,435,032 A | 7/1995 | McDougall |
| 5,438,726 A | 8/1995 | Leite |
| 5,446,940 A | 9/1995 | Curtis et al. |
| D363,605 S | 10/1995 | Kou et al. |
| 5,459,898 A | 10/1995 | Bacolot |
| 5,461,744 A | 10/1995 | Merbach |
| 5,467,494 A | 11/1995 | Muller et al. |
| 5,467,495 A | 11/1995 | Boland et al. |
| 5,482,466 A | 1/1996 | Haynes |
| 5,484,281 A | 1/1996 | Renow et al. |
| 5,496,256 A | 3/1996 | Bock et al. |
| 5,499,420 A | 3/1996 | Boland |
| 5,504,958 A | 4/1996 | Herzog |
| 5,504,959 A | 4/1996 | Yukawa et al. |

(56) References Cited

U.S. PATENT DOCUMENTS

| | | |
|---|---|---|
| 5,511,270 A | 4/1996 | Eliachar et al. |
| 5,511,275 A | 4/1996 | Volpenhein et al. |
| D370,125 S | 5/1996 | Craft et al. |
| 5,518,012 A | 5/1996 | Dolan et al. |
| D370,347 S | 6/1996 | Heinzelman et al. |
| 5,529,494 A | 6/1996 | Vlacancich |
| D371,242 S | 7/1996 | Shimatsu et al. |
| 5,530,981 A | 7/1996 | Chen |
| 5,544,382 A | 8/1996 | Giuliani et al. |
| 5,545,968 A | 8/1996 | Hilfinger et al. |
| 5,546,624 A | 8/1996 | Bock |
| 5,546,626 A | 8/1996 | Chung |
| 5,561,881 A | 10/1996 | Klinger et al. |
| D375,841 S | 11/1996 | Serbinski |
| 5,573,020 A | 11/1996 | Robinson |
| 5,577,285 A | 11/1996 | Drossler |
| D376,695 S | 12/1996 | Tveras |
| 5,579,786 A | 12/1996 | Wolk et al. |
| 5,584,690 A | 12/1996 | Maassarani |
| 5,588,452 A | 12/1996 | Peck |
| 5,606,984 A | 3/1997 | Gao |
| 5,609,170 A | 3/1997 | Roth |
| 5,613,258 A | 3/1997 | Hilfinger et al. |
| 5,613,259 A | 3/1997 | Craft et al. |
| 5,617,601 A | 4/1997 | McDougall |
| 5,617,602 A | 4/1997 | Okada |
| 5,618,275 A | 4/1997 | Bock |
| 5,619,766 A | 4/1997 | Zhadanov et al. |
| 5,623,746 A | 4/1997 | Ichiro |
| 5,625,916 A | 5/1997 | McDougall |
| 5,628,082 A | 5/1997 | Moskovich |
| D380,903 S | 7/1997 | Moskovich |
| D381,468 S | 7/1997 | Dolan et al. |
| 5,651,157 A | 7/1997 | Hahn |
| D382,407 S | 8/1997 | Craft et al. |
| 5,652,990 A | 8/1997 | Driesen et al. |
| 5,653,591 A | 8/1997 | Loge |
| 5,678,274 A | 10/1997 | Liu |
| 5,678,578 A | 10/1997 | Kossak et al. |
| D386,314 S | 11/1997 | Moskovich |
| 5,687,446 A | 11/1997 | Chen et al. |
| 5,697,117 A | 12/1997 | Craft |
| 5,700,146 A | 12/1997 | Kucar |
| RE35,712 E | 1/1998 | Murayama |
| 5,704,087 A | 1/1998 | Strub |
| 5,709,233 A | 1/1998 | Boland et al. |
| 5,718,667 A | 2/1998 | Sugimoto et al. |
| 5,732,433 A | 3/1998 | Göcking et al. |
| 5,735,011 A | 4/1998 | Asher |
| 5,738,575 A | 4/1998 | Bock |
| 5,742,972 A | 4/1998 | Bredall et al. |
| 5,749,380 A | 5/1998 | Zebuhr |
| 5,762,078 A | 6/1998 | Zebuhr |
| 5,775,346 A | 7/1998 | Szyszkowski |
| 5,784,742 A | 7/1998 | Giuliani et al. |
| 5,784,743 A | 7/1998 | Shek |
| D397,251 S | 8/1998 | Eguchi et al. |
| D397,254 S | 8/1998 | Moskovich |
| 5,787,908 A | 8/1998 | Robinson |
| 5,794,295 A | 8/1998 | Shen |
| 5,815,872 A | 10/1998 | Meginniss, III et al. |
| 5,816,271 A | 10/1998 | Urso |
| 5,822,821 A | 10/1998 | Sham |
| 5,827,064 A | 10/1998 | Bock |
| D400,713 S | 11/1998 | Solanki |
| 5,836,030 A | 11/1998 | Hazeu et al. |
| 5,842,244 A | 12/1998 | Hilfinger et al. |
| 5,850,655 A | 12/1998 | Göcking et al. |
| 5,851,514 A | 12/1998 | Hassan et al. |
| D403,511 S | 1/1999 | Serbinski |
| 5,855,216 A | 1/1999 | Robinson |
| 5,862,558 A | 1/1999 | Hilfinger et al. |
| 5,864,911 A | 2/1999 | Arnoux |
| 5,864,915 A | 2/1999 | Ra |
| 5,867,856 A | 2/1999 | Herzog |
| 5,875,797 A | 3/1999 | Chiang et al. |
| 5,893,175 A | 4/1999 | Cooper |
| 5,896,614 A | 4/1999 | Flewitt |
| 5,896,615 A | 4/1999 | Zaksenberg |
| 5,899,693 A | 5/1999 | Himeno et al. |
| 5,900,230 A | 5/1999 | Cutler |
| 5,901,397 A * | 5/1999 | Hafele ............ A61C 17/22 15/22.1 |
| D410,787 S | 6/1999 | Barre et al. |
| 5,908,038 A | 6/1999 | Bennett |
| D411,769 S | 7/1999 | Wright |
| 5,921,254 A | 7/1999 | Carlucci et al. |
| 5,927,300 A | 7/1999 | Boland et al. |
| 5,927,976 A | 7/1999 | Wu |
| 5,930,858 A | 8/1999 | Jung |
| 5,931,170 A | 8/1999 | Wu |
| 5,934,908 A | 8/1999 | Woog et al. |
| 5,943,723 A | 8/1999 | Hilfinger et al. |
| 5,944,033 A | 8/1999 | Robinson |
| D413,694 S | 9/1999 | Bennett |
| D414,937 S | 10/1999 | Cornu et al. |
| D414,939 S | 10/1999 | Pedro, Jr. et al. |
| 5,974,613 A | 11/1999 | Herzog |
| 5,974,615 A | 11/1999 | Schwarz-Hartmann et al. |
| 5,980,541 A | 11/1999 | Tenzer |
| 5,987,681 A | 11/1999 | Hahn et al. |
| 5,991,957 A | 11/1999 | Watanabe |
| D417,960 S | 12/1999 | Moskovich et al. |
| 6,000,083 A | 12/1999 | Blaustein et al. |
| 6,009,589 A | 1/2000 | Driesen et al. |
| 6,021,538 A | 2/2000 | Kressner et al. |
| 6,026,828 A | 2/2000 | Altshuler |
| 6,032,313 A | 3/2000 | Tsang |
| 6,035,476 A | 3/2000 | Underwood et al. |
| 6,047,711 A | 4/2000 | Wagner |
| 6,050,818 A | 4/2000 | Boland et al. |
| RE36,699 E | 5/2000 | Murayama |
| D423,784 S | 5/2000 | Joulin |
| 6,065,176 A | 5/2000 | Watanabe et al. |
| 6,081,957 A | 7/2000 | Webb |
| 6,092,252 A | 7/2000 | Fischer et al. |
| 6,095,811 A | 8/2000 | Stearns |
| 6,102,700 A | 8/2000 | Haczek et al. |
| 6,106,294 A | 8/2000 | Daniel |
| 6,138,310 A | 10/2000 | Porper et al. |
| 6,140,723 A | 10/2000 | Matsui et al. |
| 6,148,462 A | 11/2000 | Zseng |
| D434,563 S | 12/2000 | Lim et al. |
| 6,154,912 A | 12/2000 | Li |
| 6,162,202 A | 12/2000 | Sicurelli et al. |
| 6,165,131 A | 12/2000 | Cuse et al. |
| D437,090 S | 1/2001 | Lang et al. |
| D437,091 S | 1/2001 | Lang et al. |
| 6,178,579 B1 | 1/2001 | Blaustein et al. |
| D437,663 S | 2/2001 | Lang et al. |
| D437,976 S | 2/2001 | Narayanan et al. |
| D437,977 S | 2/2001 | Lang et al. |
| D438,306 S | 2/2001 | Narayanan |
| 6,183,254 B1 | 2/2001 | Cohen |
| 6,195,828 B1 | 3/2001 | Fritsch |
| 6,202,242 B1 | 3/2001 | Salmon et al. |
| 6,203,320 B1 | 3/2001 | Williams et al. |
| 6,220,857 B1 | 4/2001 | Abels |
| 6,230,354 B1 | 5/2001 | Sproat |
| 6,230,717 B1 | 5/2001 | Marx et al. |
| 6,233,773 B1 | 5/2001 | Karge et al. |
| 6,237,178 B1 | 5/2001 | Krammer et al. |
| D444,629 S | 7/2001 | Etter et al. |
| 6,253,404 B1 | 7/2001 | Boland et al. |
| 6,267,593 B1 | 7/2001 | Haczek et al. |
| 6,299,444 B1 | 10/2001 | Cohen |
| 6,308,358 B2 | 10/2001 | Gruber et al. |
| 6,308,359 B2 | 10/2001 | Fritsch et al. |
| 6,341,400 B1 | 1/2002 | Kobayashi et al. |
| 6,343,396 B1 | 2/2002 | Simovitz et al. |
| 6,343,400 B1 | 2/2002 | Massholder et al. |
| 6,347,425 B1 | 2/2002 | Fattori et al. |
| 6,349,442 B1 | 2/2002 | Cohen et al. |
| 6,353,956 B1 | 3/2002 | Berge |

(56) References Cited

U.S. PATENT DOCUMENTS

| | | | |
|---|---|---|---|
| 6,360,395 B2 | 3/2002 | Blaustein et al. |
| 6,360,398 B1 | 3/2002 | Wiegner et al. |
| 6,363,565 B1 | 4/2002 | Paffrath |
| 6,365,108 B1 | 4/2002 | Philyaw |
| 6,367,108 B1 | 4/2002 | Fritsch et al. |
| 6,374,448 B2 | 4/2002 | Seifert |
| 6,375,459 B1 | 4/2002 | Kamen et al. |
| 6,381,795 B1 | 5/2002 | Hofmann et al. |
| 6,401,288 B1 | 6/2002 | Porper et al. |
| 6,421,865 B1 | 7/2002 | McDougall |
| 6,421,866 B1 | 7/2002 | McDougall |
| 6,421,867 B1 | 7/2002 | Weihrauch |
| 6,422,867 B2 | 7/2002 | Lang et al. |
| 6,434,773 B1 | 8/2002 | Kuo |
| D463,627 S | 9/2002 | Lang et al. |
| 6,446,294 B1 | 9/2002 | Specht |
| 6,446,295 B1 | 9/2002 | Calabrese |
| 6,447,293 B1 | 9/2002 | Sokol et al. |
| 6,453,497 B1 | 9/2002 | Chiang et al. |
| 6,453,498 B1 * | 9/2002 | Wu | A61C 17/40 15/22.1 |
| 6,453,499 B1 | 9/2002 | Leuermann |
| 6,463,615 B1 | 10/2002 | Gruber et al. |
| 6,490,747 B1 | 12/2002 | Metwally |
| 6,497,237 B1 | 12/2002 | Ali |
| 6,510,575 B2 | 1/2003 | Calabrese |
| 6,526,994 B1 | 3/2003 | Santoro |
| 6,536,066 B2 | 3/2003 | Dickie |
| 6,564,940 B2 | 5/2003 | Blaustein et al. |
| 6,571,804 B2 | 6/2003 | Adler |
| 6,574,820 B1 | 6/2003 | DePuydt et al. |
| 6,581,233 B1 | 6/2003 | Cheng |
| 6,581,234 B2 | 6/2003 | Lee et al. |
| 6,588,042 B2 | 7/2003 | Fritsch et al. |
| 6,599,048 B2 | 7/2003 | Kuo |
| 6,609,527 B2 | 8/2003 | Brown |
| 6,609,910 B2 | 8/2003 | Narayanan |
| 6,619,299 B2 | 9/2003 | Marcon et al. |
| 6,622,333 B1 | 9/2003 | Rehkemper et al. |
| 6,647,577 B2 | 11/2003 | Tam |
| D484,311 S | 12/2003 | Cacka et al. |
| 6,654,979 B2 | 12/2003 | Calabrese |
| 6,659,674 B2 | 12/2003 | Carlucci et al. |
| 6,665,901 B2 | 12/2003 | Driesen et al. |
| 6,691,363 B2 | 2/2004 | Huen |
| 6,701,565 B2 | 3/2004 | Hafemann |
| 6,709,185 B2 | 3/2004 | Lefevre |
| 6,721,986 B2 | 4/2004 | Zhuan |
| 6,725,490 B2 | 4/2004 | Blaustein et al. |
| 6,735,803 B2 | 5/2004 | Kuo |
| 6,735,804 B2 | 5/2004 | Carlucci et al. |
| 6,739,012 B2 | 5/2004 | Grez et al. |
| 6,751,823 B2 | 6/2004 | Biro et al. |
| 6,760,945 B2 | 7/2004 | Ferber et al. |
| 6,760,946 B2 | 7/2004 | DePuydt |
| 6,766,548 B1 | 7/2004 | Lukas et al. |
| 6,766,549 B2 | 7/2004 | Klupt |
| 6,766,807 B2 | 7/2004 | Piccolo et al. |
| 6,779,126 B1 | 8/2004 | Lin et al. |
| 6,779,215 B2 | 8/2004 | Hartman et al. |
| 6,785,926 B2 | 9/2004 | Green |
| 6,785,929 B2 | 9/2004 | Fritsch et al. |
| 6,792,640 B2 | 9/2004 | Lev |
| 6,795,993 B2 | 9/2004 | Lin |
| 6,798,169 B2 | 9/2004 | Stratmann et al. |
| 6,799,346 B2 | 10/2004 | Jeng et al. |
| 6,802,097 B2 | 10/2004 | Hafliger et al. |
| 6,810,550 B1 | 11/2004 | Wuelknitz et al. |
| 6,813,793 B2 | 11/2004 | Eliav |
| 6,813,794 B2 | 11/2004 | Weng |
| 6,821,119 B2 | 11/2004 | Shortt et al. |
| 6,823,875 B2 | 11/2004 | Hotta et al. |
| 6,827,910 B2 | 12/2004 | Chen |
| 6,829,801 B2 | 12/2004 | Schutz |
| 6,832,819 B1 | 12/2004 | Weihrauch |
| D500,599 S | 1/2005 | Callaghan |
| D501,084 S | 1/2005 | Schaefer et al. |
| 6,836,917 B2 | 1/2005 | Blaustein et al. |
| 6,845,537 B2 | 1/2005 | Wong |
| 6,848,141 B2 | 2/2005 | Eliav et al. |
| 6,851,150 B2 | 2/2005 | Chiang |
| 6,851,153 B2 | 2/2005 | Lehman |
| 6,854,965 B2 | 2/2005 | Ebner et al. |
| 6,862,771 B1 | 3/2005 | Muller |
| 6,871,373 B2 | 3/2005 | Driesen et al. |
| 6,874,509 B2 | 4/2005 | Bergman |
| 6,886,207 B1 | 5/2005 | Solanki |
| 6,889,401 B2 | 5/2005 | Fattori et al. |
| 6,889,829 B2 | 5/2005 | Lev et al. |
| 6,892,412 B2 | 5/2005 | Gatzemeyer et al. |
| 6,892,413 B2 | 5/2005 | Blaustein et al. |
| 6,895,625 B2 | 5/2005 | Lev et al. |
| 6,895,629 B1 | 5/2005 | Wenzler |
| 6,902,337 B1 | 6/2005 | Kuo |
| 6,907,636 B2 | 6/2005 | Hafemann |
| 6,918,153 B2 | 7/2005 | Gruber |
| 6,920,659 B2 * | 7/2005 | Cacka | A61C 17/225 15/22.1 |
| 6,920,660 B2 | 7/2005 | Lam |
| 6,928,685 B1 | 8/2005 | Blaustein et al. |
| 6,931,688 B2 | 8/2005 | Moskovich et al. |
| 6,938,293 B2 | 9/2005 | Eliav et al. |
| 6,938,294 B2 | 9/2005 | Fattori et al. |
| 6,944,901 B2 | 9/2005 | Gatzemeyer et al. |
| 6,945,397 B2 | 9/2005 | Brattesani et al. |
| 6,948,209 B2 | 9/2005 | Chan |
| 6,952,854 B2 | 10/2005 | Blaustein et al. |
| 6,952,855 B2 | 10/2005 | Lev et al. |
| 6,954,961 B2 | 10/2005 | Ferber et al. |
| 6,955,539 B2 | 10/2005 | Shortt et al. |
| 6,957,468 B2 | 10/2005 | Driesen et al. |
| 6,957,469 B2 | 10/2005 | Davies |
| 6,966,093 B2 | 11/2005 | Eliav et al. |
| 6,973,694 B2 | 12/2005 | Schutz et al. |
| 6,983,507 B2 | 1/2006 | McDougall |
| 6,988,777 B2 | 1/2006 | Pfenniger et al. |
| 6,990,706 B2 | 1/2006 | Broecker et al. |
| D515,318 S | 2/2006 | Chan et al. |
| 6,993,803 B2 | 2/2006 | Chan |
| 6,997,191 B2 | 2/2006 | Nudo, Sr. |
| 7,007,331 B2 | 3/2006 | Davies et al. |
| 7,008,225 B2 | 3/2006 | Ito et al. |
| 7,020,925 B1 | 4/2006 | Gitelis |
| 7,021,851 B1 | 4/2006 | King |
| 7,024,717 B2 | 4/2006 | Hilscher et al. |
| 7,024,718 B2 | 4/2006 | Chu |
| 7,036,180 B2 | 5/2006 | Hanlon |
| 7,055,205 B2 | 6/2006 | Aoyama |
| 7,059,334 B2 | 6/2006 | Dougan et al. |
| 7,065,821 B2 | 6/2006 | Fattori |
| RE39,185 E | 7/2006 | Noe et al. |
| 7,070,354 B1 | 7/2006 | Gutierrez-Caro |
| 7,080,980 B2 | 7/2006 | Klupt |
| 7,082,638 B2 | 8/2006 | Koh |
| 7,082,950 B2 | 8/2006 | Kossak et al. |
| 7,086,111 B2 | 8/2006 | Hilscher et al. |
| 7,089,621 B2 | 8/2006 | Hohlbein |
| 7,120,960 B2 | 10/2006 | Hilscher et al. |
| 7,122,921 B2 | 10/2006 | Hall et al. |
| 7,124,461 B2 | 10/2006 | Blaustein et al. |
| 7,124,462 B2 | 10/2006 | Lee |
| 7,128,492 B1 | 10/2006 | Thames, Jr. |
| 7,137,163 B2 | 11/2006 | Gatzemeyer et al. |
| 7,140,058 B2 | 11/2006 | Gatzemeyer et al. |
| 7,146,675 B2 | 12/2006 | Ansari et al. |
| 7,162,764 B2 | 1/2007 | Drossler et al. |
| 7,162,767 B2 | 1/2007 | Pfenniger et al. |
| 7,168,122 B1 | 1/2007 | Riddell |
| 7,168,125 B2 | 1/2007 | Hohlbein |
| 7,174,596 B2 | 2/2007 | Fischer et al. |
| 7,175,238 B1 | 2/2007 | Barman |
| 7,181,799 B2 | 2/2007 | Gavney, Jr. et al. |
| 7,185,383 B2 | 3/2007 | Gatzemeyer et al. |
| 7,186,226 B2 | 3/2007 | Woolley |

(56) References Cited

U.S. PATENT DOCUMENTS

| | | | |
|---|---|---|---|
| D540,542 S | 4/2007 | Harada | |
| 7,198,487 B2 | 4/2007 | Luettgen et al. | |
| 7,207,080 B2 | 4/2007 | Hilscher et al. | |
| 7,210,184 B2 | 5/2007 | Eliav et al. | |
| 7,213,293 B1 | 5/2007 | Schraga | |
| 7,213,995 B2 | 5/2007 | Bravo-Loubriel | |
| 7,217,332 B2 | 5/2007 | Brown, Jr. et al. | |
| 7,222,381 B2* | 5/2007 | Kraemer | A61C 17/222 15/22.1 |
| 7,222,382 B2 | 5/2007 | Choi et al. | |
| 7,225,494 B2 | 6/2007 | Chan et al. | |
| 7,228,583 B2 | 6/2007 | Chan et al. | |
| 7,234,187 B2 | 6/2007 | Blaustein et al. | |
| 7,234,192 B2 | 6/2007 | Barbar | |
| 7,469,440 B2 | 12/2008 | Boland et al. | |
| 7,554,225 B2 | 6/2009 | Kraus et al. | |
| 7,732,952 B1* | 6/2010 | Taylor | A61C 17/20 15/22.1 |
| 8,032,964 B2 | 10/2011 | Farrell et al. | |
| 2001/0035194 A1 | 11/2001 | Narayanan | |
| 2001/0039955 A1 | 11/2001 | Winters et al. | |
| 2001/0054563 A1 | 12/2001 | Lang et al. | |
| 2002/0017474 A1 | 2/2002 | Blaustein et al. | |
| 2002/0029988 A1 | 3/2002 | Blaustein et al. | |
| 2002/0032941 A1 | 3/2002 | Blaustein et al. | |
| 2002/0039720 A1 | 4/2002 | Marx et al. | |
| 2002/0059685 A1 | 5/2002 | Paffrath | |
| 2002/0078514 A1 | 6/2002 | Blaustein et al. | |
| 2002/0084707 A1 | 7/2002 | Tang | |
| 2002/0088068 A1 | 7/2002 | Levy et al. | |
| 2002/0090252 A1 | 7/2002 | Hall et al. | |
| 2002/0092104 A1* | 7/2002 | Ferber | A61C 17/224 15/22.1 |
| 2002/0095734 A1 | 7/2002 | Wong | |
| 2002/0100134 A1 | 8/2002 | Dunn et al. | |
| 2002/0106607 A1 | 8/2002 | Horowitz | |
| 2002/0137728 A1 | 9/2002 | Montgomery | |
| 2002/0138926 A1 | 10/2002 | Brown, Jr. et al. | |
| 2002/0152563 A1 | 10/2002 | Sato | |
| 2002/0152564 A1 | 10/2002 | Blaustein et al. | |
| 2002/0174498 A1 | 11/2002 | Li | |
| 2002/0178519 A1 | 12/2002 | Zarlengo | |
| 2003/0005544 A1 | 1/2003 | Felix | |
| 2003/0033679 A1 | 2/2003 | Fattori et al. | |
| 2003/0033680 A1 | 2/2003 | Davies et al. | |
| 2003/0041396 A1 | 3/2003 | Dickie | |
| 2003/0064348 A1 | 4/2003 | Sokol et al. | |
| 2003/0066145 A1 | 4/2003 | Prineppi | |
| 2003/0074751 A1 | 4/2003 | Wu | |
| 2003/0079305 A1 | 5/2003 | Takahata et al. | |
| 2003/0084525 A1 | 5/2003 | Blaustein et al. | |
| 2003/0084526 A1 | 5/2003 | Brown et al. | |
| 2003/0084527 A1 | 5/2003 | Brown et al. | |
| 2003/0097723 A1 | 5/2003 | Li | |
| 2003/0099502 A1 | 5/2003 | Lai | |
| 2003/0101526 A1* | 6/2003 | Hilscher | A61C 17/22 15/22.1 |
| 2003/0106565 A1 | 6/2003 | Andrews | |
| 2003/0140435 A1 | 7/2003 | Eliav et al. | |
| 2003/0140437 A1 | 7/2003 | Eliav et al. | |
| 2003/0140937 A1 | 7/2003 | Cook | |
| 2003/0150474 A1 | 8/2003 | Doyscher | |
| 2003/0154567 A1 | 8/2003 | Drossler et al. | |
| 2003/0154568 A1 | 8/2003 | Boland et al. | |
| 2003/0163881 A1 | 9/2003 | Driesen et al. | |
| 2003/0163882 A1 | 9/2003 | Blaustein et al. | |
| 2003/0182743 A1 | 10/2003 | Gatzemeyer et al. | |
| 2003/0182746 A1 | 10/2003 | Fattori et al. | |
| 2003/0192139 A1 | 10/2003 | Fattori et al. | |
| 2003/0196283 A1 | 10/2003 | Eliav et al. | |
| 2003/0196677 A1 | 10/2003 | Wiseman | |
| 2003/0213075 A1 | 11/2003 | Hui et al. | |
| 2003/0221267 A1 | 12/2003 | Chan | |
| 2003/0221269 A1 | 12/2003 | Zhuan | |
| 2003/0226223 A1 | 12/2003 | Chan | |
| 2004/0010870 A1 | 1/2004 | McNair | |
| 2004/0010871 A1 | 1/2004 | Nishinaka et al. | |
| 2004/0016068 A1 | 1/2004 | Lee | |
| 2004/0016069 A1 | 1/2004 | Lee | |
| 2004/0034951 A1 | 2/2004 | Davies et al. | |
| 2004/0045106 A1 | 3/2004 | Lam | |
| 2004/0045107 A1 | 3/2004 | Egeresi | |
| 2004/0049867 A1 | 3/2004 | Hui | |
| 2004/0049868 A1 | 3/2004 | Ng | |
| 2004/0060137 A1 | 4/2004 | Eliav | |
| 2004/0063603 A1 | 4/2004 | Dave et al. | |
| 2004/0068811 A1 | 4/2004 | Fulop et al. | |
| 2004/0074026 A1 | 4/2004 | Blaustein et al. | |
| 2004/0083566 A1 | 5/2004 | Blaustein et al. | |
| 2004/0087882 A1 | 5/2004 | Roberts et al. | |
| 2004/0088806 A1 | 5/2004 | DePuydt et al. | |
| 2004/0088807 A1 | 5/2004 | Blaustein et al. | |
| 2004/0091834 A1 | 5/2004 | Rizoiu et al. | |
| 2004/0107521 A1 | 6/2004 | Chan et al. | |
| 2004/0119314 A1 | 6/2004 | Lau et al. | |
| 2004/0123409 A1 | 7/2004 | Dickie | |
| 2004/0128778 A1 | 7/2004 | Wong | |
| 2004/0129296 A1 | 7/2004 | Treacy et al. | |
| 2004/0134001 A1 | 7/2004 | Chan | |
| 2004/0143917 A1 | 7/2004 | Ek | |
| 2004/0154112 A1 | 8/2004 | Braun et al. | |
| 2004/0163191 A1 | 8/2004 | Cuffaro et al. | |
| 2004/0168269 A1 | 9/2004 | Kunita et al. | |
| 2004/0168272 A1 | 9/2004 | Prineppi | |
| 2004/0177458 A1 | 9/2004 | Chan et al. | |
| 2004/0187889 A1 | 9/2004 | Kemp et al. | |
| 2004/0200016 A1 | 10/2004 | Chan et al. | |
| 2005/0008986 A1 | 1/2005 | Sokol et al. | |
| 2005/0189000 A1 | 9/2005 | Cacka et al. | |
| 2005/0255427 A1 | 11/2005 | Shortt et al. | |
| 2005/0266376 A1 | 12/2005 | Sokol et al. | |
| 2007/0151051 A1* | 7/2007 | Filsouf | A61C 17/40 15/22.1 |
| 2008/0213731 A1 | 9/2008 | Fishburne | |
| 2009/0019650 A1* | 1/2009 | Dickie | A61C 17/3472 15/22.1 |
| 2009/0019651 A1* | 1/2009 | Grez | A61C 17/222 15/22.1 |
| 2009/0178215 A1* | 7/2009 | Gall | A46B 13/023 15/22.1 |
| 2010/0055634 A1 | 3/2010 | Spaulding et al. | |
| 2010/0132139 A1 | 6/2010 | Jungnickel | |
| 2010/0186179 A1* | 7/2010 | Miller | A61C 1/07 15/22.2 |
| 2011/0041268 A1 | 2/2011 | Iwahori et al. | |
| 2011/0047729 A1* | 3/2011 | Iwahori | A61C 17/3481 15/22.1 |
| 2011/0083288 A1* | 4/2011 | Kressner | A61C 17/222 15/22.1 |
| 2012/0112566 A1* | 5/2012 | Doll | B26B 19/28 310/37 |
| 2012/0192366 A1* | 8/2012 | Cobabe | A46B 7/04 15/4 |
| 2012/0198635 A1* | 8/2012 | Hilscher | A61B 18/00 15/22.1 |
| 2012/0216358 A1* | 8/2012 | Kloster | A61C 17/3481 15/22.2 |
| 2015/0107035 A1 | 4/2015 | Sokol et al. | |

FOREIGN PATENT DOCUMENTS

| | | |
|---|---|---|
| CN | 201223467 | 4/2009 |
| DE | 243224 | 4/1910 |
| DE | 1766651 | 12/1981 |
| DE | 3431481 | 2/1986 |
| DE | 3512190 | 10/1986 |
| DE | 8626725 | 5/1987 |
| DE | 3736308 | 7/1989 |
| DE | 4142404 | 7/1991 |
| DE | 4003305 | 8/1991 |
| DE | 4223195 | 1/1994 |
| DE | 4223196 | 1/1994 |
| DE | 4226658 | 2/1994 |
| DE | 4226659 | 2/1994 |

(56) References Cited

FOREIGN PATENT DOCUMENTS

| | | |
|---|---|---|
| DE | 4241576 | 6/1994 |
| DE | 4309078 | 9/1994 |
| DE | 29715234 | 12/1997 |
| DE | 29919053 | 12/2000 |
| DE | 19961447 | 7/2001 |
| EP | 0210094 | 6/1986 |
| EP | 0354352 | 2/1990 |
| EP | 0661025 | 7/1995 |
| EP | 0704180 | 4/1996 |
| FR | 429447 | 9/1911 |
| FR | 1171337 | 1/1959 |
| GB | 477799 | 1/1938 |
| GB | 500517 | 2/1939 |
| GB | 899618 | 6/1962 |
| GB | 1583558 | 8/1977 |
| GB | 2175494 | 12/1986 |
| GB | 2250428 | 6/1992 |
| JP | 4012541 | 6/1965 |
| JP | 5321650 | 2/1978 |
| JP | 53029847 | 3/1978 |
| JP | 53033753 | 3/1978 |
| JP | 61217109 | 9/1986 |
| JP | 3222905 | 10/1991 |
| SE | 324221 | 5/1970 |
| WO | WO 91/13570 | 9/1991 |
| WO | WO 91/19437 | 12/1991 |
| WO | WO 92/10146 | 6/1992 |
| WO | WO 92/16160 | 10/1992 |
| WO | WO 93/10721 | 6/1993 |
| WO | WO 93/15628 | 8/1993 |
| WO | WO 94/04093 | 3/1994 |
| WO | WO 94/26144 | 11/1994 |
| WO | WO 95/02375 | 1/1995 |
| WO | WO 95/33419 | 12/1995 |
| WO | WO 98/47443 | 10/1998 |
| WO | WO 01/28452 | 4/2001 |
| WO | WO 01/45582 | 6/2001 |
| WO | WO 02/071970 | 9/2002 |
| WO | WO 02/071971 | 9/2002 |
| WO | WO2005/063143 | 7/2005 |

OTHER PUBLICATIONS

Teledyne Water Pik "Plaque Control 3000" plaque removal instrument (Jul. 1991).

American Dentronics Incorporated "Soniplak" sonic plaque removal system (May 1993).

Teledyne Water Pik "Sensonic" Toothbrush, sales brochure (at least as early as Sep. 1994).

Design of a Toothbrush, p. 361, Danish Official Design Gazette, published May 16, 1997.

International Search Report and Written Opinion, PCT Application No. PCT/US2012/036092, 8 pages, Jul. 10, 2012.

* cited by examiner

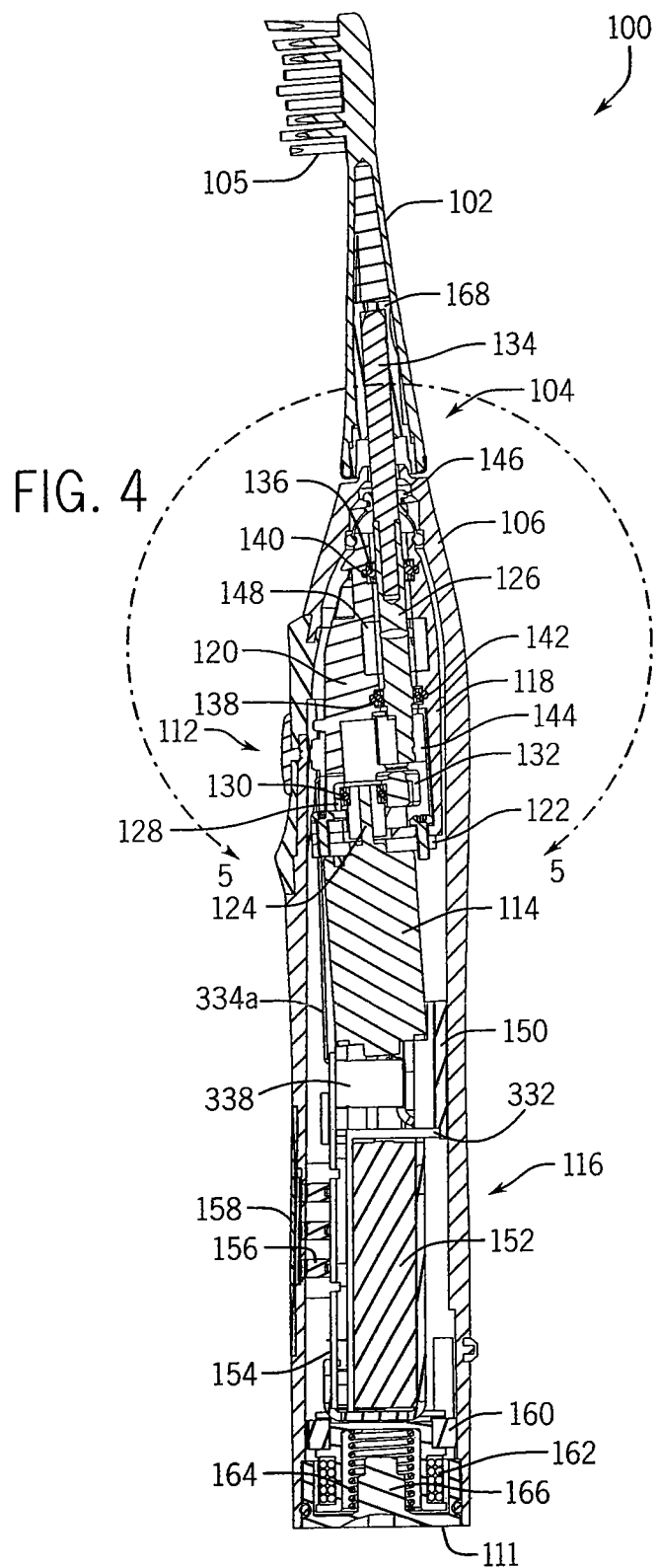

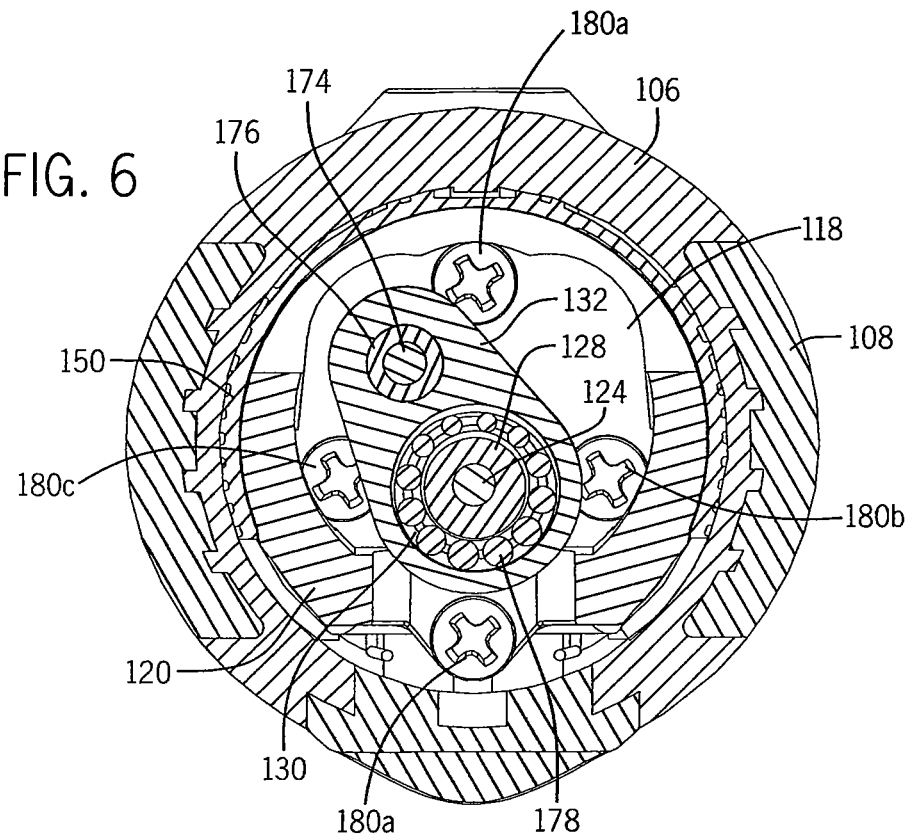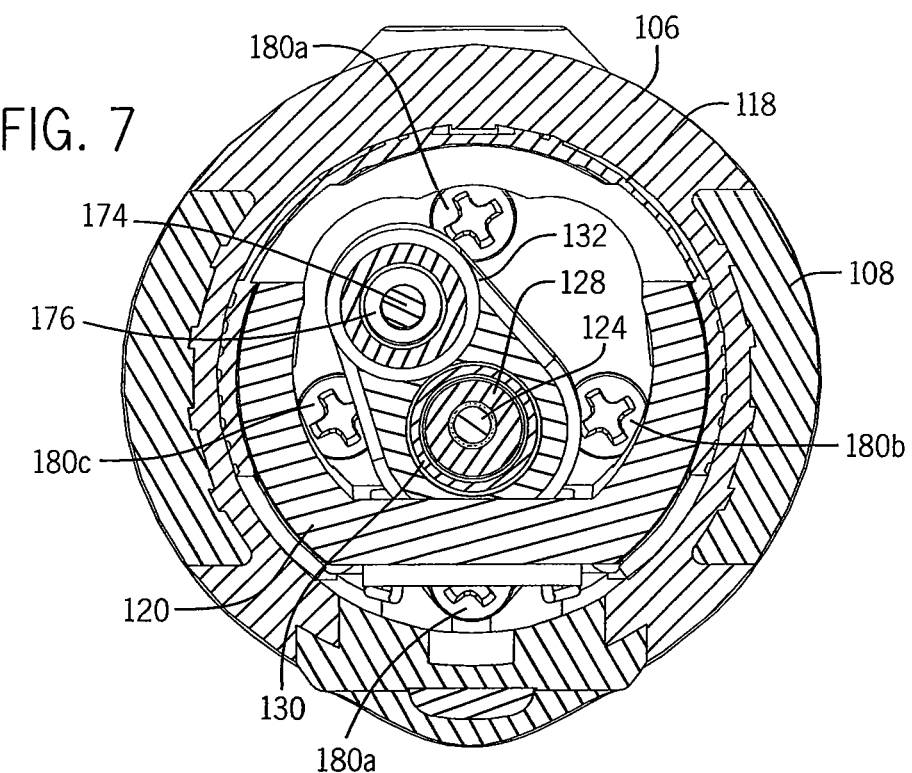

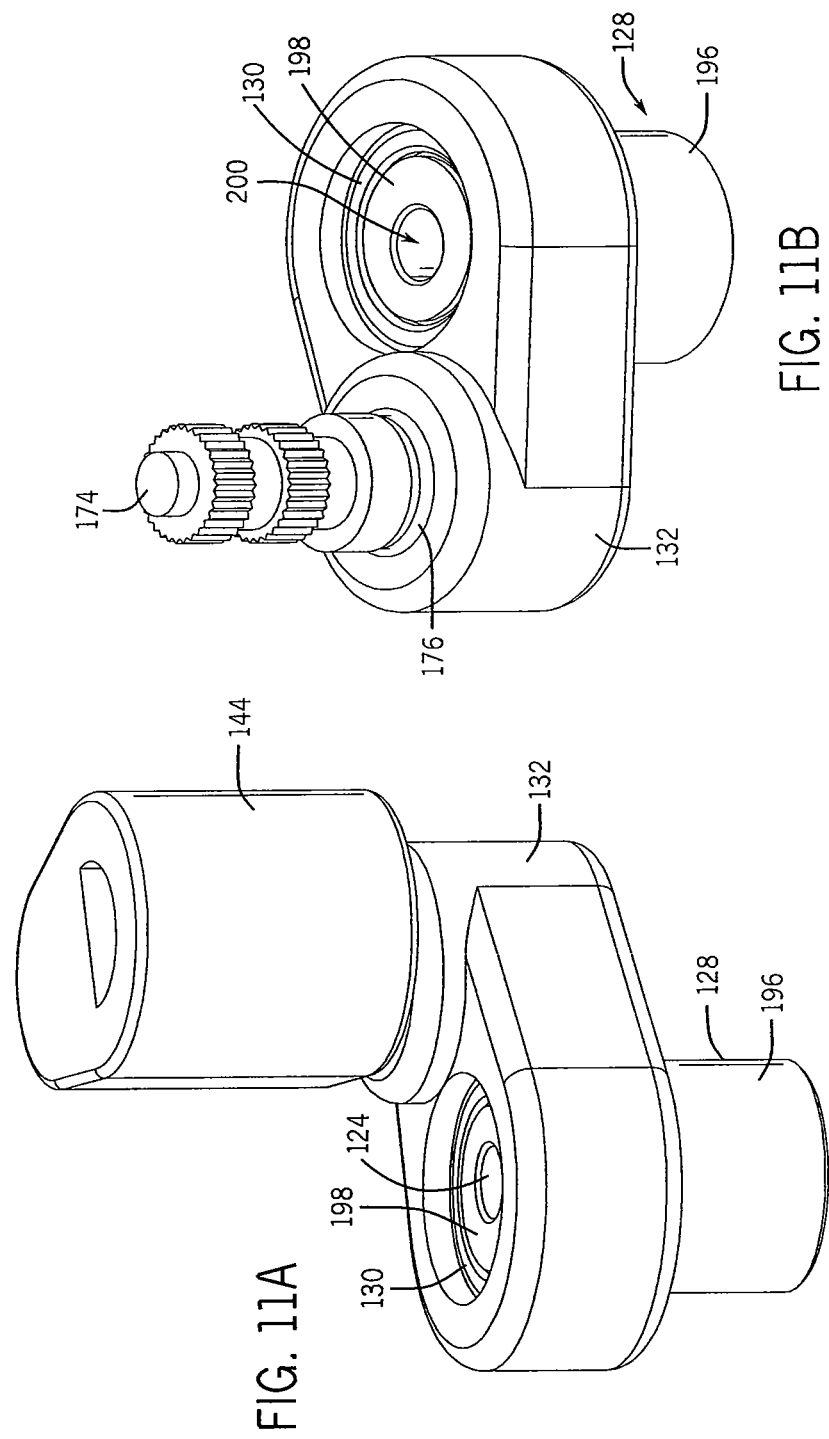

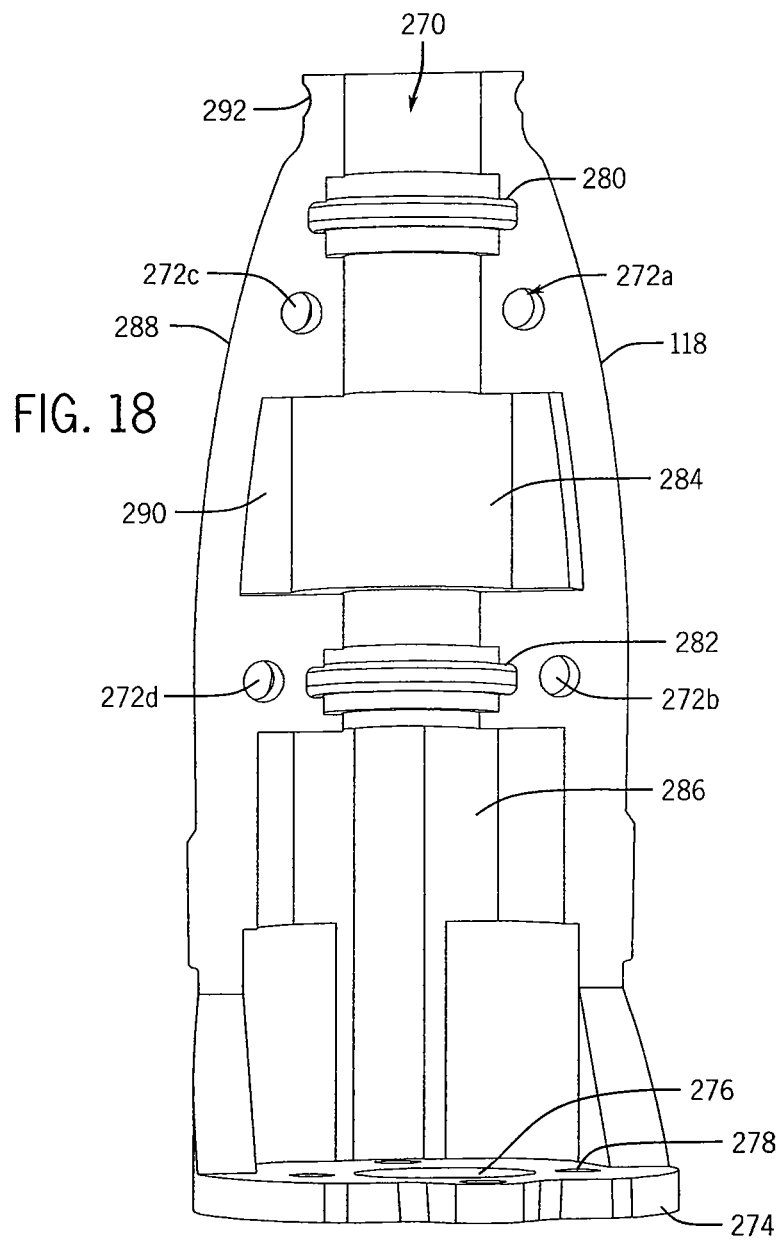

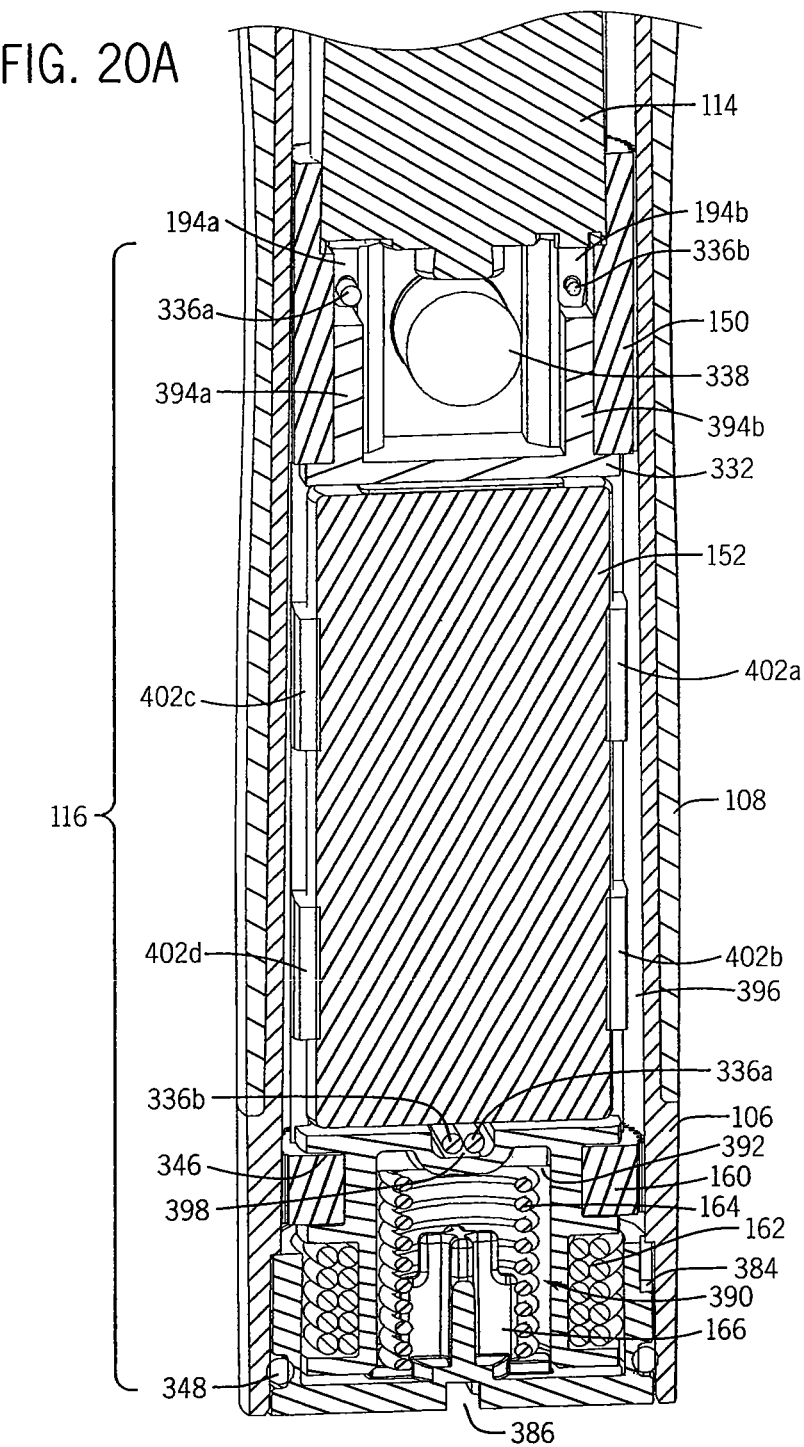

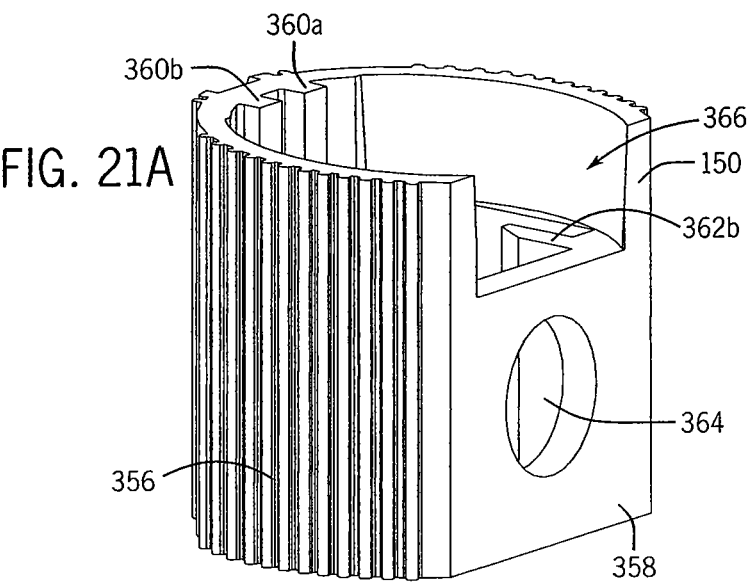
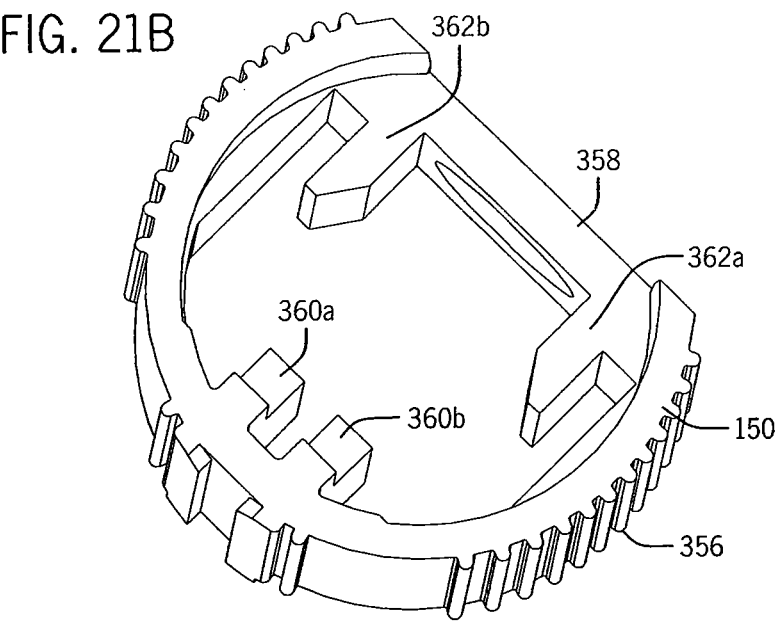

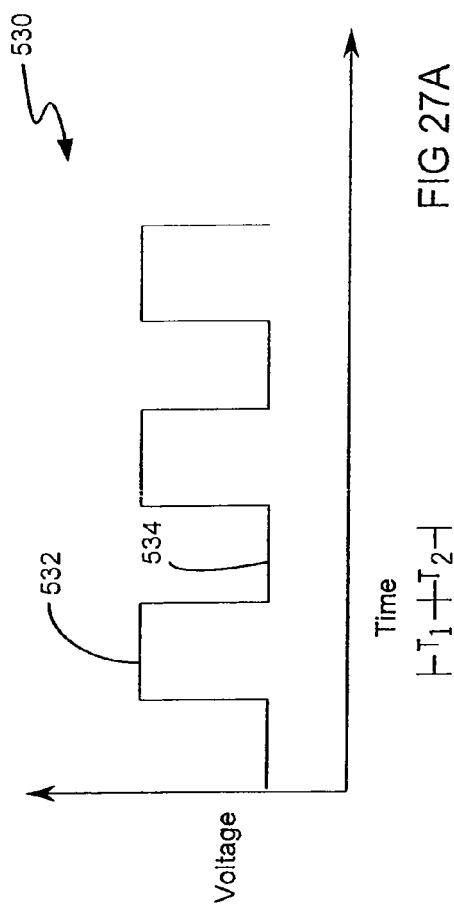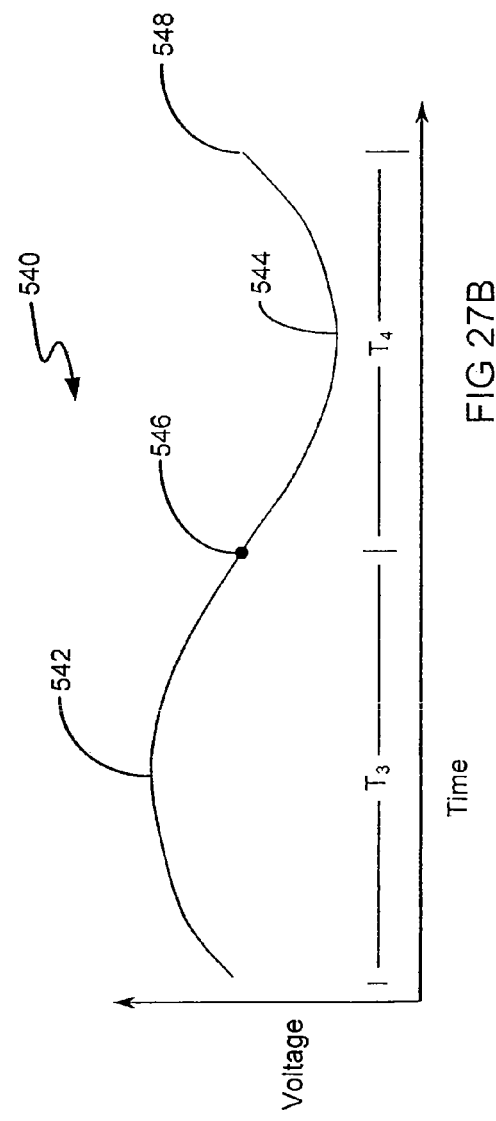

ELECTRONIC TOOTHBRUSH WITH VIBRATION DAMPENING

TECHNICAL FIELD

The technology described herein relates generally to toothbrushes and more particularly to electronically driven toothbrushes.

BACKGROUND

Electrically driven toothbrushes typically include a brush head having a plurality of bristles, where the brush head or the bristles are vibrated or rotated by a motor. The rotation and/or vibration of the brush head and/or bristles assists a user is cleaning his or her teeth and gums. Often the rotation of a drive shaft of the motor, as well as other components in the electronic toothbrush, may cause other components of the toothbrush, such as the handle, to vibrate or rotate as well. The vibration in the handle may be unpleasant to a user, as well as make it more difficult for a user to grip the handle and direct the motion of the toothbrush.

The information included in this Background section of the specification, including any references cited herein and any description or discussion thereof, is included for technical reference purposes only and is not to be regarded subject matter by which the scope of the invention is defined in the claims is to be bound.

SUMMARY

Some embodiments may include an electrically driven toothbrush including a brush head including a plurality of bristles, a motor, an output shaft connected to the brush head and the motor, wherein the output shaft is selectively rotated by the motor, and a bumper assembly connected to the output shaft and configured to conserve kinetic energy from the output shaft during rotation and reapply the kinetic energy to the output shaft.

In some examples, the bumper assembly includes a first bumper and a second bumper, where the first bumper and the second bumper substantially surround a portion of the output shaft.

The toothbrush may also include a linkage assembly connecting the motor to the output shaft and a chassis assembly supporting the motor and the linkage assembly. In these examples, the toothbrush may also include a housing attached to the brush head, wherein the motor, the output shaft, the linkage assembly, and the chassis assembly are received within the housing. A boot seal may be positioned between a top end of the chassis and an interior surface of the housing.

The toothbrush may also include at least two vibration absorbing pads formed within an interior surface of the housing, the vibration absorbing pads help to isolate the housing from vibration of the chassis.

Other embodiments may include an electrically driven toothbrush. The toothbrush may include a handle housing, a brush head releasably connected to the handle housing and including a plurality of bristles, a motor including a drive shaft connected to the brush head, an eccentric mounted to the drive shaft, the eccentric having a counterweight formed therein, and a bearing received around a portion of the eccentric. The counterweight of the eccentric counters the weight of the bearing.

In the above embodiments, the eccentric may include a body and a hub, wherein the body has an asymmetrical distribution of weight which forms the counterweight.

The electrically driven toothbrush may also include a linkage assembly connecting the drive shaft to the brush head and a chassis supporting the linkage assembly and the motor within the handle. The linkage assembly may include a link coupler connected to the bearing and the eccentric, a drive pin connected to the link coupler, a rocker connected to the drive pin, and an output shaft connected to the rocker and the brush head.

In some examples of the toothbrush the rocker is insert molded around the drive pin and/or output shaft. In other examples, the drive pin, the rocker, and the output shaft may be integrally connected together.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 4 is a cross-section view of the toothbrush taken along line 4-4 in FIG. 1A.

FIG. 6 is a cross-section view of the toothbrush taken along line 6-6 in FIG. 1A.

FIG. 7 is a cross-section view of the toothbrush taken along line 7-7 in FIG. 1A.

FIG. 11A is a perspective view of a linkage assembly for the toothbrush.

FIG. 11B is a perspective view of the linkage assembly of FIG. 11A with a rocker element hidden for clarity.

FIG. 18 is a front perspective view of a chassis of the toothbrush.

FIG. 20A is an enlarged cross-section view of the toothbrush taken along line 20A-20A in FIG. 1C.

FIG. 21A is a front perspective view of a first isolator of the toothbrush.

FIG. 21B is a top perspective view of the first isolator of FIG. 21A.

FIG. 27A is a diagram of a first example of a control signal output by a signal generator of the motor control circuit.

FIG. 27B is a diagram of a second example of a control signal output by a signal generator of the motor control circuit.

DETAILED DESCRIPTION

Figure 1A:
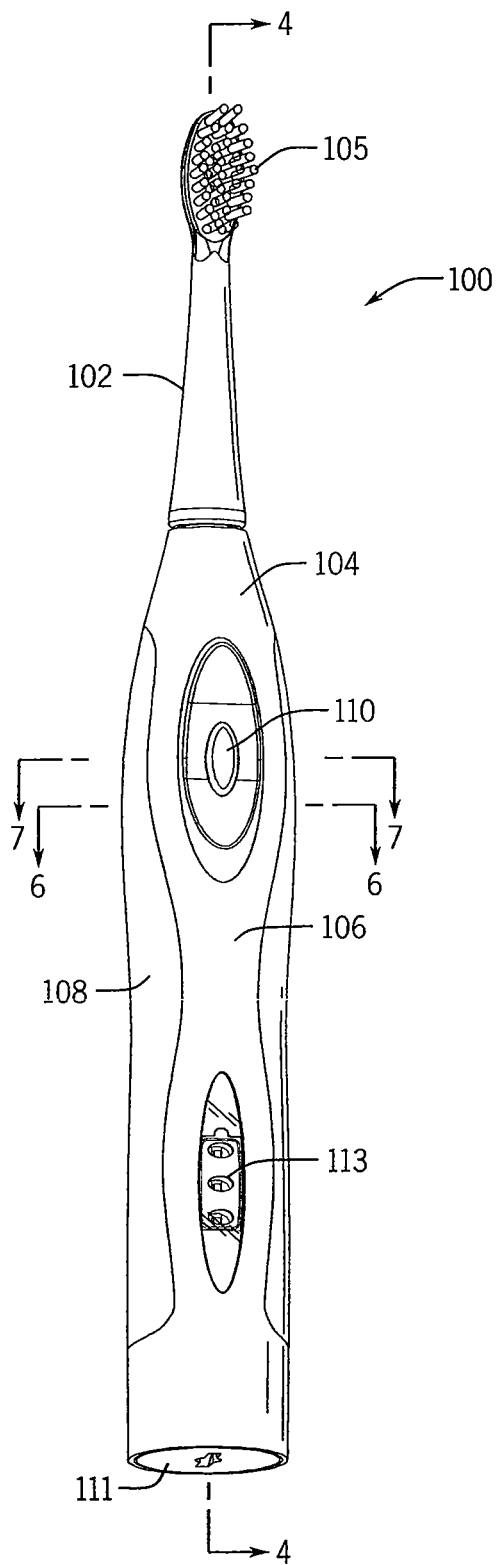
FIG. 1A is a front perspective view of an electrically driven toothbrush.
Figure 1B:
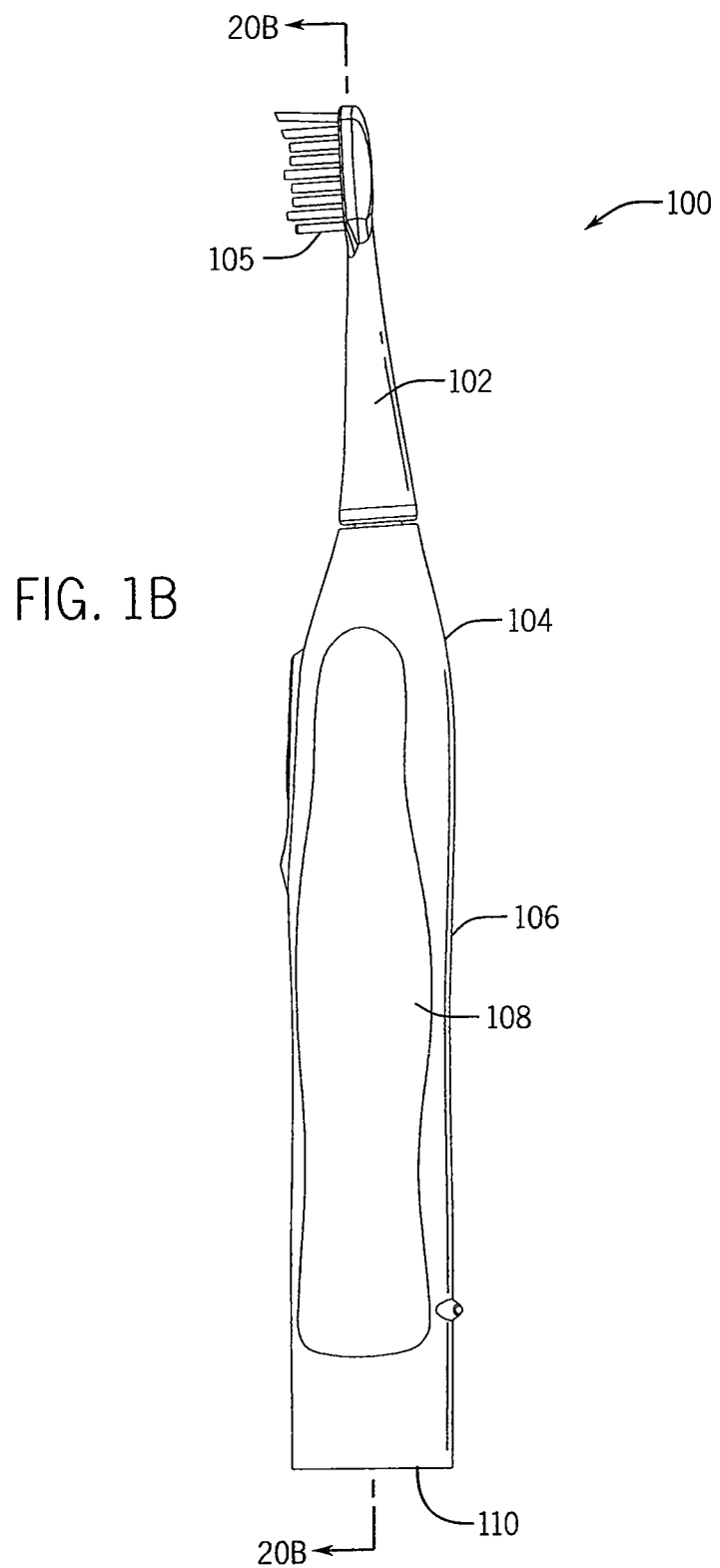
FIG. 1B is a side elevation view of the toothbrush.
Figure 1C:
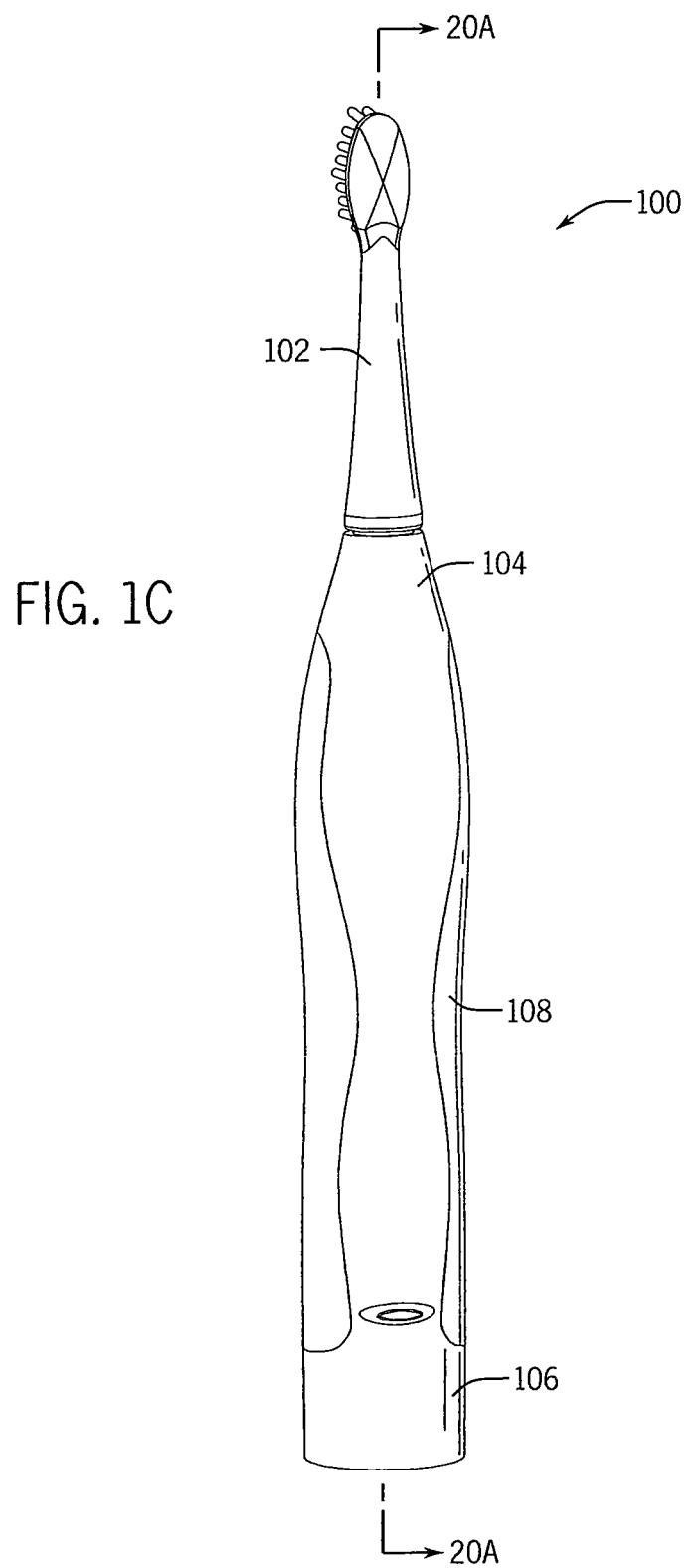
FIG. 1C is a rear perspective view of the toothbrush.
Figure 1D:
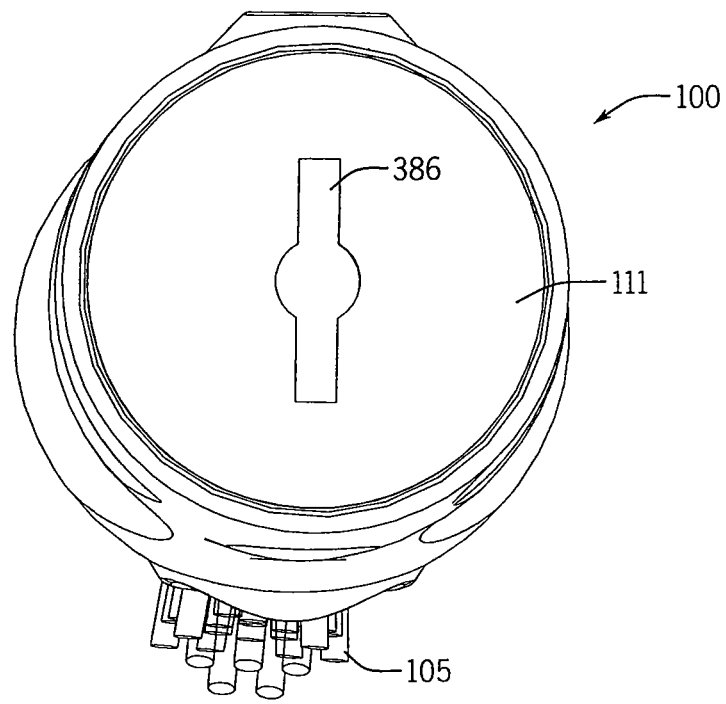
FIG. 1D is a bottom perspective view of the toothbrush.

Various examples of an electronically powered toothbrush are disclosed herein. The toothbrush may include a body, a brush head including a plurality of bristles, a drive assembly, a power assembly to provide power to the drive assembly, and a plurality of vibration and sound dampening components. Generally, in operation, the power assembly may provide power to the drive assembly, the drive assembly may then rotate and/or vibrate the brush head and bristles and the vibration and sound dampening components may reduce vibration from being transmitted from the motor to the body of the toothbrush, as well as may help to reduce current consumption of the power assembly.

The drive assembly may include a motor attached to the brush head through a linkage assembly, the linkage may include an eccentric connected to the motor shaft. In some embodiments, the eccentric may be attached to a ball bearing and the eccentric may include a counterweight formed therewith to balance the weight of the ball bearing. In these embodiments, the bearing and the counterweight assist in reducing current consumption, by reducing friction in the connection between the linkage assembly and the motor drive shaft, as well as reduce noise at the connection joint. In other words, the balanced eccentric including the ball bearing may result in a joint having a reduce amount of friction, which along with the balancing between the bearing and the counterweight, acts to reduce noise as the drive shaft is rotated.

The drive assembly may also include an output shaft selectively attachable to the brush head, as well as a drive pin that connects the output shaft to a coupler or linkage component to connect the output shaft to the drive shaft of the motor. In some embodiments, the drive pin and the output shaft may be connected together through an insert molding manufacturing process. By connecting the output shaft and drive pin together through an insert molding process, the connection joint may have little to no slop, which may prevent the assembly from becoming loose due to wear.

Additionally, the output shaft may include one or more ball bearings attached thereto. The ball bearings may further include a compressible component, such as an O-ring received around their outer surface. The ball bearings along with the dampeners or O-rings may reduce noise from the drive assembly. For example, the dampeners may prevent the bearings from rattling in instances where the fit between the bearing and the output shaft is loose or has some slop. Additionally, the dampeners may exert a uniform load on the bearings, which may prevent the bearings from being compressed (due to rotational forces) into a non-uniform shape, such as an oblong shape. Further, by reducing rattling noise, as well as preventing the bearings from being formed into non-uniform shapes, noise generated by the drive assembly may be reduced. This is because the rattling, as well as oblong or other non-uniform bearing shapes, may increase audible noise produced by the toothbrush.

The toothbrush may further include one or more bumpers attached to an output shaft. For example, the output shaft may include two rubber bumpers connected around the output drive shaft by a dowel pin. The bumpers absorb kinetic energy from the angular velocity of the output shaft and may then reapply the energy to reverse the direction of rotation. By reapplying absorbed energy to modify the rotation direction of the output shaft, the power required to rotate the brush head in a particular pattern may be reduced. In some instances, the dowel pin may extend through the output shaft to contact a first bumper and a second bumper. In these instances, the ends of the dowel pin may experience contact from the rubber bumpers substantially simultaneously and in opposite directions (due to the rotation of the shaft and subsequent movement of the bumpers therewith). The force experienced by the ends of the dowel pin may provide torque to the shaft, which further acts to conserve energy. The torque provided may be a pure reversal torque in that the net force reaction on the output shaft may be only torque without any side loads that could result in additional audible noise and wear on the bearings and other linkage components, as well as waste energy. In addition to conserving energy, the bumpers and dowel pin may further reduce wear and tear on the output shaft and other components of the linkage between the drive shaft and the output shaft, by reducing movement and friction.

In some instances, one or more components of the drive assembly may be formed through a plastic injection molding process. For example, a chassis and/or chassis cover may be formed from plastic components, rather than metal components. The plastic components may be strengthened with support ribs or the like, to provide additional rigidity to the plastic material. Additionally, a foundation support, such as a metal plate, may be attached to the chassis and/or chassis cover to further enhance the rigidity of the assembly. By enhancing the rigidity of the assembly, without requiring components constructed of rigid materials, such as metals and metal alloys, the toothbrush may be created with less expensive materials, such as plastics, without reducing the rigidity of the toothbrush. Additionally, by using materials such as plastics that can be injection molded, some machining processes (such as drilling, tapping, and/or milling) may be omitted. As an example, rather than tapping treads in metal, the fasteners for the chassis and chassis cover may be off the shelf screws or nuts.

The toothbrush may further include mountings to connect the internal components of the toothbrush to an exterior housing. The mountings may include a dampening or compressible material, such as an elastomeric material or the like. The mountings may reduce vibration from the internal components, such as the drive assembly, from being transmitted to the housing. Accordingly, the user may feel minimal to no vibration when gripping the exterior of the toothbrush, even as the drive shaft and output shaft are rotating and vibrating to move the brush head. This may enhance the user's grip on the toothbrush, assisting the user in maneuvering the toothbrush inside his or her mouth, as well as enhance the user experience while operating the toothbrush. In some embodiments, the toothbrush may include soft mountings such as the lip 320 of the boot seal 146, upper and lower vibration pads 438*a*, 438*b*, 444*a*, 444*b* integrally formed with the hand grip 108, front and rear isolators 150, 160, light guide 156, and end cap O-ring 414.

In some embodiments, the toothbrush may also include a motor control circuit. The motor control circuit may include a signal generator that may selectively vary one or more control signals applied to the motor. The one or more control signals may be used to vary one or more output characteristics of the toothbrush, such as the bristle vibration or rotation frequency. In one example, the signal generator may apply a pulse width modulated signal to selectively control the power applied to the motor and may increase or decrease the power as desired. As the power increases or decreases, the rotation speed (RPM) of a drive shaft of the motor may be increased or decreased, as well as the torque output by the drive shaft.

The motor control circuit may vary the control signal to maintain a constant output of the motor. For example, the toothbrush may include one or more batteries as the power source and as the battery drains (e.g., their stored charge is depleted) the frequency or speed of the brush head may be reduced. In this example, the motor control circuit may apply a control signal with a predetermined duty cycle that may increase the output of the motor. In this example, even as the battery voltage output drains, the motor output may be approximately constant. In one implementation, the circuit may compare the battery voltage against a characterization curve, and using the curve apply a pulse width modulated duty cycle to the motor to maintain a particular motor output regardless of the battery voltage. In another implementation, a sensor or pair of sensors (such as a light emitting diode emitter pair) along with an interrupter (such as a fan) may be used to measure the motor RPM directly and adjust the control signal via a feedback loop. In some embodiments, the linkage assembly may regulate the amplitude of the brush head movement, but the frequency may vary based on a voltage input to the motor. Accordingly, by varying the input to the motor, the frequency and amplitude of the bristle movement may be controlled and may be substantially constant.

Overview of the Toothbrush

Turning now to the figures, the toothbrush will now be discussed in more detail. FIGS. 1A-1E illustrate various views of the toothbrush. With reference to FIGS. 1A-1E, the toothbrush 100 may include a body 104 having a housing 106 and a hand grip 108 and a brush head 102 including a plurality of bristles 105 attached to the body 104. The brush head 102 may be removable from the body 104, which allows the brush head 102 to be replaced as the bristles 105 become worn or to allow different users to use the toothbrush 100.

The body 104 may be held by a user in his or her hand. The body 104 may have an elongated cylindrical shape that may have an upper portion that tapers towards the brush head 104. The hand grip 108 will be discussed in more detail below, but briefly, may provide a gripping surface for a user's hand and may be a softer material than the housing 106. The body 104 may include a control button 110 to activate the toothbrush 100, as well as to control one or more settings or speeds of the toothbrush 100. Additionally, an indication panel, which may include a plurality of lights or other display elements, may be viewable through the housing 106 of the body 104.

Figure 2:
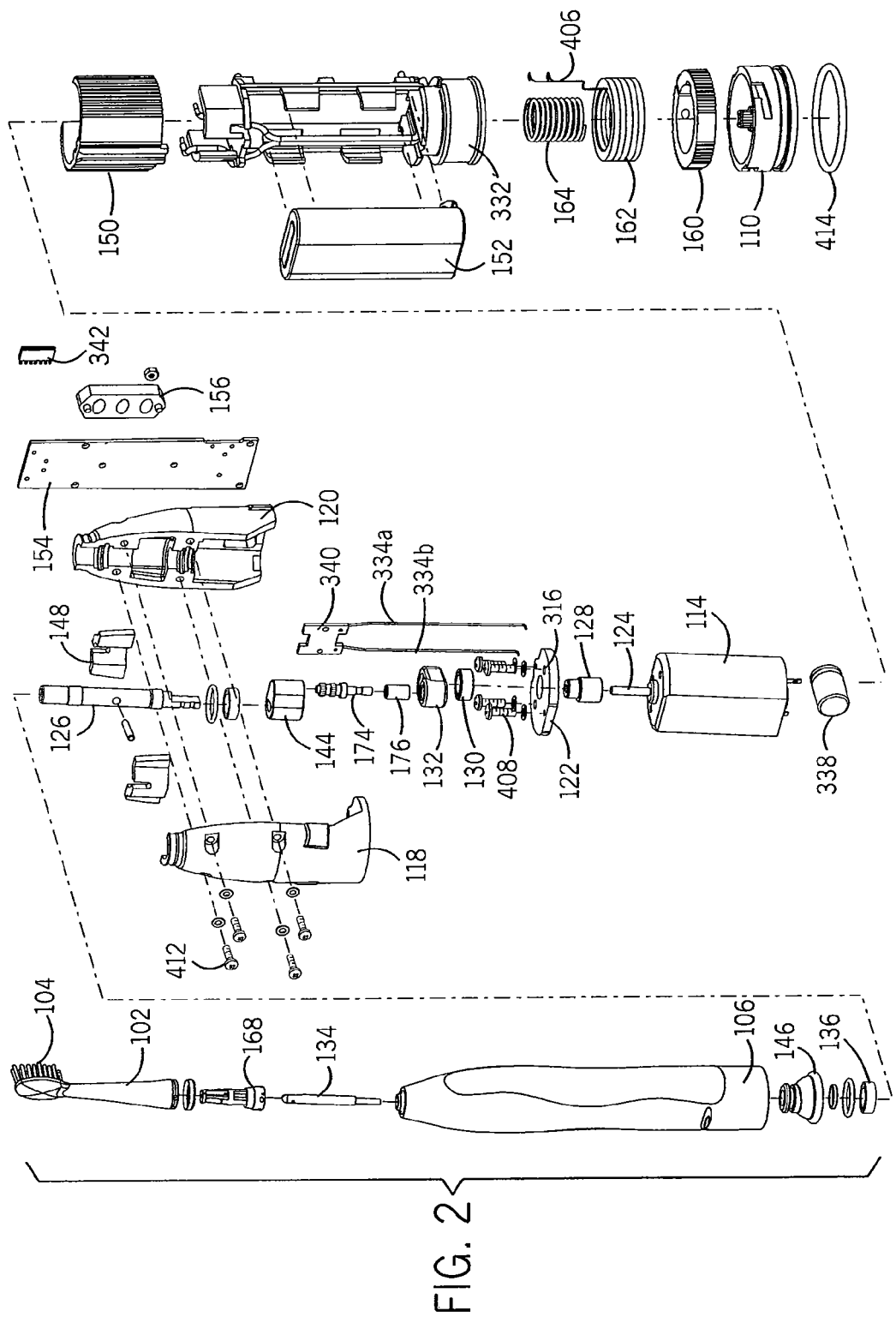
FIG. 2 is an exploded view of the toothbrush.
Figure 3A:
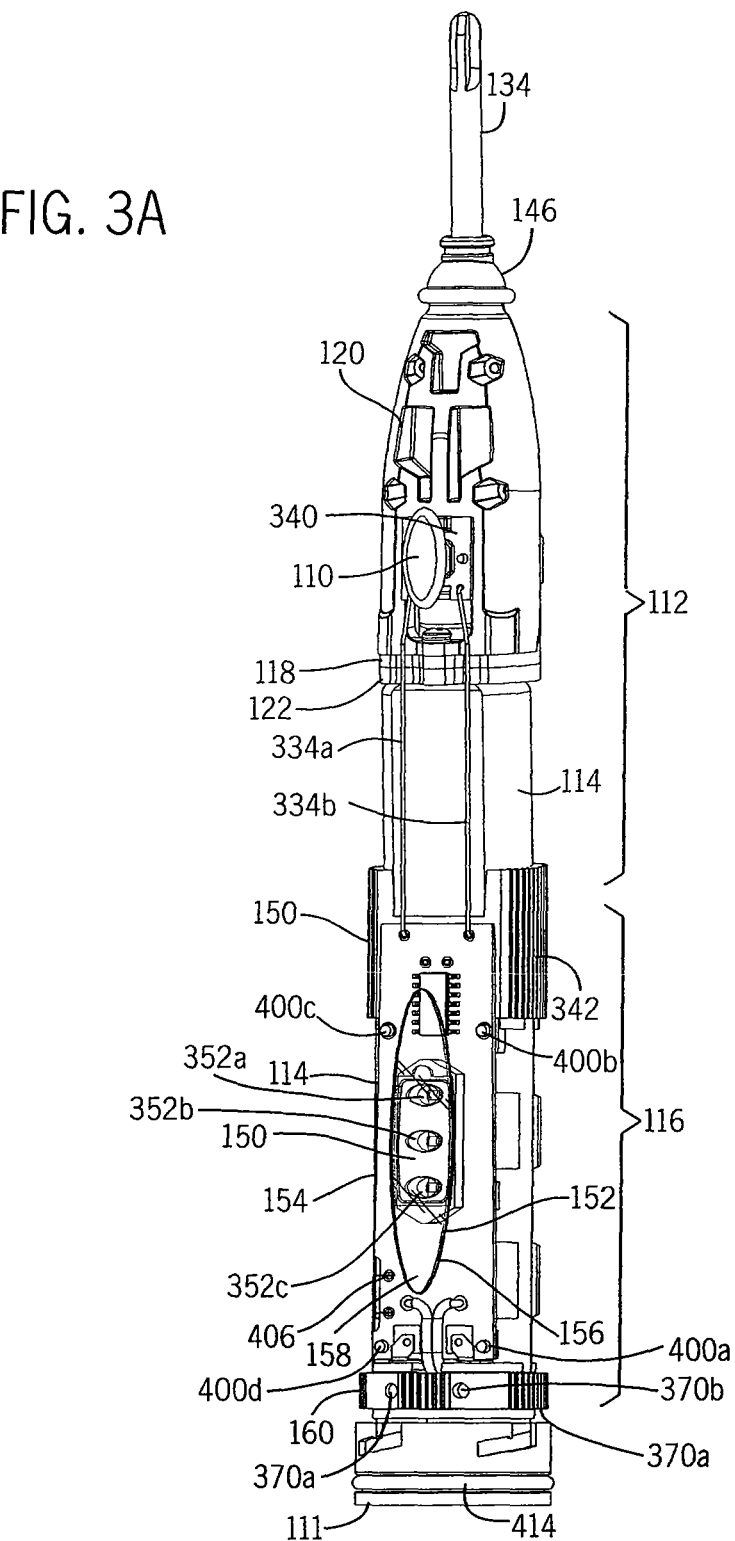
FIG. 3A is a front perspective view of the toothbrush with a housing and hand grip hidden for clarity.
Figure 3B:
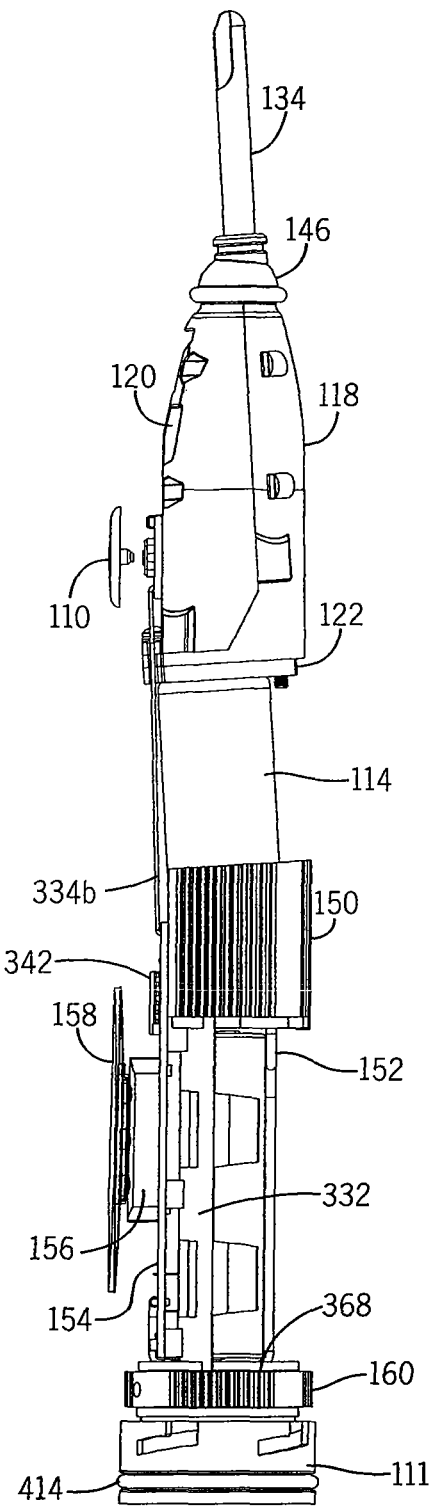
FIG. 3B is a side elevation view of the toothbrush of FIG. 3A.
Figure 3C:
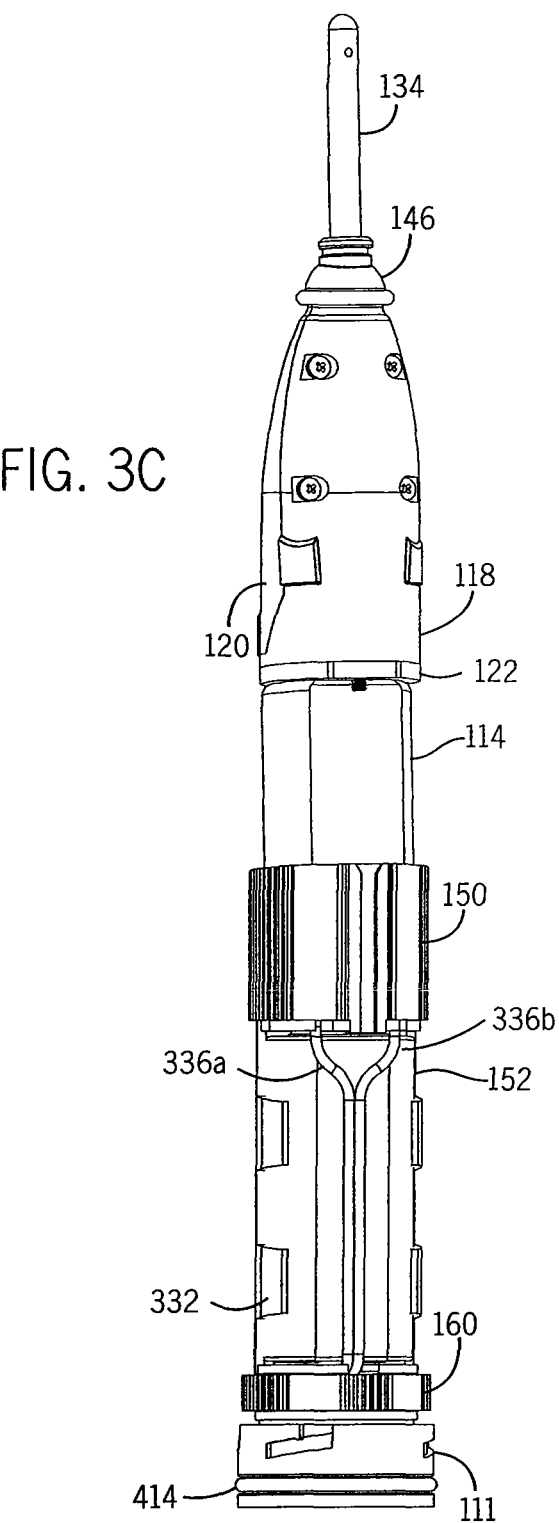
FIG. 3C is a rear elevation view of the toothbrush of FIG. 3A.

The body 104 houses the internal components of the toothbrush 100. FIG. 2 is an exploded view of the toothbrush 100. FIGS. 3A-3C illustrate various views of the toothbrush with the housing 106 and finger grip 108 hidden for clarity. With reference to FIGS. 2-3C, the toothbrush 100 may include a drive assembly 112 and a power assembly 116. The power assembly 116 may provide power to the drive assembly 112, which may rotate a tip shaft 134 to move the brush head 102. Accordingly, the drive assembly 112 may be generally positioned above and electrically connected to the power assembly 116. Each of these components will be discussed, in turn, below.

Drive Assembly

Figure 5:
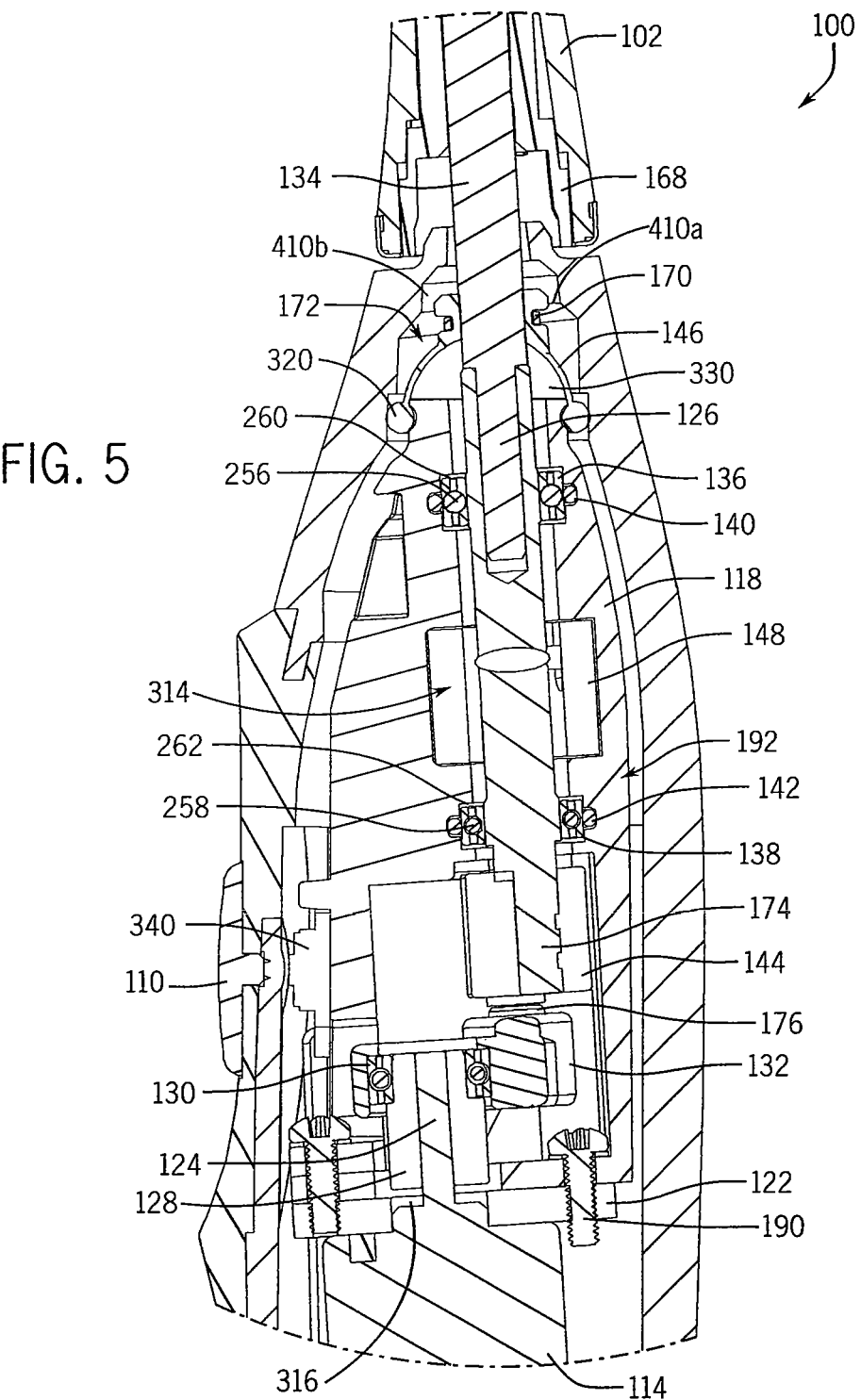
FIG. 5 is an enlarged view of the cross-section illustrated in FIG. 4.
Figure 8:
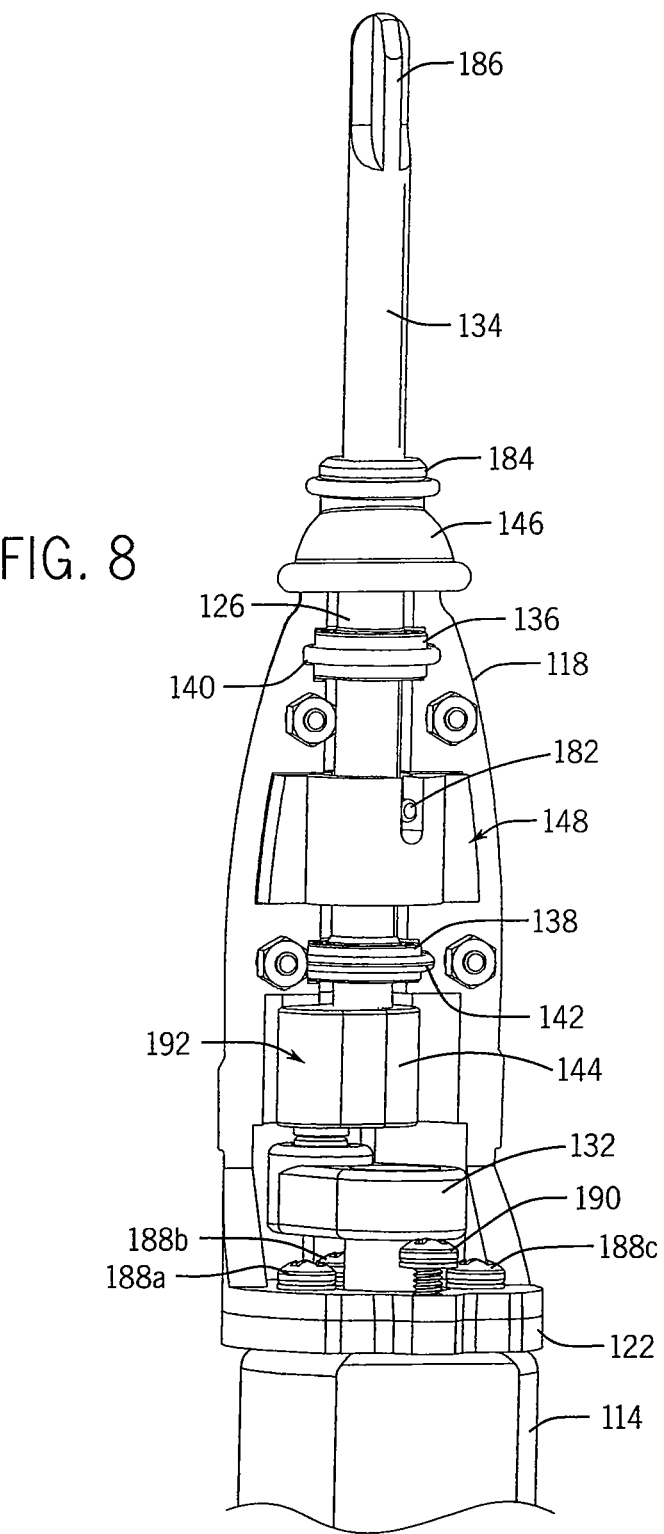
FIG. 8 is a front perspective view of the toothbrush with the housing and chassis cover hidden for clarity.

The drive assembly 112 will now be discussed in further detail. FIG. 4 is a cross-section view of the toothbrush taken along line 4-4 in FIG. 1A. FIG. 5 is an enlarged view of the cross-section view of FIG. 4. FIGS. 6 and 7 are cross-sectional views of the toothbrush taken along lines 6-6 and 7-7 in FIG. 1A, respectively. FIG. 8 is a front perspective view of the toothbrush with select features hidden for clarity. With reference to FIGS. 4-8, the drive assembly may include a motor 114, a linkage assembly 192, an output shaft 126, and the tip shaft 134. The linkage assembly 192 may act to transfer movement from the motor 114 to the tip shaft 134.

Figure 9:
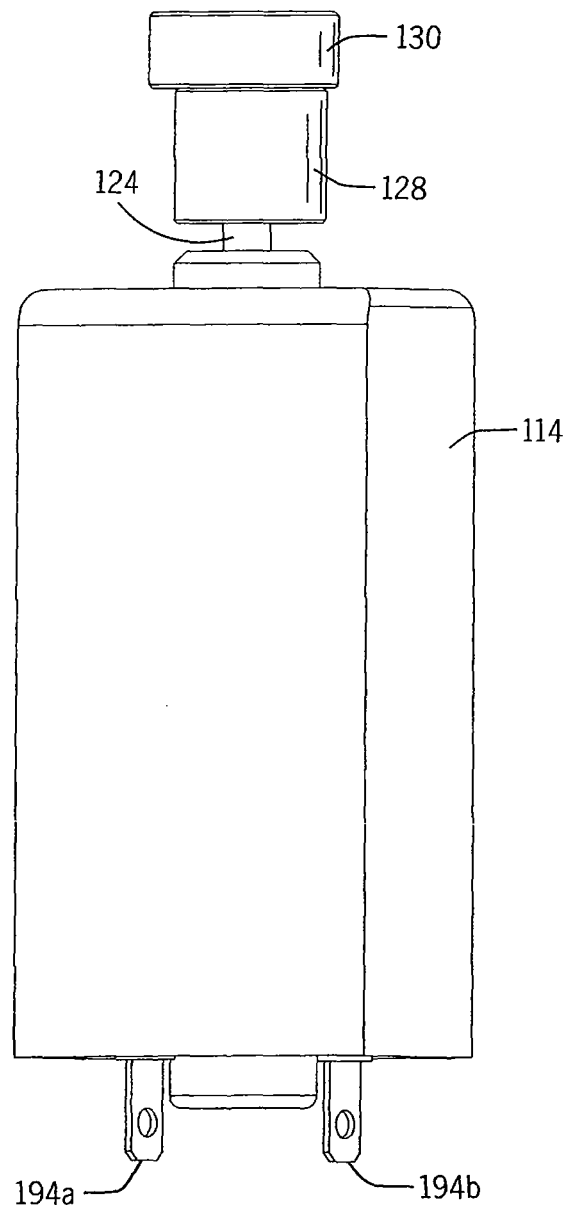
FIG. 9 is a perspective view of a portion of a drive assembly for the toothbrush.

The motor 114 translates energy or power into movement. The motor 114 includes a drive shaft 124 extending from a top surface. The drive shaft 124 is rotated by the motor 114 in response to a control signal, such as a voltage or current. FIG. 9 is a perspective view of the motor 114, eccentric, and bearing removed from the toothbrush. With reference to FIG. 9, the motor 114 may include a first terminal 194*a* and a second terminal 194*b*. The two pongs 194*a*, 194*b* extend from a bottom end of the motor 114 and provide an electrical connection between the motor 114 and the power assembly 116. The motor 114 may be a constant speed motor or may be a variable speed motor. Additionally, the motor 114 may be a direct current motor or an alternating current motor.

Figure 10A:
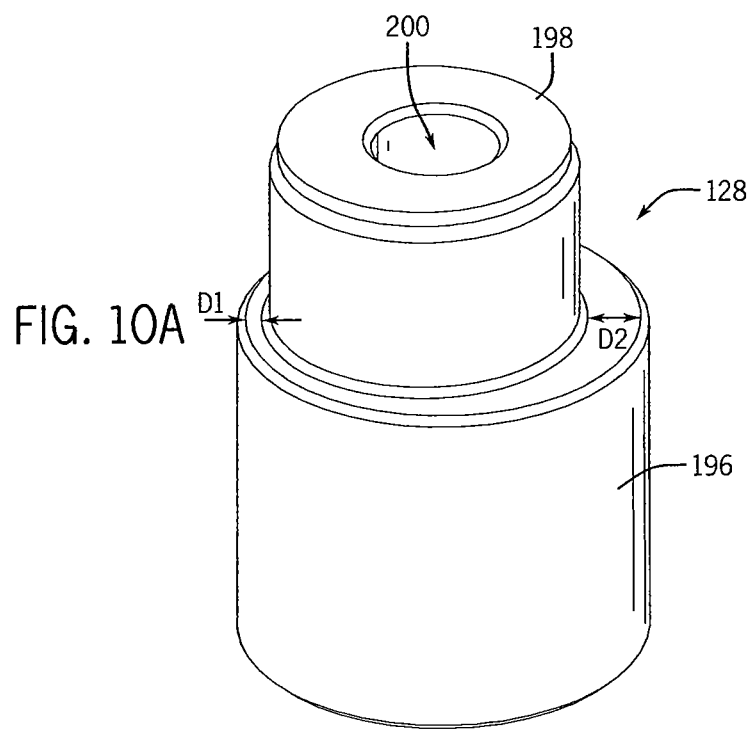
FIG. 10A is a front perspective view of an eccentric for the drive assembly.
Figure 10B:
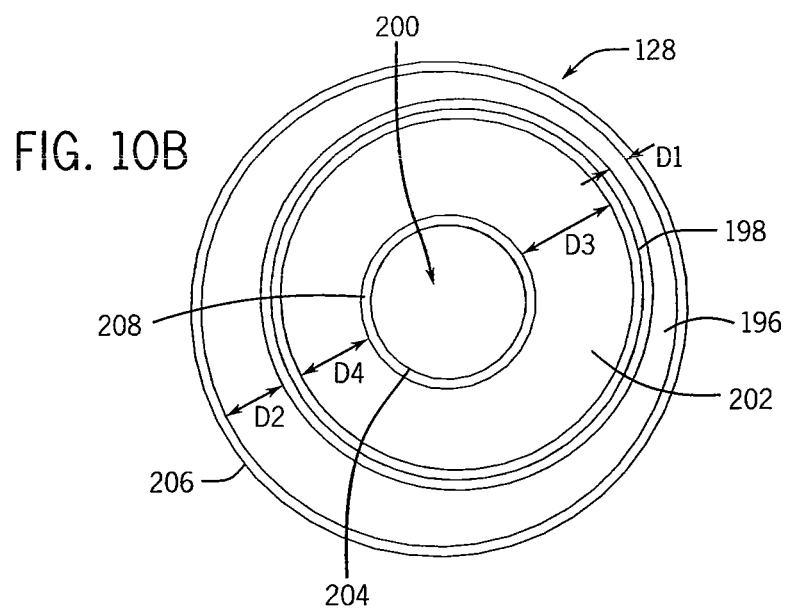
FIG. 10B is a top plan view of the eccentric of FIG. 10A.

An eccentric 128 is connected to the drive shaft 124 of the motor 114. FIG. 10A is a perspective view of the eccentric. FIG. 10B is a top plan view of the eccentric. With reference to FIGS. 10A and 10B, the eccentric 128 includes a body 196 with a hub 198 extending form a top portion of the body. The body 196 may be generally cylindrically shaped and may have a larger diameter than the hub 198, such that a portion of a top surface 202 of the body 196 may form a ledge or step between the body 196 and the hub 198.

The hub 198 extends from the body 196 and has a generally cylindrical shape as well. However, the hub 198 may be asymmetrically positioned on the body 196. For example, with reference to FIG. 10B, a first portion of the hub 198 may be positioned at a distance D1 from a terminal edge 204 of the top surface 202 of the body 196 and a second portion of the hub 198 may be positioned at a distance D2 from the terminal edge 204, where the second distance D2 is larger than the first distance D1.

A shaft aperture 200 is defined through both the hub 198 and the body 196. The shaft aperture 200 may be generally sized to receive the drive shaft 124 of the motor 114. With reference again to FIG. 10B, the shaft aperture 200 may be off-center from a centerline of the hub 198, as well as off-center from a centerline of the body 196. For example, the hub 198 may have an outer edge 206 and an inner edge 208, the inner edge 208 defining the diameter of the shaft aperture 200. On a first side of the hub 198, the outer edge 206 and the inner edge 208 may be separated by a third distance D3 and on a second side of the hub 198, the outer edge 206 and the inner edge 208 may be separated by a fourth distance D4, where the third distance D3 is larger than the fourth distance D4.

The offset nature of both the shaft aperture 200 and the hub 198 as it is positioned on the body 196 defines an asymmetrically distributed weight, which changes rotation characteristics of the eccentric 128. Further, the variation in material on either side of the shaft aperture 200, and between the position of the hub 198 on the body 196, may function as a counterweight to balance the weight of a ball bearing, discussed in more detail below.

With reference now to FIGS. 11A and 11B, the components of the linkage assembly 192 will be discussed in more detail. The linkage assembly 192 may include a link coupler 132, a rocker 144, a linkage ball bearing 130, a drive pin 174, and a bushing 176. The linkage ball bearing 130 and the eccentric 128 may connect the other components of the linkage assembly 192 to the drive shaft 124 of the motor 114, as will be discussed in more detail below.

Figure 12A:
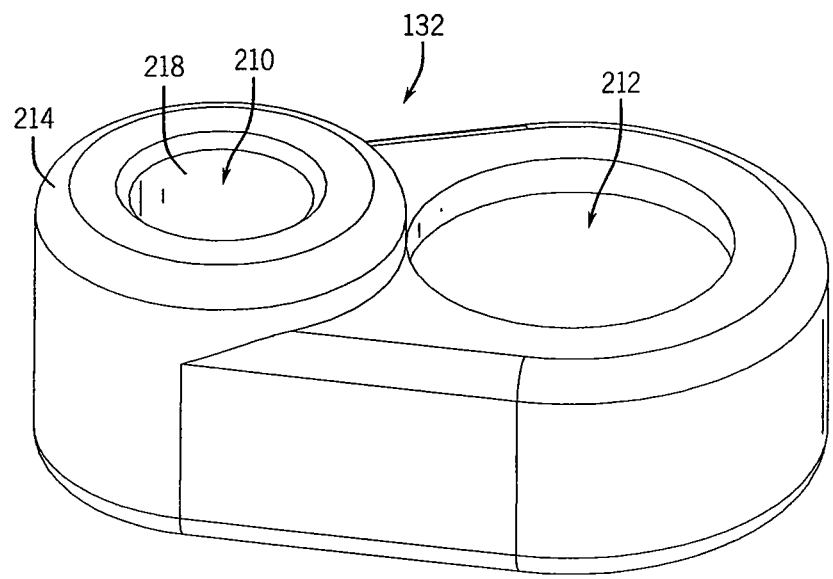
FIG. 12A is a front perspective view of a coupler of the linkage assembly.
Figure 12B:
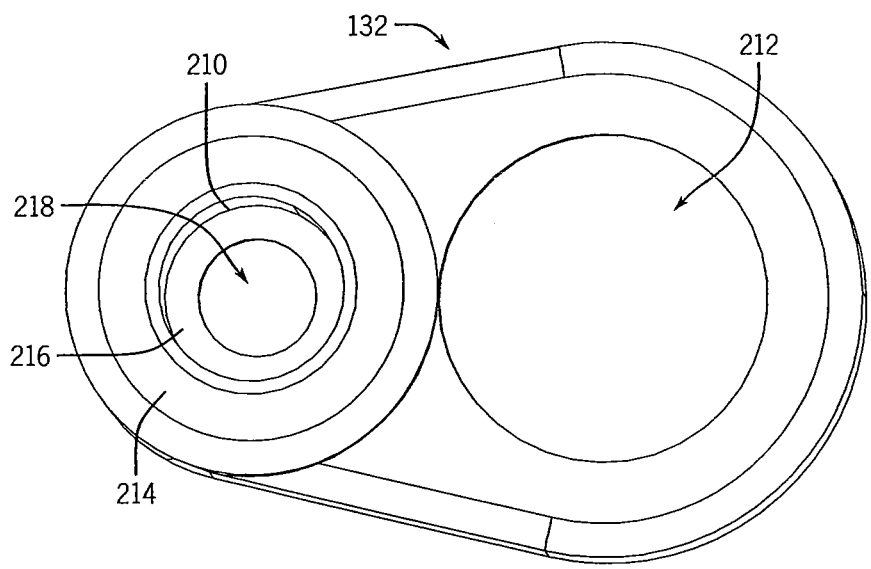
FIG. 12B is a top plan view of the coupler of FIG. 12A.

The link coupler 132 connects the eccentric 128 to the other components of the linkage assembly 192. With reference to FIGS. 12A and 12B, the link coupler 132 defines an eccentric aperture 212 and a pin aperture 210. The two apertures 210, 212 may be generally axially aligned along their centerlines. However, in some embodiments, the eccentric aperture 212 may have a larger diameter than the pin aperture 210. Additionally, the pin aperture 210 may have a longer length than the eccentric aperture 212. For example, the link coupler 132 may include a raised lip 214 through which the pin aperture 210 is defined.

With reference to FIG. 12B, the pin aperture 210 may also vary in diameter along its length. For example, a shelf 216 may extend inwards from interior wall 218 defining the pin aperture 210. The shelf 216 may reduce the diameter of the pin aperture 210 on a bottom surface of the link coupler 132.

Figure 13:
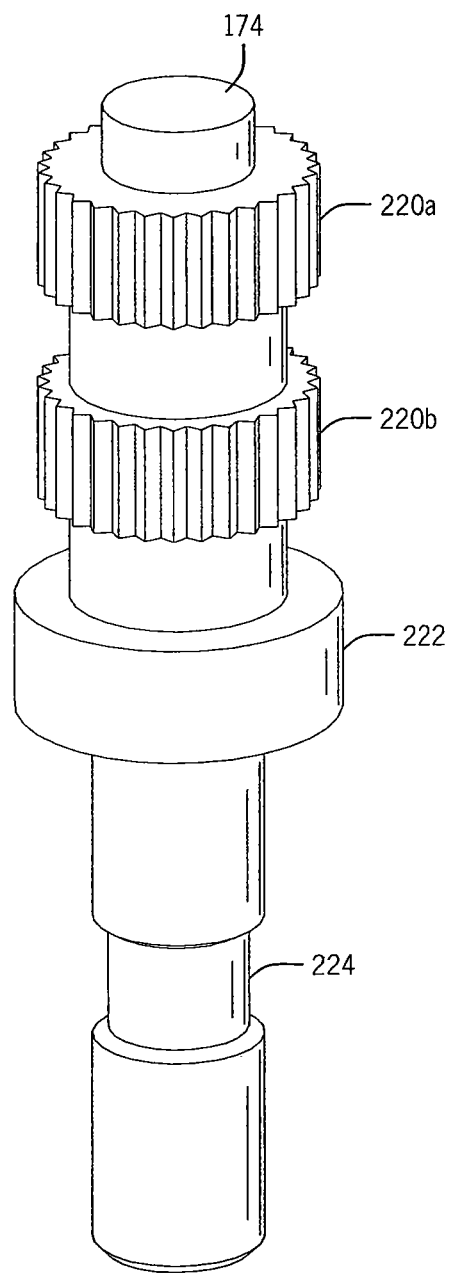
FIG. 13 is a front perspective view of a drive pin of the linkage assembly.

The drive pin 174 connects the link coupler 132 and the rocker 144 via the bushing 176. FIG. 13 is a front perspective view of the drive pin. The drive pin 174 may be an elongated member and may include one or more keying features. For example, the drive pin 174 may include two sets of splines 220a, 220b. The splines 220a, 220b may be defined on an upper portion of the drive pin 174 and may be spatially separated from each other. In one embodiment, the splines 220a, 220b may be define around the outer surface of the drive pink 174 and may extend outwards from the surface of the drive pin 174 to define recesses therebetween. A flange 222 may be positioned beneath the second set of splines 220b towards a middle portion of the drive pin 174. Additionally, the drive pin 174 may include an annular groove 224 along a bottom portion. The keying features, such as the splines 220a, 220b and annular groove 224 may be configured to attach the drive pin 174 to components of the linkage assembly 192 and may be varied as desired.

The rocker 144 connects the drive pin 174 and the output shaft 126. FIGS. 14A-14D illustrate various views of the rocker 144. The rocker 144 may be a generally oblong member and include a shaft aperture 226 defined therethrough. The shaft aperture 226 may be "D" shaped and may be defined by a straight wall 238 and a curved wall 240. The shaft aperture 226 may extend between a top surface 242 and a bottom surface 230 of the rocker 144. With reference to FIGS. 14C and 14D, a first ledge 228a and a second ledge 228b may extend inwards from the curved wall 240 towards the straight wall.

Figure 14A:
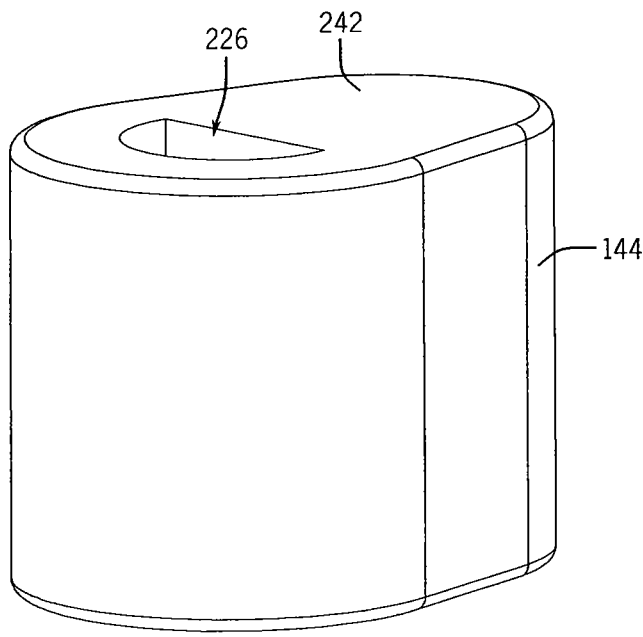
FIG. 14A is a front elevation view of a rocker of the linkage assembly.
Figure 14B:
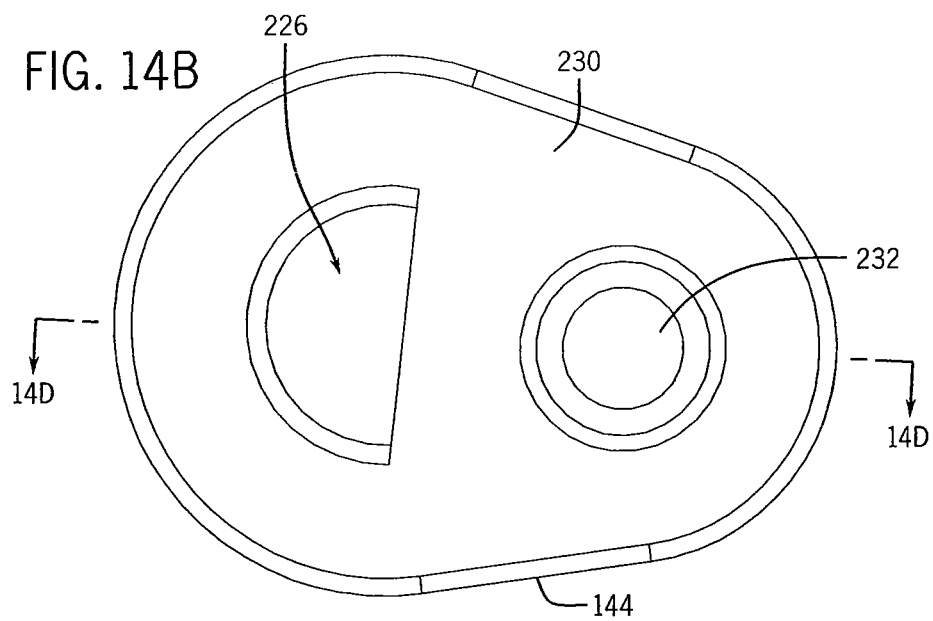
FIG. 14B is a bottom plan view of the rocker of FIG. 14A.
Figure 14C:
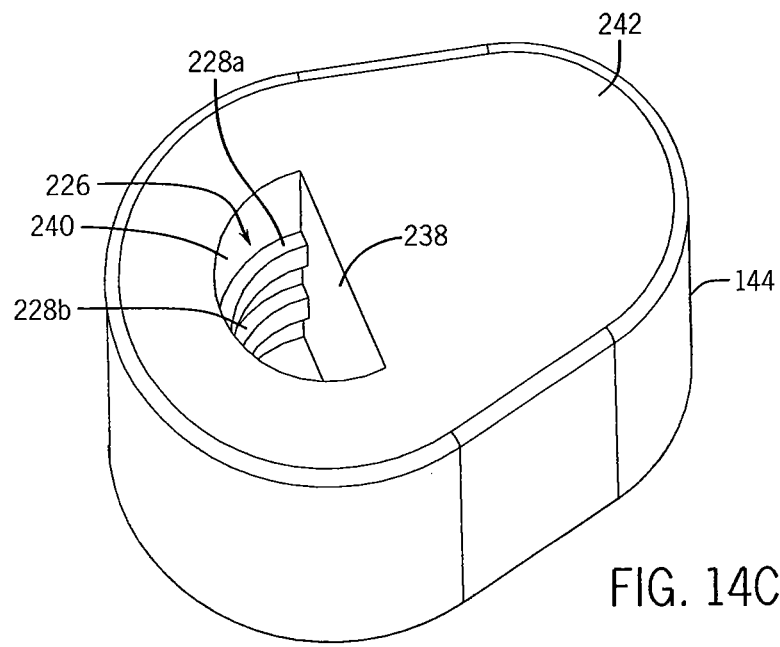
FIG. 14C is a top perspective view of the rocker of FIG. 14A.
Figure 14D:
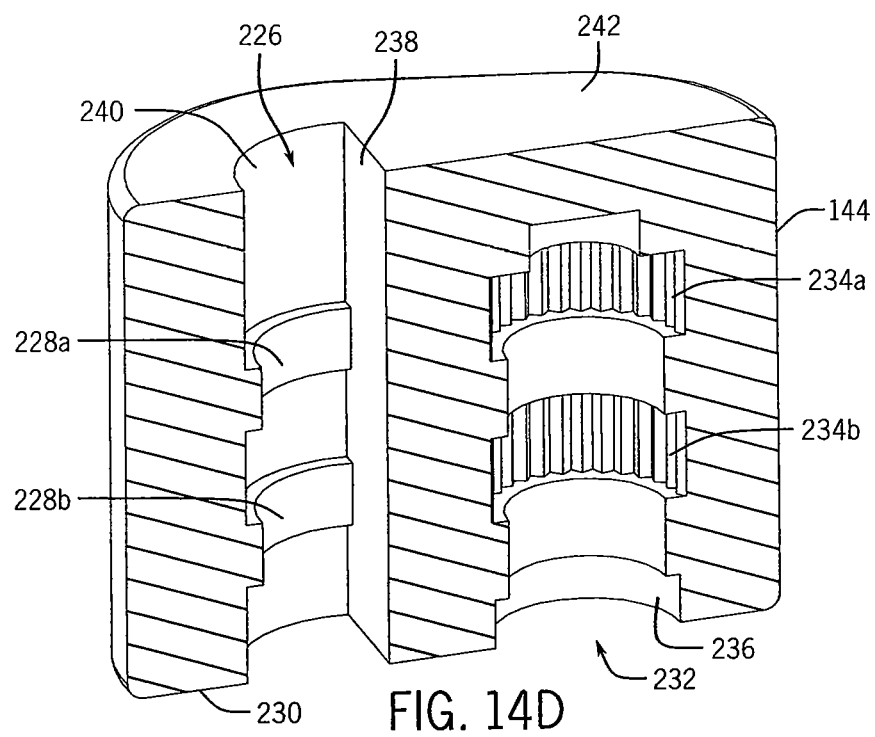
FIG. 14D is a cross-section of the rocker taken along line 14D-14D in FIG. 14B.

With reference to FIGS. 14B and 14D, a pin cavity 232 may be defined through the rocker 144. The pin cavity 232 may have an opening defined on the bottom surface 230, but may terminate prior to reaching the top surface 242. In other words, the pin cavity 232 may not extend through the entire length of the rocker 144. The pin cavity 232 may vary in diameter along its length and may include keying features to connect to the drive pin 174. For example, splines 234a, 234b may be defined on the walls defining an upper portion of the pin cavity 232 and a flange opening 236 may be define the opening of the pin cavity 232. The flange opening 236 may have a larger diameter than other portions of the pin cavity 232.

The shaft aperture 226 and the pin cavity 232 may be dimensioned to closely match the shapes and dimensions of the output shaft 126 and drive pin 174, respectively. In some embodiments, the rocker 144 may be formed by an insert molding process. In these examples, the output shaft 126 and the drive pin 174 (or other components to be connected to the rocker 144) may be positioned within a mold and then at least partially encapsulated by an injected material, such as plastic, that may form the rocker 144. In these embodiments, the rocker 144 may be formed around the output shaft 126 and the drive pin 174. Thus, as shown in FIG. 14D, the pin cavity 232, splines 234a, 234b and flange opening 236 may directly correspond to features defined on the drive pin 174. Similarly, the shaft aperture 226 and the ledges 228a, 228b and walls 238, 240 may directly correspond to features on the output shaft 126.

By using an insert molding process, or otherwise forming the rocker 144 to directly correspond to the dimensions and shapes of the linkage components to which it connects, the linkage assembly 192 may be more easily manufactured as the accuracy for connecting the rocker to the select components may be improved. Additionally, the direct correspondence in the rocker 144 to the components it connects to may reduce the likelihood that the joint may become loose or develop slop over time, which could reduce the effectiveness of the linkage, as well as create additional noise.

Figure 15:
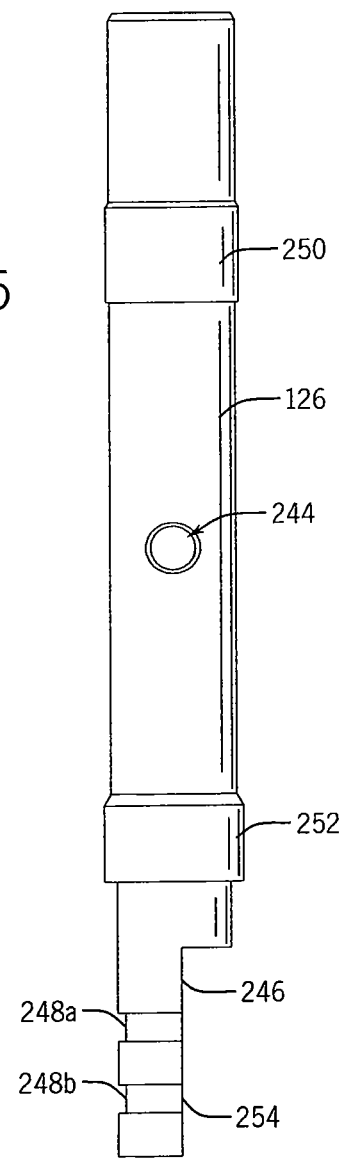
FIG. 15 is a front elevation view of an output shaft of the drive assembly.

The output shaft 126 extends from the rocker 144 to connect to the tip shaft 134. In some examples, the output shaft 126 and the tip shaft 134 may be formed as a single-component. However, in embodiments such as illustrated in FIG. 3, by splitting the output shaft 126 and tip shaft 134 into two separate components, the mass moment of inertia for the output shaft is reduced, which allows for an increased frequency for a given battery voltage applied to the motor, as well. FIG. 15 is a front perspective view of the output shaft 126. With reference to FIG. 15, a bottom end of the output shaft 126 may include a keying feature 246, such as geometric cutout. In one embodiment, the keying feature 246 may define an engagement surface 254 that may be flat surface extending along a portion of a length of the output shaft 126. The output shaft 126 may further include recesses 248a, 248b defined on a portion of the keying feature 246. The recesses 248a, 248b may extend around a portion of an outer surface of the output shaft 126 may but may terminate prior to extending into the engagement surface 254.

A dowel aperture 244 may be defined through a width of the output shaft 126. Additionally, the output shaft 126 may include one or more bearing sleeves 250, 252. The bearing sleeves 250, 252 may be portions of additional material extending from the outer surface of the output shaft 126. In some embodiments, the bearing sleeves 250, 252 may be integrally formed with the output shaft 126 and may be areas having a larger diameter than the outer portions of the output shaft.

With reference to FIGS. 2 and 5, two or more ball bearings 136, 138 may be connected to the output shaft 126. The ball bearings 136, 138 may be spaced apart from one another and each include two races 260, 262 enclosing a plurality of balls 256, 258. The balls 256, 258 are configured to travel around and rotate around the races 260, 262.

Figure 16:
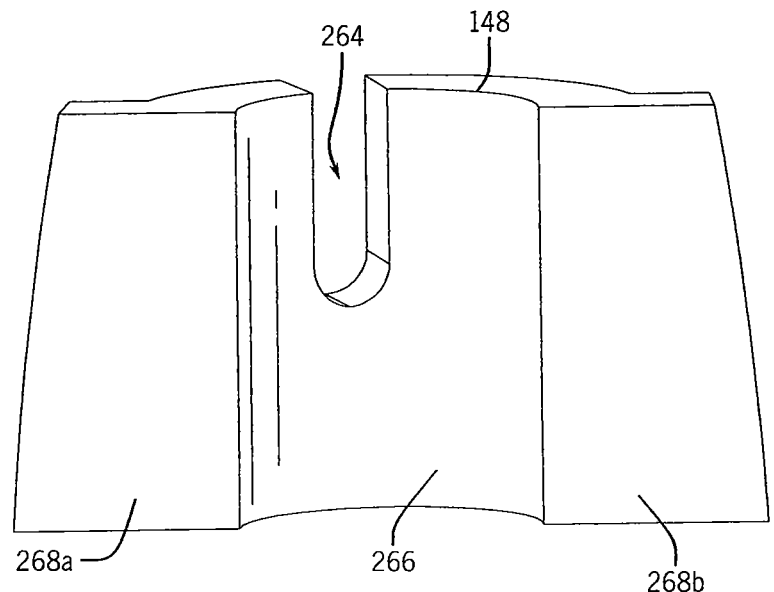
FIG. 16 is a perspective view of a bumper of the toothbrush.

In some embodiments, the toothbrush 100 may include one or more bumpers 148 connected to the output shaft 126. FIG. 16 is a front elevation view of a bumper. With reference to FIGS. 2 and 16, each bumper 148 may include a curved wall 166 with flanges 268a, 268b extending from either side of the curved wall 166. Additionally, a groove or channel 264 may be defined from a top surface of the curved wall 166 downward towards the bottom surface, terminating around a midpoint of the curved wall 166. Each bumper 148 may be substantially similar to each other and may be configured to be connected to each other to surround at least a portion of the output shaft 126. In implementations where the bumpers 148 may be substantially the same, the tooling costs for the toothbrush may be reduced, as both bumpers may be created in the same equipment. However, in other embodiments, the bumpers may be different from one another or the bumper 148 assembly may be a single bumper having a receiving aperture defined therethrough.

Figure 17:
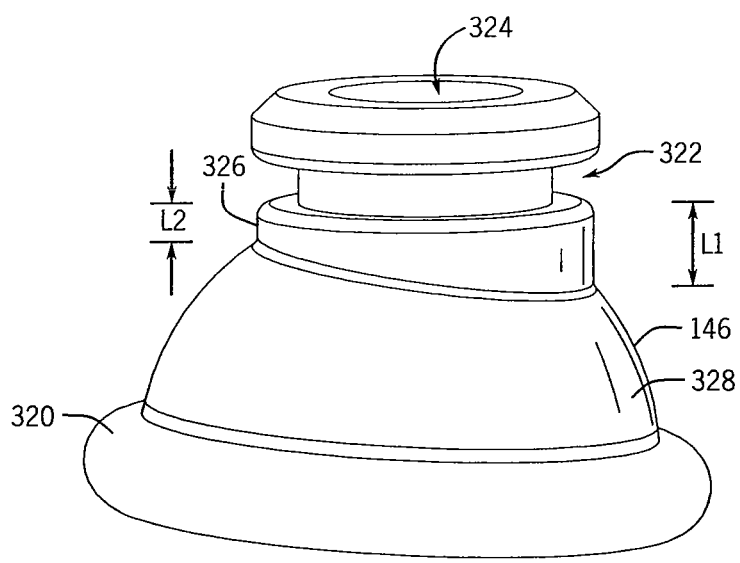
FIG. 17 is a front elevation view of a boot seal of the toothbrush.

The toothbrush 100 may also include a sealing member positioned at a joint connecting the output shaft 126 and the tip shaft 134. FIG. 17 is a front perspective view of a boot seal. With reference to FIGS. 3B, 5, and 17, the boot seal 146 is a sealing member that may be formed of a deformable material. In some embodiments, the boot seal 146 may include a skirt 328 that extends outwards and downwards to define a boot cavity 330. A terminal edge of the skirt 328 may define a lip 320. The lip 320 may include rounded edges, similar to an O-ring.

With reference to FIG. 17, a seat 326 may extend from a top portion of the skirt 328 and an annular groove 322 may be defined around a top portion of the seat 326 of the boot seal. The annular groove 322 may be defined at an angle such that a length between the annular groove 322 and the top surface of the skirt 328 on a first side of the boot seal may vary from a second side. For example, with reference to FIG. 17, a first side of the seat 326 beneath the annular groove 322 may have a first length L1 and a second side of the skirt 326 beneath the annular groove 322 may have a length L2, where the first length L1 is shorter than the second length L2. This difference in length may be determined based on a desired angle between the brush head 102 and the body 104. In other words, the brush head 102 may be orientated at an angle relative to the body 104 and the difference in lengths L1 and L2 may be based on the degree of angulation. In some embodiments, the body 104 may also be somewhat angled to accommodate the angle of the brush head 102 and in these embodiments, the varying lengths L1 and L2 of the boot seal 146 may help to ensure a seal between the housing 106 and the seal boot 146. It should be noted that in other embodiments, the motor and drive assembly may not tilted and the boot seal 146 may be generally symmetrically shaped.

The drive assembly 112 may further include a chassis to support the various components within the body 104 of the toothbrush 100. FIG. 18 is a front perspective view of the chassis. With reference to FIGS. 5 and 18, the chassis 118 may include a base 274 to support the chassis 118, as well as a plurality of cavities to receive the components to the drive assembly 112. Additionally, the chassis 118 may include a plurality of fastening apertures 272a, 272b, 272c, 272d defined through a sidewall and a plurality of fastening apertures 278 defined through the base 274 to receive one or more fastening members. A groove 292 may be defined around a top end of the chassis 118.

The cavities defined within the chassis 118 may generally conform to the components of the drive assembly 112. For example, a shaft cavity 270 may be formed along a length of the chassis 118 and may generally correspond to the output shaft 126. Two bearing cavities 280, 282 may be defined along a length of the shaft cavity e270. The bearing cavities 280, 282 may have a larger diameter than the shaft cavity 270. A bumper cavity 284 may be defined between the two bearing cavities 280, 282. The bumper cavity 284 may have a larger diameter than the bearing cavities 280, 282. Additionally, the bumper cavity 284 may be a cylindrical portion 388 and a flange portion 290, whereas the bearing cavities 280, 282 may be generally cylindrical.

A linkage cavity 286 may be defined beneath the second bearing cavity 282. The linkage cavity 286 may generally conform to the shape of the linkage assembly 192, and may allow movement of the rocker 144 and link coupler 132. In other words, the linkage assembly 192 may be configured to define a spacing gap between movable components of the linkage assembly 192 and the walls of the cavity.

Figure 19B:
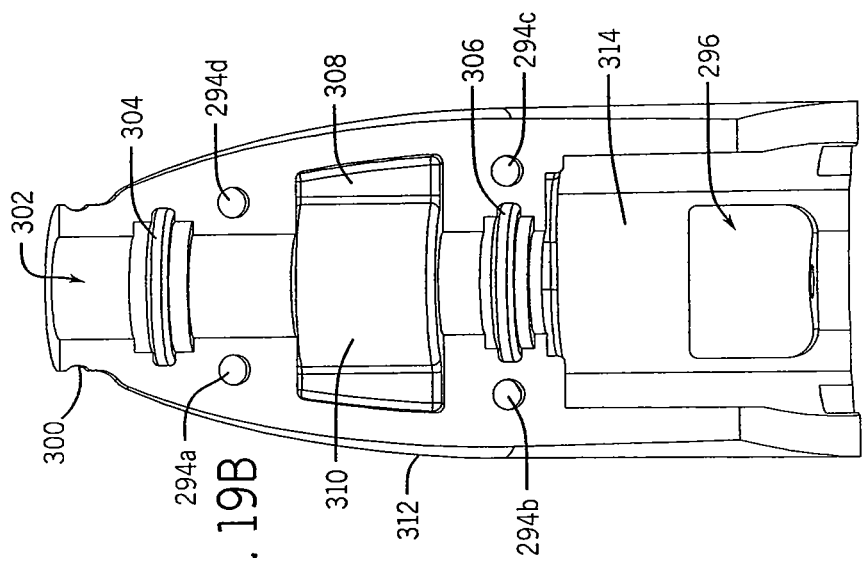
FIG. 19B is a rear elevation view of the chassis cover of the toothbrush.
Figure 19A:
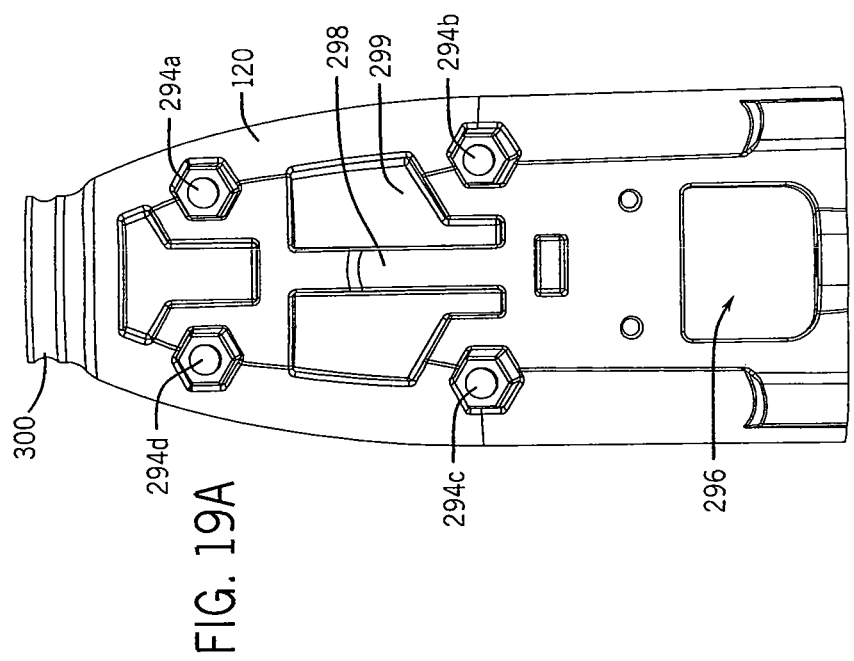
FIG. 19A is a front elevation view of a chassis cover of the toothbrush.

A chassis cover 120 may connect to the chassis 118 to enclose select components of the drive assembly 112. With reference to FIGS. 19A and 19B, the chassis cover 120 may include a plurality of fastening apertures 294a, 294b, 294c, 294d defined through a front face of the chassis cover 120. Additionally, the chassis cover 120 may define a cover aperture 296, which may be defined on a bottom portion of the chassis cover 120. In some embodiments, the cover aperture 296 may be omitted and the linkage assembly may be enclosed within the chassis and chassis cover. The chassis cover 120 may further include a groove 300 extending around an outer surface of the top portion of the cover 120.

The outer surface of the chassis cover 120 may include a plurality of ribs 298 or other strengthening members. The ribs 298 may be defined by rib recesses 299 on adjacent sides of the ribs 298. The ribs 298 provide rigidity to the chassis cover 120. The additional rigidity provided by the ribs 298 may allow the chassis cover 120 and chassis 118 to be formed out of less rigid materials. For example, in some embodiments, the chassis cover 120 may be formed out of plastic, e.g., through plastic injection molding, which may reduce costs as compared to a machine die casting component, while still providing sufficient rigidity.

With reference to FIG. 19B, similarly to the chassis 118, the chassis cover 120 may define a plurality of cavities that may receive various components of the drive assembly 112. The chassis cover 120 may define a shaft cavity 302, two bearing cavities 304, 306, a bumper cavity 308, as well as a linkage cavity 314. The cavities may be substantially similar to the cavities defined in the chassis 118 and may generally conform to one or more components of the drive assembly 112.

The bearing cavities 304, 306 may be substantially cylindrically shaped and may have a larger diameter than the shaft cavity 302. The bumper cavity 308 may be positioned between the two bearing cavities 304, 306 and may include a cylindrical portion 310 and a flange portion 312 extending from the cylindrical portion 301 and having a depth that may be less than a depth of the cylindrical portion 310. The linkage cavity 314 may be defined beneath the second bearing cavity 306 and may generally enclose the movable components of the drive assembly 112. Accordingly, as with the linkage cavity 286 in the chassis 118, when assembled, the linkage cavity 314 may define a spacing gap or distance between the moveable components and the walls of the chassis cover 120.

With reference to FIGS. 2 and 5, the chassis 118 and the chassis cover 120 may be supported by a foundation plate 122. The foundation plate 122 may be formed of a substantially rigid material, such as from one or more metals or metal alloys. In some embodiments, the foundation plate 122 may be formed of stainless steel. The foundation plate 122 may be a metal stamping or other component that my provide support and rigidity for the drive assembly 112. The foundation plate 122 may be sandwiched between the chassis 118 and the motor 114. The foundation plate 122 provides additional rigidity to the toothbrush, which allows the chassis 118 and chassis cover 120 to be formed from less rigid, and less expensive materials, such as one or more plastics or other materials, without reducing the rigidity of the assembly.

The foundation plate 122 may include a motor aperture 316 (see FIG. 2) and a plurality of fastening apertures 318 defined therein. The motor aperture 316 allows the drive shaft 124 and other portions of the motor 114 to extend through the foundation plate 122. The fastening apertures 318 may be configured to receive a plurality of fasteners therethrough. In some embodiments, the foundation plate 122 may be relatively planar and may have a diameter that generally corresponds to a diameter of the chassis 118.

Power Assembly

Figure 20B:
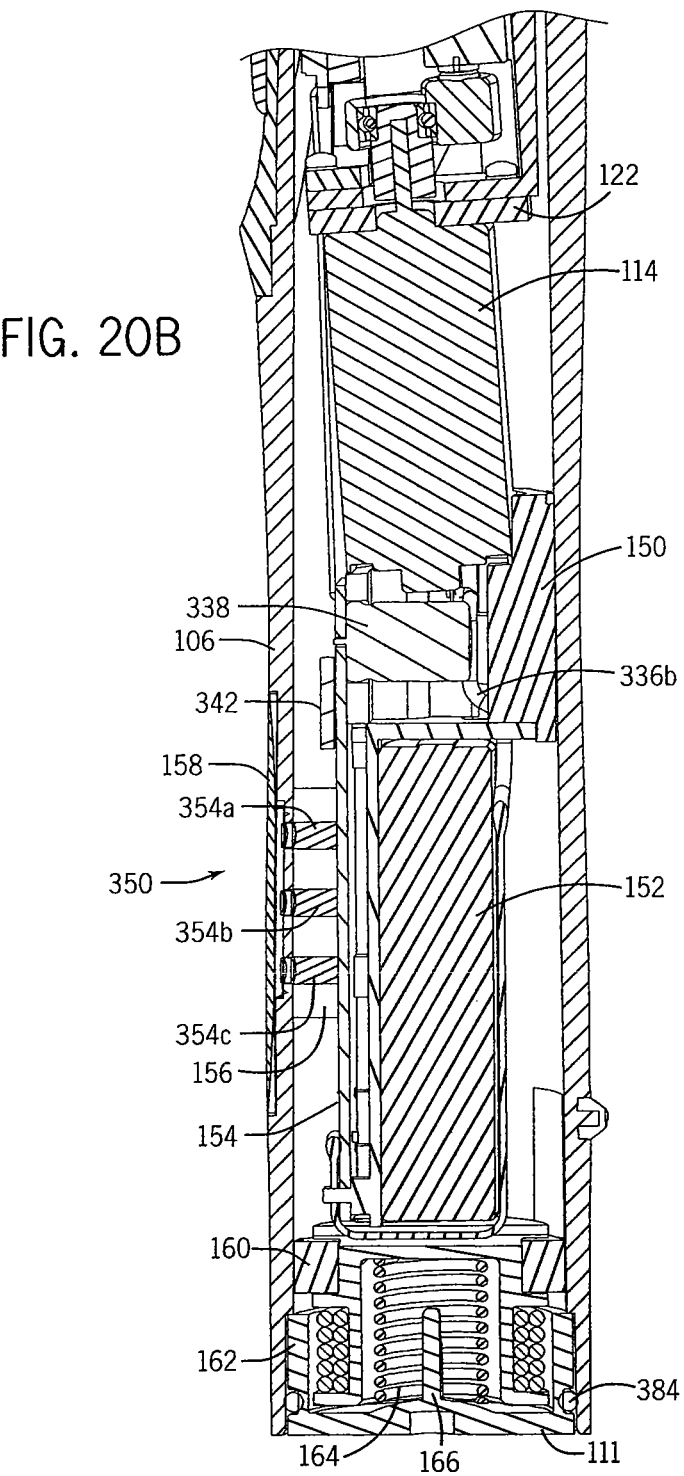
FIG. 20B is an enlarged cross-section view of the toothbrush taken along line 20A-20B in FIG. 1B.

The power assembly 116 will now be discussed in more detail. FIG. 20A is an enlarged cross section view of the toothbrush taken along line 20A-20A in FIG. 1C. FIG. 20B is an enlarged cross section view of the toothbrush taken along line 20B-20B in FIG. 1B. With reference to FIGS. 2, 3A, 4, 20A, and 20B, the power assembly 116 may include one or more batteries 152, a battery housing 332, a control circuit 154, and a charging coil 162. The power assembly 116 may provide power to the motor 114 to drive the drive shaft 124, as will be discussed in more detail below. Additionally, the power assembly 116 may include one or more isolation or dampening members that may connect one or more components of the power assembly to the housing.

The one or more batteries 152 may be rechargeable or may be single use. Additionally, the number, size, type, and capacity of the batteries 152 may be varied as desired. In embodiments where the batteries 152 may be rechargeable, the toothbrush 100 may further include the charging coil 162. The charging coil 162 may be a copper wire that may be wrapped around itself or otherwise may be configured to receive an induced current flow remotely from a power source. For example, the toothbrush 100 may include a charger (not shown) that may couple to the charging coil 162 to remotely induce a current in the charging coil 162 that may be used to provide power to the battery 152. Accordingly, the charging coil 162 may be in electrical communication with the battery 152.

The battery housing 332 may support the battery 152 within the toothbrush 100, as well as form a support or frame for other components of the power assembly 116. For example, the charge coil 162 may be wrapped around a portion of the battery housing 332. A first side of the battery housing 332 may include a plurality of clamps 402a, 402b, 402c, 402d that clamp around the battery. With brief reference to FIG. 3A, a second side of the battery housing 332 may include a plurality of prongs 400a, 400b, 400c, 400d extending outwards away from the second side of the battery housing 332.

A top end of the battery housing 332 may include two support prongs 344a, 344b. The support prongs 344a, 344b may extend vertically from the top end of the battery housing 332. Additionally, the battery housing 332 may include two annular grooves 346, 348 defined on a bottom portion. The first annular groove 346 may be configured to receive a dampening member and the second annular groove 348 may be configured to receive the charge coil 162. The battery housing 332 may further define a spring cavity 390 on a bottom portion and walls defining the annular grooves 346, 348 may surround and define the spring cavity 390.

The battery 152 and the charge coil 162 may be in electrical communication with a control circuit 154. For example, one or more wires 336a, 336b, 336c, 336d may transmit signals from the battery 152 and charge coil 162 to the control circuit 154. The control circuit 154 may include one or more electrical components, such as a control chip 342 and a capacitor 338. In some embodiments, the control circuitry 154 may be a printed circuit board or other substrate that may provide support for one or more electrical components and communication between those components.

The control circuitry 154, via the control chip 342, may selectively provide power from the battery 152 to the motor 114, as well as vary one or more functions of the toothbrush 100. The capacitor 338 may reduce electrical noise in a portion of the control circuit 154. For example, the control circuit may include a voltage step-up, where the voltage is increased from 2.4V to 3.3V and the capacitor 338 may reduce noise associated with the voltage step-up. The size of the capacitor 338 may be varied based on the size and required load of the motor 114.

The control circuitry 154 may also include a light assembly 350 that may include one or more lights or light sources (such as light emitting diodes), a light guide 156, and screen 158. The light assembly 350 may selectively activate one or more of the light sources to provide user feedback. For example, a first light 352a may be activated when the toothbrush 100 is in a first mode or speed, a second light 352b may be activated when the toothbrush 100 is in a second mode or speed, and a third light 352c may be activated when the toothbrush 100 is in a third mode or speed. Alternatively or additionally, two or more lights 352a, 352b, 352c may be activated simultaneously or in a pattern to indicate other parameters or characteristics (e.g., start mode, charge level, etc.).

The lights 352a, 352b, 352c may be optically connected to a light guide 156. The light guide 156 may transmit light emitted from the lights 352a, 352b, 352c from the light sources to the screen 158 to be displayed. The light guide 152 may include a plurality of transmission apertures 354a, 354b, 354c, with one transmission aperture for each light source. In some embodiments, the light guide 152 may be formed of a deformable or compressible material, such as rubber. In these embodiments, the light guide 152 may also absorb vibrations of the drive assembly, reducing the vibrations that may be transferred to the housing 106.

The control circuit 154 may also be in communication with a button circuit 340. The button circuitry 340 may receive user inputs from the button 110 and provide those inputs to the control circuit 154. In some embodiments, two or more communication wires 334a, 334b may transmit signals from the button circuit 340 to the control circuit 154.

The power assembly 116 may also include one or more soft mounts or dampeners. The dampeners may reduce vibrations created by the drive assembly 112 from being transmitted to the housing 106 of the body 104. With reference to FIG. 4, the toothbrush may include a first isolator 150 and a second isolator 160. The isolators 150, 160 may include a number of securing or keying features that may connect the isolators 150, 160 to various components of the toothbrush 100. The isolators 150, 160 may be formed from a compressible or deformable material that may absorb vibration and sound waves. For example, the isolators 150, 160 may be silicon or other elastomeric materials.

The first isolator 150 may be shaped as a sleeve or other hollow member. With reference to FIGS. 21A and 21B, the isolator 150 may be a hollow cylindrically shaped member and may include a plurality of ribs 356 extending from portions of the outer surface. The ribs 356 may be defined as vertical members extending longitudinally around the isolator 150. The isolator 150 may further include a flat surface 358 on one side with an aperture 364 defined therethrough and a recess 366 or cutout formed on a top surface.

The isolator 150 may further include two or more tracks 360a, 360b extending inwards from an interior surface. The tracks 360a, 360b may extend vertically along the inner surface of the isolator 150. Additionally, two or more arms 362a, 362b may extend inwards from an interior side of the flat surface 358. The arms 362a, 362b may extend further towards a center line of the isolator 150 than the tracks 360a, 360b. As will be discussed in more detail below, the isolator 150 may absorb vibrations from the drive and/or power assemblies. Additionally, the isolator 150 may also provide clocking or act as anti-rotation force for both the drive and power assemblies.

With reference to FIGS. 2, 3A, and 3B, the second isolator 160 may be similar to the first isolator 150, in that the second isolator 160 may be a sleeve or generally hollow cylindrically shaped member. The second isolator 160 may also include a plurality of ribs 368 defined an outer surface thereof. The ribs 368 may extend generally vertically along the outer surface of the isolator 160. Two or more apertures 370a, 370b may also be defined through at least one wall of the isolator 160.

The toothbrush 100 may also include a biasing member to exert a compression force against the internal components of the toothbrush 100. With reference to FIG. 20A, the toothbrush 100 may include a compression spring 164 that may act to compress the various components of the toothbrush 100 together. The compression spring 164 may be a coil spring or other resilient member.

Figure 22A:
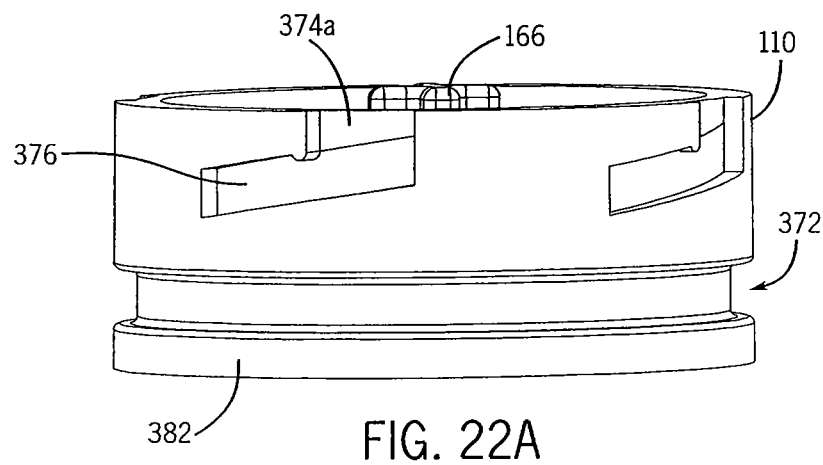
FIG. 22A is a front elevation view of a bottom cap of the toothbrush.
Figure 22B:
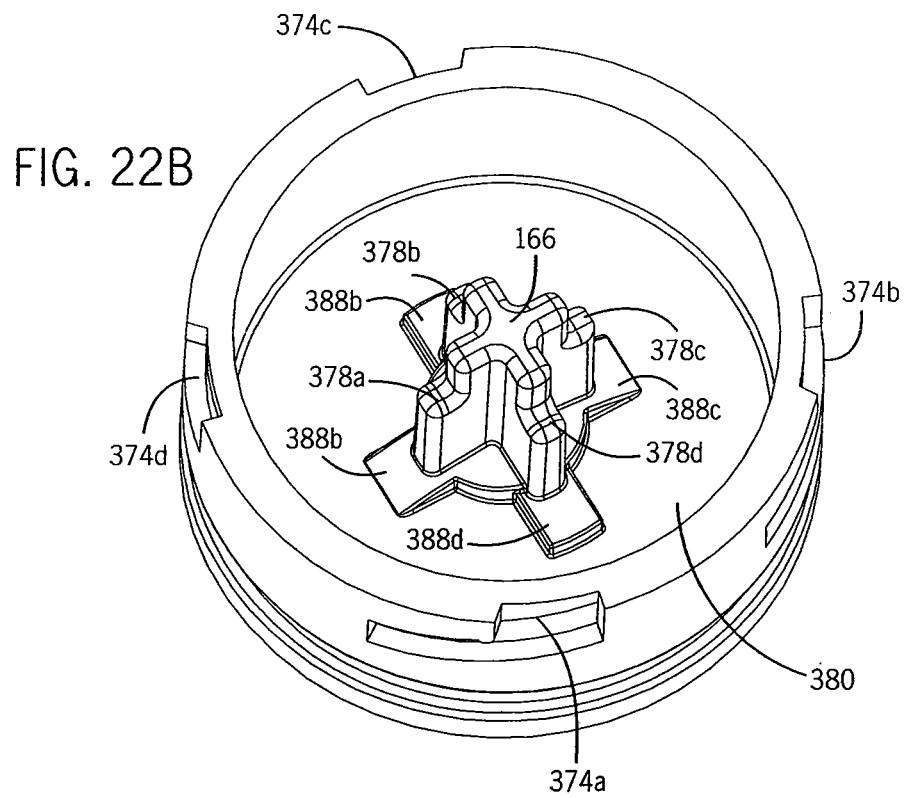
FIG. 22B is a top perspective view of the bottom cap of FIG. 22A.

A bottom cap 111 may be connected to the bottom of the housing 106. FIG. 22A is a side elevation view of the bottom cap 111. FIG. 22B is a top perspective view of the bottom cap 111. With reference to FIGS. 22A and 22B, the bottom cap 111 may be connected to the toothbrush housing 106 by any of several different mechanisms, such as, but not limited to, twist lock, snap fit, fasteners, and so on. In an exemplary embodiment, the bottom cap 111 may include one or more securing slots 374a, 374b, 374c, 374d that may correspond to one or more raised features 384 (see FIG. 20A) in a bottom of the housing 106. In this example, each securing slot 374a, 374b, 374c, 374d may include an entry groove 382 and an angled groove 376. The combination of the entry groove 382 and the angled groove 376 may form a general "L" shape, with the long leg of the "L" being formed at an angle. For example, the angled groove 376 may be angled downwards from the entry groove 382 towards a bottom end of the bottom cap 111.

The bottom cap 111 may further include a sealing groove 372 defined annularly around the outer surface of the cap 111. The sealing groove 372 may be configured to a sealing element, such as an O-ring 414. Additionally, a biasing prong 166 or bayonet may extend upwards from an interior surface 380 of the bottom cap 111. The biasing prong 166 may be shaped as an "x" or addition symbol "+". In other words, the biasing prong 166 may include a plurality of branches or arms. Each branch or arm may include a step 378a, 378b, 378c, 378d defining a ledge below a top surface of the basing prong 166. The prong branches may include a support forming a seat 388a, 388b, 388c, 388d on an interior surface of the bottom cap. A prong groove 386 may be defined on a bottom surface of the bottom cap 111, the prong groove 386 may correspond to a portion of the biasing prong 166 extending from an interior surface of the bottom cap 111.

Figure 23:
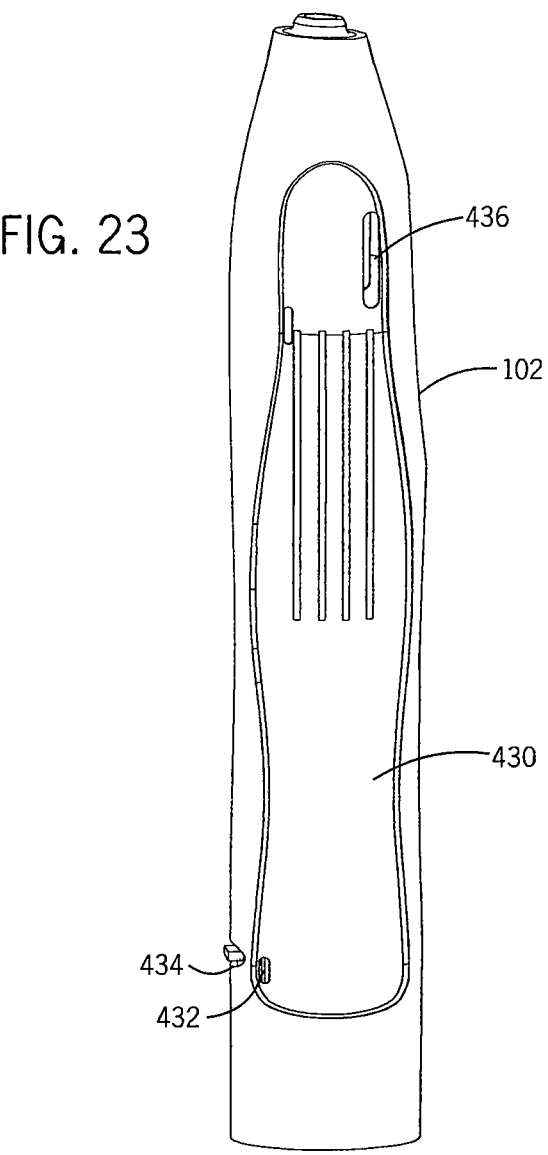
FIG. 23 is a front elevation view of the housing of the toothbrush.

The housing and handgrip will now be discussed in more detail. FIG. 23 is a front elevation view of the housing 106. The housing 106 may include two handgrip indentations 430 defined longitudinally along the housing 106. The handgrip indentations 430 may include a curvy perimeter or otherwise be shaped as desired. Generally, the handgrip indentations 430 may be recessed form the top surface of the housing 106 and may receive material that may form the hand grip 108. Accordingly, in some instances, the handgrip indentations 430 may be shaped and dimensioned to correspond to a desired shape and size of the handgrip 108.

The housing 106 may further include a plurality of ports or apertures that may be used during manufacturing to create the handgrip and one or more vibration pads, discussed in more detail below. With continued reference to FIG. 23, the two pad ports 432, 436 may be defined in the indentations 430 and may extend through the outer wall of the housing 106. Additionally, the housing 106 may include a bumper aperture 434 formed on a backside of the housing 106. The bumper aperture 434 may be used to form a bumper or protrusion for the toothbrush 100, discussed in more detail below.

Figures 24A, 24B:
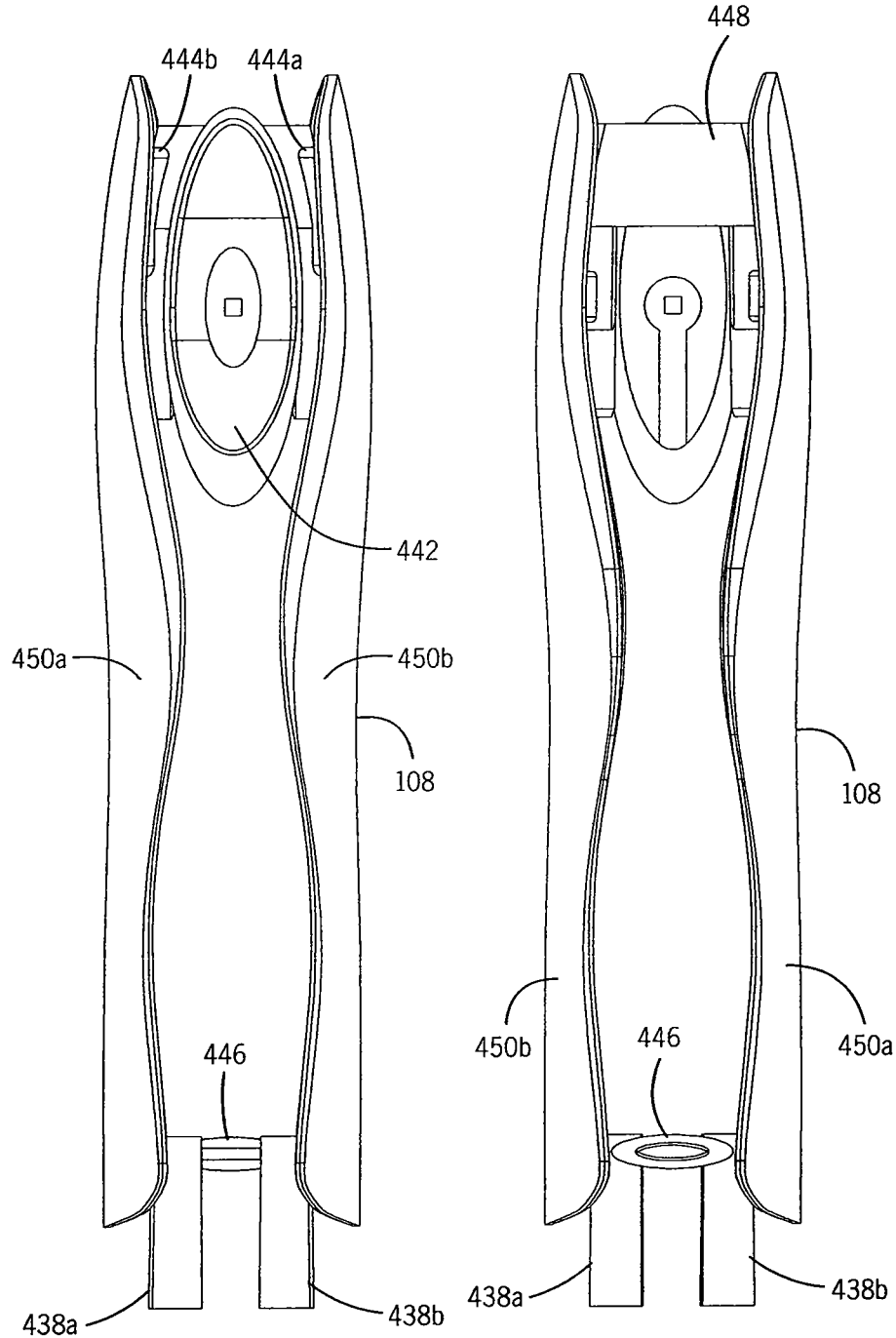
FIG. 24A is front elevation view of the handgrip of the toothbrush.
FIG. 24B is a rear elevation view of the handgrip of the toothbrush.

The handgrip 108 may be connected to the housing 106 and often may be formed through a molding process so as to be molded or formed to the housing 106. FIG. 24A is a front elevation view of the handgrip 108. FIG. 24B is a rear elevation view of the toothbrush. The handgrip 108 may be formed of a softer material than the housing 106 and may be configured to provide cushion or padding for portions of a user's hand or fingers. The handgrip 108 may include two grip portions 450a, 450b that may be positioned on an outer surface of the housing 106. The hand grip 108 may also a plurality of vibration pads 438a, 438b, 444a, 444b. The vibration pads 438a, 438b, 444a, 444b may be positioned between the housing and one or more internal components of the toothbrush 100. The pads 438a, 438b, 444a, 444b may be configured to conform to the housing 106 or other one or more components of the toothbrush 100 received in the housing 106.

The handgrip 108 may include a button pad 442 that may be received between the button 110 and the housing 106. The button pad 442 may be generally oval shaped and may include an aperture defined therein for providing a connection pathway for the button 110 and the button circuit 340.

As will be discussed in more detail below, the handgrip 108 may be formed through a molding process and may be an integrally formed component. In these embodiments, the handgrip 108 may include a bridge 448 element that may connect the upper pads 444a, 444b. The bridge 448 may be a generally curved rectangular surface that may span between both pads 444a, 444b.

The handgrip 108 may also include a rolling bumper 446. The bumper 446 may help to prevent the toothbrush 100 from rolling around on a flat surface, e.g., when the user sets the toothbrush on a countertop. In these embodiments the bumper 446 may be a protrusion that extends from the housing 106.

Assembly of the Toothbrush

The various components of the toothbrush 100 may be interconnected together and received into the housing 106 and brush head 102. With reference to FIG. 20A, starting from the bottom up, the compression spring 164 may be received around the biasing prong 166 and a portion of the compression spring 164 may be seated on the top surface of the seats 388a, 388b, 388c, 388d of each branch of the prong 166. An O-ring 394 may be received in the annular groove 348 of the bottom cap 111. The compression spring 164 and a portion of the biasing prong 166 may be received into the spring cavity 390 in the battery housing and push against a top wall 392 of the spring cavity 390. It should be noted that when the bottom cap 111 is secured to the housing 106, the compression spring 164 may be at least somewhat compressed and exert a force against the battery housing 332, which may compress the various components of the toothbrush 100 towards one another, reducing rattling between components due to slop or space between the components.

The bottom cap 111 may be locked into position inside the housing 106 as the raised features 384 defined on the interior surface 396 of the housing 106 may be received into the securing slots 374a, 374b, 374c, 374d and the bottom cap 111 or the housing 106 may be rotated relative to the other, to direct the raised features 384 into the angled grooves 376 on the bottom cap 111. Once the raised features 384 are positioned in the angled grooves 376, the bottom cap 111 may be have to turned or twisted in order to be removed from the housing 106. When the bottom cap 111 is connected to the housing 106, the O-ring 384 may seal against the interior surface of the housing 106.

With continued reference to FIG. 20A, the charge coil 162 wraps around the second annular groove 348 defined on the battery housing 332. The groove 348 and specifically the walls bordering the top and bottom of the groove 348 help to retain the charge coil 162 in position. An insulator 404 may wrap around the outer surface of the charge coil 162, to insulate the charge coil. Similarly, the rear isolator 160 is received around the first annular groove 346 in the battery housing 332 and positioned above the charge coil 162 (but separated by the top wall 394 bordering the groove 348. The rear isolator 160 may have a thickness sufficient to engage the interior surface 396 of the housing 106.

In some embodiments, the rear isolator 160 may be pressed against the housing 106 and may be caused to deform slightly in order to fit between the battery housing 332 and the housing 106. In other words, the thickness of the rear isolator 160 may be slightly larger than the distance between the groove 346 of the battery housing 332 and the interior surface 396, such that the rear isolator 106 may have to slightly deform to be received between the two. This tight fit may assist in "soft" mounting the battery housing 332 to the housing 106 and may prevent vibrations from being transmitted from the interior components of the toothbrush to the housing 106, as well as prevent rattling or a loose connection between the battery housing and the housing 106.

With reference to FIGS. 3C and 20A, the battery 152 may be received into a portion of the battery housing 332 and the battery clamps 402a, 402b, 402c, 402d of the battery housing 332 may clamp around the battery 152, securing it in place.

With reference to FIGS. 3A and 3B, the control circuit 154 may extend longitudinally along a side of the battery housing 332 opposite of the battery clamps. The prongs 400a, 400b, 400c, 400d of the battery housing 332 extend through apertures in the control circuitry 154 to connect the control circuit 154 to the battery housing 32. The prongs 400a, 400b, 400c, 400d may function as locating posts for the circuit 154 and assist in aligning the control circuit 154 within in the toothbrush assembly.

With continued reference to FIGS. 3A, 3B, 4, and 20B, the control chip 342, lights 352a, 352b, 352c, and light guide 156 may be mounted to the control circuit 154. The light guide 156 is mounted to the control circuit 154 and may substantially surround each of the lights 352a, 352b, 352c such that the apertures in the light guide 156 align with each of the lights 352a, 352b, 352c. The light guide 156 may be positioned between the housing 106 and the circuit. The screen 158 may be mounted to an outer surface of the light guide 156 and may substantially cover the light guide 156. In some embodiments, the screen 158 is connected via adhesive (not shown) or other transparent connection mechanism, such that the lights may be visible through the screen 158.

With reference again to FIG. 20A, the two support prongs 344a, 344b extending from the top surface of the battery housing 332 may be received into the isolator 150. With brief reference to FIG. 21B, in some embodiments, the prongs 344a, 344b may be received between the body or outer wall of the isolator 150 and the arms 362a, 362b. With reference again to FIG. 20A, similarly, the connection terminals 194a, 194b terminals 194a, 194b of the motor 114 may extend into the isolator 150 from the top and may also be received between the arms 362a, 362b and the outer body of the isolator 150. In this manner, the terminals 194a, 194b terminals 194a, 194b of the motor may be positioned directly above the support prongs 344a, 344b of the battery housing 332.

With reference to FIGS. 4 and 20B the capacitor 338 may extend through the aperture 364 defined through the flat surface 158 of the isolator 150 to connect to the control circuit 154. In some embodiments, the capacitor may be positioned between the two arms 362a, 362b, which may stabilize the capacitor within the isolator 150. The capacitor 338 may be connected to a backside of the control circuit 154 with its connection prongs extending through the control circuit 154.

With reference to FIGS. 3A, 3B, 4, 20A and 20B, as briefly mentioned above, the isolator 150 may be received around the motor 114, with the terminals 194a, 194b of the motor 114 being positioned between the outer wall of the isolator and the arms 362a, 362b. Additionally, a bottom surface of the motor 114 may seat on a top surface of each of the arms 362a, 362b. A first side of the motor 114 may be substantially flush with flat surface 358 of the isolator 150 and the motor 114 may be configured such that a portion of the motor 114 may extend into the recess 366 (see FIG. 21A) of the isolator 150. Additionally, as shown in FIGS. 3B and 4, the motor 114 may be angled within the isolator 150 and may lean towards the flat surface 358 of the isolator 150. In some embodiments, the flat surface 358 of the isolator may be positioned towards a front of the toothbrush, such that the motor 114 may be angled towards a front of the toothbrush 100.

The isolator 150 may connect around both portions of the power assembly 116 and the drive assembly 112. The isolator 150 may also be engaged with the interior surface of the housing 106. The engagement with the housing 106, as well as the power assembly and drive assembly, allows the isolator 150 to reduce rotation between the power assembly 116 and the drive assembly 112. Additionally, the isolator 150 may prevent vibrations from either the chassis or the motor from being transferred into the power assembly 116. For example, the material of the isolator 150 may absorb the vibrations, preventing or reducing them from being transmitted.

The isolator 150 may also transfer the load from the compression spring 164 to the motor 114. For example, the compression spring 164 exerts the compression force against the battery housing 332, which is connected to the isolator 150 and the isolator 150 may then transfer the compression force to the motor 114, pressuring the motor 114 upwards towards the brush head 102. In this example, the compression spring 164, along with the isolator 105 may reduce slop between the drive assembly and power assembly, by compressing the internal components together. The reduction in slop may reduce vibration due to components rattling or moving during operation, as well as may reduce wear and tear on the drive assembly and power assembly. For example, the compression spring 164 force (as transmitted by the isolator 150) may reduce the degrees of movement significantly. In one specific example, the chassis assembly (e.g., chassis and chassis cover) may have 1 degree of freedom once it is received into the housing 106. The compression spring 164 helps to retain the limited movement of the chassis assembly, which acts to isolate the chassis assembly from the housing, as well as reduce the likelihood that the chassis assembly will excite vibration in the power assembly.

With reference to FIGS. 3A, 4, and 20A, one or more connection wires 406 may connect the circuit 154 to the charge coil 162, which may commutatively couple the power wires 336a, 336b to the charge coil 162. The communication wires 406 may transmit power from the charge coil 162 to the control circuit 154 and then to the battery 152. The power wires 336a, 336b may connect to a bottom end of the circuit 154 and extend through a wire groove 398 formed on a bottom of the battery housing 332 between the battery 152 and the top wall of the spring cavity 394. With reference to FIGS. 3B and 20B, the power wires 336a, 336b may extend upwards along the battery 152 and may be received into apertures in the motor terminals 194a, 194b. The power wires 336a, 336b (which may transmit electrical signals to the motor). In this manner, the power wires 336a, 336b communicatively couple the control circuit 154 to the motor 114.

With reference to FIGS. 3A and 5, the foundation plate 122 seats on a top end of the motor 114 and the drive shaft 124 extends through the fastening aperture 316. The found plate 122 may have a diameter larger than the motor 114 and may extend past the edge of the top portion of the motor 114. The base 274 of the chassis 118 is positioned on the foundation plate 122 and the fastening apertures 278 on the chassis 118 may be configured to align with fastening apertures defined in the foundation plate 122. The drive shaft 124 may extend through the motor aperture 276 in the chassis 118. The foundation plate 122 adds rigidity to the mounting face of the motor 114 and joints the chassis and chassis cover together with sufficient strength that the changing load forces caused by the linkage assembly will not separate the chassis and chassis cover or create substantially deflection or lost motion.

With reference to FIGS. 5, and 6, the eccentric 128 is threaded onto the drive shaft 124, with the drive shaft 124 being inserted into the shaft aperture 200. The linkage ball bearing 130 is then received around the hub 198 of the eccentric 128. The linkage ball bearing 130 may seat on the top surface 202 of the body 196. It should be noted that the motor assembly may be angled within the housing, and as such, the bearing balls illustrated in FIG. 6 may appear as varying sizes, but in actuality may have substantially the same diameter. As described above, the eccentric 128 may include more material on one side of its body 196, e.g., the hub 198 may be offset from a centerline of the body 196 and the shaft aperture 200 may be offset from the centerline of the hub 198, such that the eccentric 128 may have more material on one side of its centerline as compared to the other side.

As briefly discussed above the asymmetrically distribution in weight defines a counterweight for the body 196 that counters the weight of the ball bearing 130 and balances the ball bearing 130 on the eccentric 128. The counterweight of the eccentric is integrally formed therewith; however, in other embodiments an external counterweight may be received onto the eccentric 128. The counterweight of the eccentric 128 balances the ball bearing 130, reducing noise as the eccentric is rotated by the drive shaft, discussed in more detail below.

With reference to FIGS. 5, 6, 8A, and 11B, the link coupler 132 is connected to the linkage ball bearing 130. For example, the linkage ball bearing 130 and the eccentric 128 may be inserted into the eccentric aperture 212 defined in the link coupler 132. In some embodiments, the motor aperture 316 may have a diameter just larger than a diameter of the bearing 130 to allow the bearing 130 and the link coupler 132 to be tightly connected together. The linkage ball bearing 130 may engage the sidewalls of the eccentric aperture 212 to connect the eccentric 128 and the link coupler 312. With reference to FIGS. 5 and 11B, in some embodiments, the ball bearing 130 may be slightly recessed from the top surface of the link coupler 132.

With reference again to FIGS. 5, 6, 8A, 11B, and 12B, the bushing 176 may be received into the pin aperture 210 of the link coupler 132. The busing 176 may extend slightly above the top surface of the raised portion 214 of the link coupler 130. The bushing 176 may be seated on the shelf 216, which provides a support platform for the bushing 176. The drive pin 174 may then be received into the bushing 174 and in some embodiments the drive pin 174 may extend through the bushing 174 to be flush with or extend beyond the pin aperture 210. The flange 222 of the drive pin 174 may sit on a top surface of the bushing 176.

With reference to FIGS. 5, 8A, 11A, and 14D the drive pin 174 may extend into the rocker 144. In one embodiment, the drive pin 174 may be inserted into the pin cavity 232. In this embodiment, the splines 220a, 220b of the drive pin 174 may be received into the complementary cavity defined in the rocker 144 such that the splines 234a, 234b defined on the rocker 144 may engage the splines 220a, 220b on the drive pin 174. The flange 222 of the drive pin 174 may seat within the flange operating 236.

As discussed above, in some embodiments, the rocker 144 may be formed through an insert molding process and may be configured to directly correspond to the shape and size of the drive pin 174. In these embodiments, the shapes of the pin cavity 232 and the features defined therein, such as the splines 234a, 234b, may be defined by the drive pin 174 itself. For example, the drive pin 174 may be positioned into a mold that may be used to create the rocker 144. With the drive pin 174 in the desired position, material (such as formable plastic or the like) may be injected into the mold in a semi-liquid form. The material may then flow around the drive pin 174 and its features and harden, creating cavities that may exactly fit around the drive pin 174. It should be noted that in these embodiments the drive pin 174 may be substantially prevented from being removed from the rocker 144 without damaging the rocker 144. Accordingly, although the pin cavity 232 is discussed as a cavity, in many instances the drive pin 174 and the rocker 144 may be substantially formed as an integral component after the molding process.

By forming the rocker 144 through an insert molding process, the connection between the rocker 144 and the drive pin 174 may have a reduced chance of becoming loose or "sloppy" over time. For example, in other connection assembles where the connection apertures are machined and then the two formed components are connected together, the apertures may not be as tight in order to allow for some machine tolerance error. The additional space between the two components may allow the two components to move relative to one another, which could create a frictional connection and wear down the materials, increasing the size of the apertures in the connection or the like.

With reference to FIGS. 5, 8A, 11A, 14D, and 15, the rocker 144 also connects to the output shaft 126. The keying feature 246 of the output shaft 126 may be received in the shaft aperture 226 defined in the rocker 144. The ledges 228a, 228b defined on the curved wall 240 of the shaft aperture 226 may be received into the recess 248a, 248b of the output shaft 126. Additionally, the engagement surface 254 of the output shaft 126 may engage against the flat wall 238 of the shaft aperture 226 of the rocker 144. In these embodiments, the rocker 144 may directly correspond to one or more features of the output shaft 126.

As described above, in some embodiments, the rocker 144 may be insert molded. In these embodiments, the output shaft 126 may also be placed in a mold used to form the rocker 144, along with the drive shaft 124. Accordingly, as the material for the rocker 144 is inserted into the mold, the material may mold to the various surfaces of the output shaft 126. This allows the shaft aperture 226, including the curved wall 240 and flat wall 238 to directly correspond to the features of the output shaft 126, reducing or eliminating any space between two output shaft 126 and the rocker 144. In other words, similarly to the drive shaft 124, the output shaft 126 may be substantially integrally formed with the rocker 144. As discussed above, the secured connection between the rocker 144 and the output shaft 126 may provide increased resistance to wear over time, as the two components may be substantially prevented from moving relative to one another, thus reducing the wear and tear on the material within the rocker 144.

With reference now to FIGS. 5 and 15, the output shaft 126 may extend upwards from the rocker 144 and connect to the tip shaft 134. The first ball bearing may be received around the tip shaft 134 and the second ball bearing 138 may be received around the output shaft 126. By having one bearing on each of the shafts 126, 134, the bearings may be connected to their respective shafts prior to the shafts 126, 134 being connected (e.g., press fit) together. For example, the first ball bearing 136 may be received around the tip shaft 134 which may then be inserted into the output shaft and the bearing may align with the bearing sleeve 250 of the output shaft 126 towards a top end of the shaft and the second ball bearing 138 may be received around the bearing sleeve 252 on a bottom portion of the output shaft 126. Additionally, each ball bearing 136, 138 may include a sealing member received around an outer portion thereof. For example, a first O-ring 140 may be received around the first ball bearing 136 and a second O-ring 142 may be received around the second ball bearing 138.

The O-rings 140, 142 received around the ball bearings 136, 138 reducing rattling in instances where the chassis and chassis cover are loose or have extra space between the ball bearings. When the fit of the chassis and chassis cover around the outer diameter of the ball bearings 136, 138 may be loose, the O-rings may extend into the extra space, tightening the connection between the chassis and the bearings. Additionally, the O-rings 140, 142 provide a uniform load around the bearings 136, 138, which helps to prevent the bearings 136, 138 from being forced into an asymmetrical shape (e.g., oblong) due to the rotation forces exerted by the output shaft 126. In other words, as the bearings rotate due, the O-rings may distribute the load uniformly. This will be discussed in more detail below in relation to the operation of the toothbrush 100.

By reducing rattling and providing a uniform load on each of the bearings 136, 138 the O-rings 140, 142 reduce audible noise that may be generated during operation of the toothbrush. Additionally, because the O-rings 140, 142 may deform against the chassis 118 and chassis cover 120, looser tolerances may be used to manufacture the chassis and chassis cover, which may decrease manufacturing costs. Moreover, the O-rings 140, 142, which may typically be formed of a deformable material, such as an elastomeric material, may provide a soft mount between the bearings 136, 138 and the chassis 118 and chassis cover 120. This soft mount may act as an isolator or dampening member and absorb vibrations of the output shaft 126.

The bumper assembly may be inserted around the output shaft 126. For example, both bumpers 148 may be received around the output shaft 126. In particular, the curved wall 266 may be dimensioned to fit around the outer diameter of the output shaft 126. The flanges 268a, 268b of the bumpers 148 may be aligned and engage each other. In some embodiments, the bumpers 148 may be connected together and completely surround the output shaft 126. The bumpers 148 may be fastened to the output shaft 126 in a variety of manners. In one embodiment, the dowel pin 182 may be received through the dowel aperture 244 defined in the output shaft 126 and its ends may be inserted into the channels 264 defined in each bumper 148. In this embodiment, the dowel pin 182 may be sufficiently long to extend through at least a portion of the thickness of the bumper 148 wall to retain the bumpers together. The walls surrounding and defining the channels 264 in the bumpers 148 may act to restrain lateral movement of the dowel pin 182. In some examples, the dowel pin 182 may be securely positioned within the output shaft and in other examples, the dowel pin may be removable positioned within the output shaft.

With reference to FIGS. 4 and 5, the tip shaft 134 may be inserted onto the output shaft 126. For example, at least a portion of the tip shaft 134 may be hollow or define a cavity and the output shaft 12 may be inserted into the defined cavity to connect the two shafts together.

With reference to FIGS. 5, 18, and 19B, the chassis 118 and chassis cover 120 may be received around a number of the linkage and drive components. The rocker 144, drive pin 174, bushing 176, ground coupler 132 and eccentric 128 may be received in the linkage cavity 286, 314 in the chassis 118 and chassis cover 120, respectively. In other words, the chassis 118 and chassis cover 120 may be connected together such that the two linkage cavities 286, 314 may form a single cavity. The linkage cavities 286, 314 may be configured to receive the components of the linkage, while still allowing the components to move as desired within the cavities. It should be noted that in some embodiments, the cover aperture 296 defined in the chassis cover 120 may allow the coupler 132 to move within the chassis and chassis cover. In other words, the aperture 296 may define a window through which portions of the coupler 132 can extend, if needed.

The output shaft 126 may be received into the shaft cavity 270, 302 and the ball bearings 136, 138 being received in the bearing cavities 280, 282, 304, 306, respectively. The output shaft 1236 may extend outwards from a top end of both the chassis and chassis cover. Additionally, the bumper assembly 148 including both bumpers may be received in the respective bumper cavities 284, 308 with the flange portions 268a, 268b of the bumpers 148 being positioned in the flange cavities 290, 312 and the curved wall 266 of the bumpers being positioned in the cylindrical portion 288, 310 of the bumper cavities 284, 308.

Once the linkage components are received in the respective cavities in the chassis 118, the chassis cover 120 may be positioned over the chassis 118 and fastened thereto. For example, the plurality of fastening apertures 272a, 272b, 272c, 272d on the chassis and the fastening apertures 294a, 294b, 294c, 294d may be aligned and fasteners may be received therein to connect the chassis and chassis cover together. Additionally, fasteners 190 may be received through fastening apertures 278 in the base 274 of the chassis 118 to connect the chassis 118 to the foundation plate 122.

In some embodiments, the chassis 118 and the chassis cover 120 may be plastic injection molded components. Although the plastic material may be less rigid than metal or metal alloys, the chassis and chassis cover may provide sufficient rigidity to the toothbrush. This is due to their connection to the foundation plate 122. As described above, the foundation plate 122 may be a substantially rigid material, such as stainless steel or other metallic materials. The position of the foundation plate 122 between a mounting face of the motor 114 and the chassis 118 imparts rigidity to the assembly. Additionally, because the chassis and chassis cover are mounted to the foundation plate 122, the rigidity of the foundation plate may provide additional strength and rigidity to the chassis and chassis cover. By using less expensive materials, such as plastics, for the chassis and chassis cover, manufacturing costs of the toothbrush may be reduced. For example, conventional electric toothbrushes may include a chassis formed of a metal material through a machine die casting process, which may require more expensive manufacturing processes than injection molding, as well as require more expensive materials (metals versus plastics).

With continued reference to FIGS. 5, 18, and 19B, the boot seal 146 may be received around the trip shaft 134 and the output shaft 126 (e.g., around the connection between the two shafts) and may connect to the chassis 118 and the chassis cover 120. In one embodiment, the lip 320 of the boot seal 146 may be inserted into the grooves 292, 300 on the chassis 118 and chassis cover 120. A seal ring 170 may be received into the annular groove 322 defined in the boot seal 146 and compress the boot seal 146 around the output shaft 126 to seal the boot seal against the output shaft. For example, the seal ring 170 may be a somewhat rigid material, such as brass. Additionally, the skirt 328 and seal 326 of the boot seal 146 may also press against the housing 106 to seal against the interior surface 396 of the housing 106.

When the drive assembly is received into the housing 106, the boot seal 146 may mount the nose of the chassis 118 and chassis cover 120 to the housing 106. For example, with reference to FIG. 5, the housing 106 may include two neck protrusions 410a, 410b that extend into the housing cavity 172 and the boot seal 146, and specifically, the seal 170 around the boot seal 146, may engage these two protrusions 410a, 410b. The seal ring 170 may squeeze against the neck of the boot seal 146 to help seal the boot seal 146 against the shaft.

With reference to FIGS. 4 and 5, the tip shaft 134 may be inserted into the retainer ring 168 of the brush head 102. The retainer ring 168 and the tip shaft 134 may be selectively releasable and the connection may include one or more selectively releasable fastening mechanisms, such as press fit, detents, or the like that may connect the brush tip 102 to the tip shaft 134.

With reference now to FIGS. 3A, 5, and 19A, the button circuit 340 and the button 110 may be connected to the front side of the chassis cover 120 and may be positioned on the chassis cover 120 above the cover aperture 296. Connection wires 334a, 334b may extend from the control circuit 154 to the button circuit 340 and may electrically couple the control circuit 154 with the button circuit 340. In this manner as the button 110 is selectively activated by a user, the control circuit 154 may receive signals indicating the desired operation or setting selected by a user.

In some embodiments, one or more components of the toothbrush may be formed through an overmolding or injection molding process. As an example, the housing 106 and handgrip 108 may be formed in a molding process that may connect the two components together. With reference to FIGS. 23-24B, in one embodiment, the housing and handgrip maybe formed through a two-shot molding process. For example, the material forming the housing 106 may be injected into a mold in a semi-liquid, molten, or otherwise viscous form. The material 102 may form around the mold, which may be defined with the desired features of the housing 106.

After the material for the housing 106 has been injected into the mold, the material for the handgrip 108 may be injected into the mold and around the housing 106. In some embodiments, the handgrip 108 material may be injected through a gate or other injection area. In these embodiments, the gate may be selected to along the button pad 442 and may be positioned so that when the button 110 is connected to the pad 442, the gate area (which may be rougher or aesthetically unpleasing as compared to other areas) may be hidden. By forming the handgrip 108 through the overmold process, the housing 106 may be sealed, reducing water and chemical seepage into the housing 106.

Additionally, in instances where a single injection location is used, the mold and/or the housing may include pathways to direct the material for the handgrip 108 to the desired areas. For example, the bridge 448 may allow the material to flow into from the injection site to form both grip portions 450a, 450b and upper pads 444a, 444b. With reference to FIG. 23, the material for the handgrip 102 may flow over the bridge 448 and exit the interior of the housing 106 through the port 436 and flow into the handgrip indentation 430. As the material reaches the bottom port 432 it may enter back into the interior of the housing 106 and form the vibration pads 438a, 438b and flow out the bumper aperture 434 forming the bumper 446. In this manner, the vibration pads 434a, 438a, 444a, 444b may be formed integrally with the hand grip 108 and the housing 106.

Once formed, the vibrations pads 438a, 438b, 444a, 444b may act to absorb vibrations from the drive assembly and power assembly, reducing or preventing vibrations from being transferred to the housing 106 where they may be felt by a user.

Operation of the Toothbrush

The operation of the toothbrush 100 will now be discussed in more detail. With reference to FIGS. 1A, 3A and 3B, to activate the toothbrush 100, the user may press on the button 110. The button 110 may be pushed towards the button circuit 340, causing contacts on the button to connect with contacts on the button circuit 340. Once the button 110 has contacted the button circuit 340, the button circuit may transmit a signal through the communication wires 334a, 334b to the control circuit 154 and the control chip 342. The control chip 342 may activate one or more of the lights 352a, 352b, 352c indicating the setting or operational mode of the toothbrush (e.g., fast, medium, slow, low battery, etc.).

With reference to FIGS. 5-7, the control chip 342 may also provide power to the motor 114 from the battery 152. For example, the control chip 342 may transmit power from the battery 152 through the power wires 336a, 336b to the terminals 194a, 194b of the motor 114. As the motor 114 receives power, it begins to rotate the drive shaft 124. The eccentric 128 connected to the drive shaft 124 thus also begins to rotate. In some embodiments, the eccentric 128 may rotate at a speed between 13000 to 17000 RPM, and often at 15000 RPM.

The inner wall of the linkage bearing 130 rotates with the eccentric 128 and the race of the bearing 130 is securely received within the aperture in the first end of the link coupler 132, imparting motion to the link coupler 132. The linkage ball bearing 130 may reduce friction at the connection between the eccentric 128 and the coupler 132, which reduces resistance, and results in reduced current consumption for the motor. In other words, the bearing 130 may help to reduce the load experienced by the by motor 114, which may increase the efficiency of the motor 114. Additionally, the reduction in friction may reduce the audible noise produced at the joint.

With continued reference to FIGS. 5-7, the second end of the link coupler 132 is connected to the drive pin 174 through the bushing 176. The rotational movement of the eccentric 128 may be translated as primarily linear movement of the second end of the link coupler 132 and thereby to the rocker 144 by the connection between the link coupler 132 and both the eccentric 128 on the output shaft 126 and the drive pin 174. The rotational movement of the eccentric 128 on the drive shaft 124 thus pushes and pulls the second end of the link coupler 132. The bushing 176 may allow some slippage between the drive pin 174 and the second end of the link coupler 132, while the opposite end of the drive pin 174 is fixed to the rocker 144, further limiting the range of motion imparted to the drive pin 174 as primarily translational.

As noted, the output shaft 126 is fixedly engaged to the rocker 144, which, as discussed above, may be molded around both the output shaft 126 and the drive pin 174. Accordingly, as the drive pin 174 is moved by the link coupler 132, the first end of the rocker 144 moves in an arc while the second end of the rocker 144 attached to the output shaft 126 pivots on the longitudinal axis of the output shaft 126. The movement of the output shaft 126 may be constrained by the ball bearings 136, 138, as they are mounted closely within the chassis 118 and chassis cover 120. For example, the chassis 118 and chassis 120 cover may be tightly connected around the bearings 136, 138, which are mounted about the output shaft 126. This arrangement constricts the movement of the output shaft 126, which is restrained to rotate within the bearings 136, 138. The drive pin 174 may slip slightly within the bushing 176 due to the constraints imposed by the rocker 144. The output shaft 126 thus rotates or pivots back and forth about its longitudinal axis.

Figure 1E:
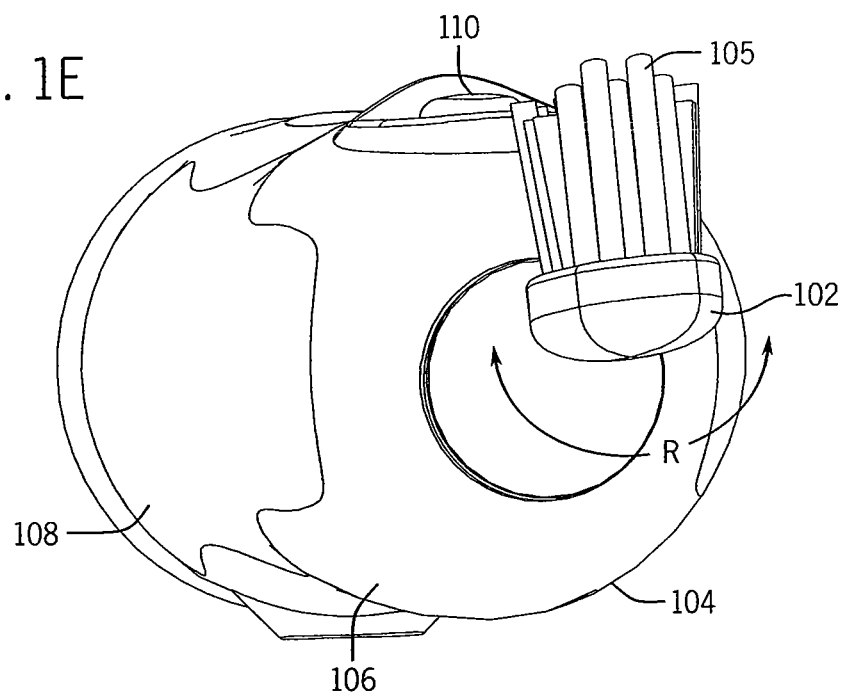
FIG. 1E is a top perspective view of the toothbrush.

The output shaft 126 moves the tip shaft 134, which in turn moves the brush head 102 in a rotational movement of arc R shown in FIG. 1E. In some embodiments, the brush head 102 may move in a semicircular pathway, as shown by the rotation arc R. This causes the bristles 105 to move side to side, which may be useful for the removal of debris and plaque from a user's teeth.

In some embodiments, the user may press the button 110 to vary the speed of the motor and thus oscillation speed of the bristles 105. In this example, the user may press the button 110 once to activate the toothbrush and a second time to change the speed of the motor 114. As described above, once the button 110 has been selected, one or more of the lights 352, 352b, 35c may be illuminated (either pulsing or constant) or may change color. Additionally, the control chip 342 may then vary the power level received by the motor 114, which may reduce the rotational speed of the drive shaft 124, reducing the speed of rotation of the bristles 105.

With reference to FIGS. 4 and 5, as the output shaft 126 pivots, the elastomeric bumpers 148 may act to conserve energy in the system. As described above, the dowel pin 182 is received through the output shaft 126 and extends from opposing sides of the output shaft 126 within symmetric opposing spaces between the two bumpers 148. As the output shaft 126 pivotably reciprocates, opposing ends of the dowel pin 182 contact opposite edges of respective bumpers 148. The contact between the dowel pin 182 and the bumpers 148 due to reciprocation of the output shaft 126 may occur simultaneously and in opposite directions. This impact imparts a torque on the shaft 126 in an opposite direction to the present pivot direction of the output shaft at the end of the travel in that direction of the cycle. The bumpers 148 (through the dowel pin 182) thereby act to conserve some of the kinetic energy of the output shaft and reapply the energy in the opposite direction. This energy conservation reduces stresses on the linkage assembly, thereby reducing wear and tear on the components, as well as audible noise generated during movement. Moreover, the load on the motor 114 may be reduced because the bumpers 148 conserve energy at one end of the rotation arc R and apply it to the shaft as it changes to head towards the other end of the rotation arc R.

As described above, the output shaft 126 is also connected to ball bearings 136, 138 and each of the ball bearings 136, 138 includes an O-ring 140, 142 surrounding and outer perimeter. As the output shaft 126 rotates, the O-rings provide a soft mounting to the chassis 118 and chassis cover 120 to further absorb vibrations due to the movement of the output shaft 126.

Selectively Varying Motor Output

In some embodiments, the motor may be selectively varied, based on a user input or another parameter, such as battery life, to vary the movement of the brush head. For example, when the battery begins to run low on power, a control signal may be applied to the motor that may increase the amount of power applied to the motor so that even as the voltage output of the battery drops, the output of the motor may be substantially constant. As another example, a user may provide an input indicating a slower or faster bristle speed and a control signal may be applied to the motor to selectively increase or decrease the bristle speed.

A motor control module for maintaining and changing the output of the motor will now be discussed in more detail. In some embodiments, the motor control module may include the control chip 342 or other processing element and may be connected to or mounted on the control circuit 154. For example, in some embodiments, the motor control circuit may be a component included within the control circuit or its functions may be executed by one or more components of the control circuit 154 or button circuit 340.

Figure 25:
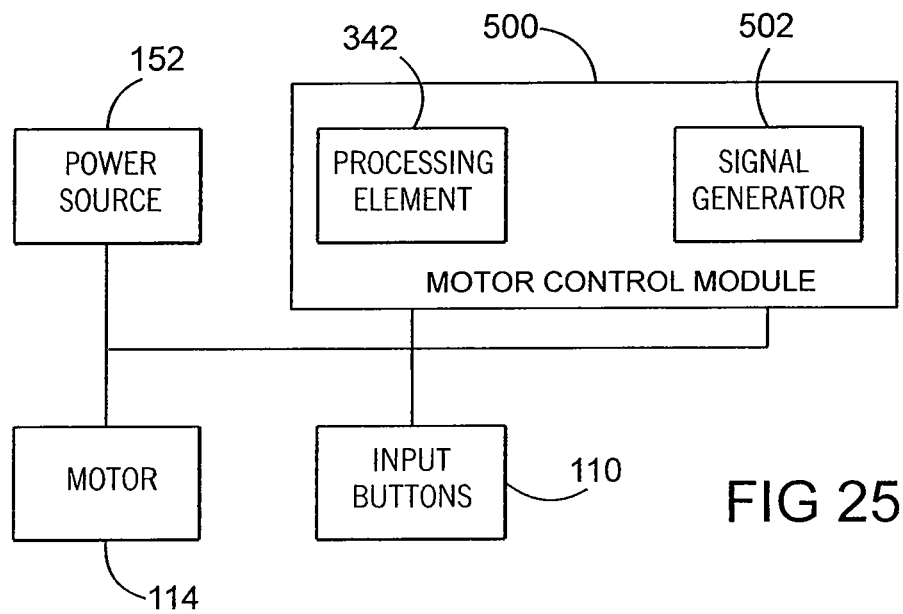
FIG. 25 is a simplified block diagram of the toothbrush including a motor control circuit.

FIG. 25 is a simplified block diagram of the toothbrush illustrating the electrical communication between select components. With reference to FIGS. 3A and 25, the power source 152 or batteries may be in communication with the motor control module 500, the motor 114, and optionally, the input button 110.

In some examples, the control circuit 154 may provide a substrate that supports one or more components, as well as provides communication between those components. For example, the control circuit 154 may be a printed circuit board including one or more traces or connective lines that transmit signals between the control module 500, the motor 114 and the batteries 152.

The control module 500 may selectively control the motor 114 to vary (or maintain) one or more output parameters of the toothbrush 100. The motor control module 500 may include a signal generator 502 as well as one or more processing elements, such as the control chip 342. The control chip 342, as discussed above, may be one or more processors or control chips that may process and execute instructions.

The signal generator 502 may be substantially any type of component that may create voltage signals to control one or more characteristics of the motor 114. For example, the signal generator 502 may create one or more repeating or non-repeating electronic signals (e.g., voltage waveforms) that may be applied to the motor 114. In a particular implementation, the signal generator 502 may be a function generator that may produce electrical waveforms over a range of frequencies. Exemplary waveforms include sinusoidal waves, square waves, sawtooth waves, triangular waves, and so on. Additionally, the signal generator may be configured to create modified waves that include characteristics of two or more waveforms. Illustrative waveforms that may be used will be discussed in more detail below with respect to FIGS. 27A and 27B.

Figure 26:
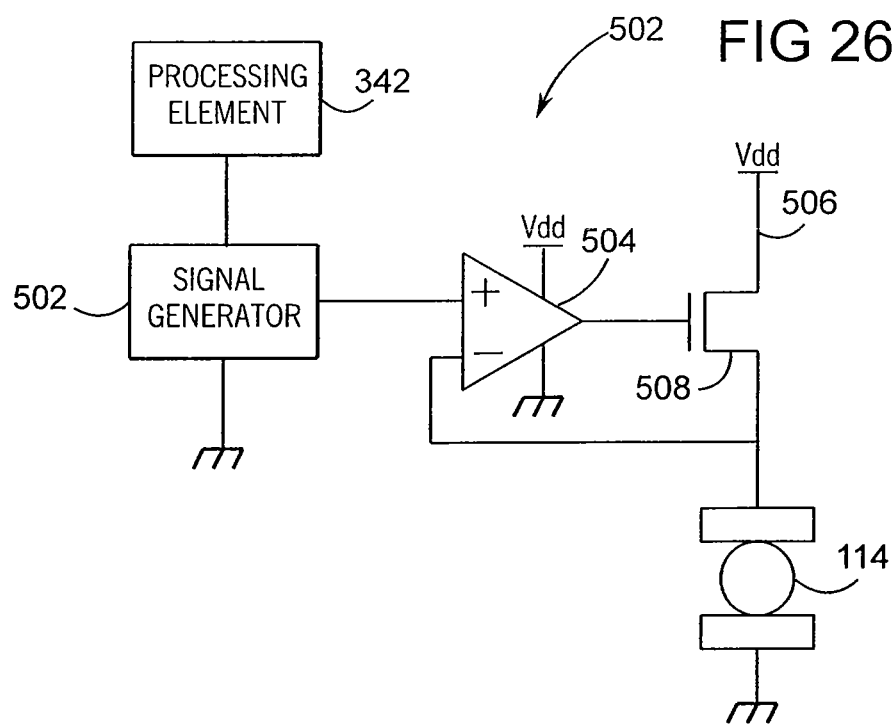
FIG. 26 is a simplified circuit schematic of block diagram of FIG. 25.

FIG. 26C is a simplified circuit diagram of the motor control module 500. With reference to FIGS. 25 and 26, the signal generator 502 may be in communication with an amplifier 504 and a gate 508 or switch. The signal generator 502 may be in communication with the control chip 342, which may determine the signals generated by the signal generator 502, which may then be applied to the motor. In some embodiments, the control signals generated by the signal generator 502 may be applied to the motor though pulse width modulation. That is, the voltage and current may be alternatively switched on and off rapidly to achieve an average input that replicates the control signal.

The signal generator 502 may be in communication with the amplifier 504, which may amplify a signal generated by the signal generator 502 prior to applying the signal to the motor 114. For example, the amplifier 504 may be an operational amplifier or a differential amplifier. The amplifier 504 may be in communication with the motor 114 as well as the signal generator 502. In some examples, the amplifier 504 may be configured to receive feedback from its output, in order to provide a more consistent output signal. However, it should be noted that the configuration of the amplifier 504, as well as the type of amplifier and inputs used may be varied based on the type of motor 114 and signal generator 502 used.

The amplifier 504 may be in communication with a gate 508 or switch. The gate 508 may selectively provide the output of the amplifier 504 (which may be a signal produced by the signal generator 502) to the motor 114. For example, when the gate is not activated, the motor 114 may not receive a signal from the signal generator, but may receive a constant power signal. As another example, when the gate is not activated, the motor 114 may be separated from any signal or power source, preventing the motor from being activated. In other embodiments, the amplifier may be omitted.

The gate 508 may be a switch or other selectively activated component. In one example, the gate 508 may be a transistor, such as a metal-oxide-semiconductor field-effect transistor (MOSFET), such as an N-channel MOSFET. However, other types of transistors or gates are also envisioned, as well as other components that may be used to selectively provide communication between two or more components.

The signal generator 502 may selectively modify a control signal applied to the motor to vary the motor output. In one example, the signal generator 502 may apply a varying signal to the motor 114, which may cause the motor 114 to selectively vary one or more movement characteristics. For example, the signal generator 502 may apply a signal that has a variable voltage across a predetermined time. The signal may vary not only in voltage magnitude, but also in time between a high voltage and a low voltage (e.g., frequency). In other words, the control signal may be a set duty cycle which may determine the 'on' time or high voltage applied to the motor during a particular interval or period of time.

With reference to FIG. 26, the amplifier 504 may increase the signal generated by the signal generator 502 and provide the increased control signal to the motor 114. The control signal may selectively interrupt or vary the power supplied to the motor 114, causing the motor to intermittently stop or slow down, reducing, stopping, or changing the movement of the drive shaft 124. As the drive shaft 124 varies, the movement of the output shaft 126, and thus the brush head 102 of the toothbrush 100 may vary. For example, as more power is applied to the motor, the motor may increase the RPMs of the drive shaft, increasing the speed or frequency of the bristle movement.

The signal generator 502 may vary a frequency and magnitude of the control signal based on a desired output frequency of the bristles 105. FIGS. 27A and 27B illustrate examples of control signals that may be created by the signal generator to be applied to the motor 114. With reference to FIG. 27A, a control signal 530 may be a square wave having a voltage peak 532 or amplitude and a voltage minimum 534. In some examples, the voltage peak 532 (i.e., maximum voltage) may be applied for a duration T1 and the voltage minimum 204 may be applied for a duration T2. The durations T1 and T2 may be approximately equal or may be varied from each other. Additionally, the peak and minimum voltages may be set as desired, and in some instances the minimum voltage may be approximately 0V. The time durations T1 and T2, as well as the peak voltage 532 and minimum voltage 534 may be determined based on a desired duty cycle of the control signal 530, as well as a desired output of the motor, or other factors.

In the control signal 500 illustrated in FIG. 27A, there may be a rapid transition between the maximum or peak voltage and the minimum voltage. For example, the control signal 530 may be a square wave that substantially instantaneously transitions between minimum and maximum values. However, in other examples, the control signal may gradually transition between a maximum and minimum voltage.

With reference to FIG. 27B, a control signal 540 having a sinusoidal shape is illustrated. The control signal 540 may have a peak voltage 542 and a minimum voltage 544, with the peak voltage 542 having a duration T3 and the minimum voltage having a duration T4. However, because the control signal 540 may gradually change between the maximum and minimum levels, the durations T3 and T4 may represent the time between inflection points 546, 548. The inflection points 546, 548 generally may represent half of a cycle or period for the control signal 540. In other words, the sum of the durations T3 and T5 may represent the period for the control signal 540.

In some embodiments, the motor control module 500 may monitor the charge level of the battery 152 to determine whether the control signal provided to the motor 114 may need to be varied. In other embodiments, the motor control module 500 may monitor the output of the motor through one or more sensors. In these embodiments, a feedback loop may be used to maintain a desired motor speed or output and/or to vary the motor output to a desired setting. Additionally, in some implementations, a characterization curve or other reference may be created that may indicate a desired control signal based on the desired motor speed and/or charge level. In these implementations, the motor control module may reference the characterization curve to determine the desired control signal for the motor.

Figure 28:
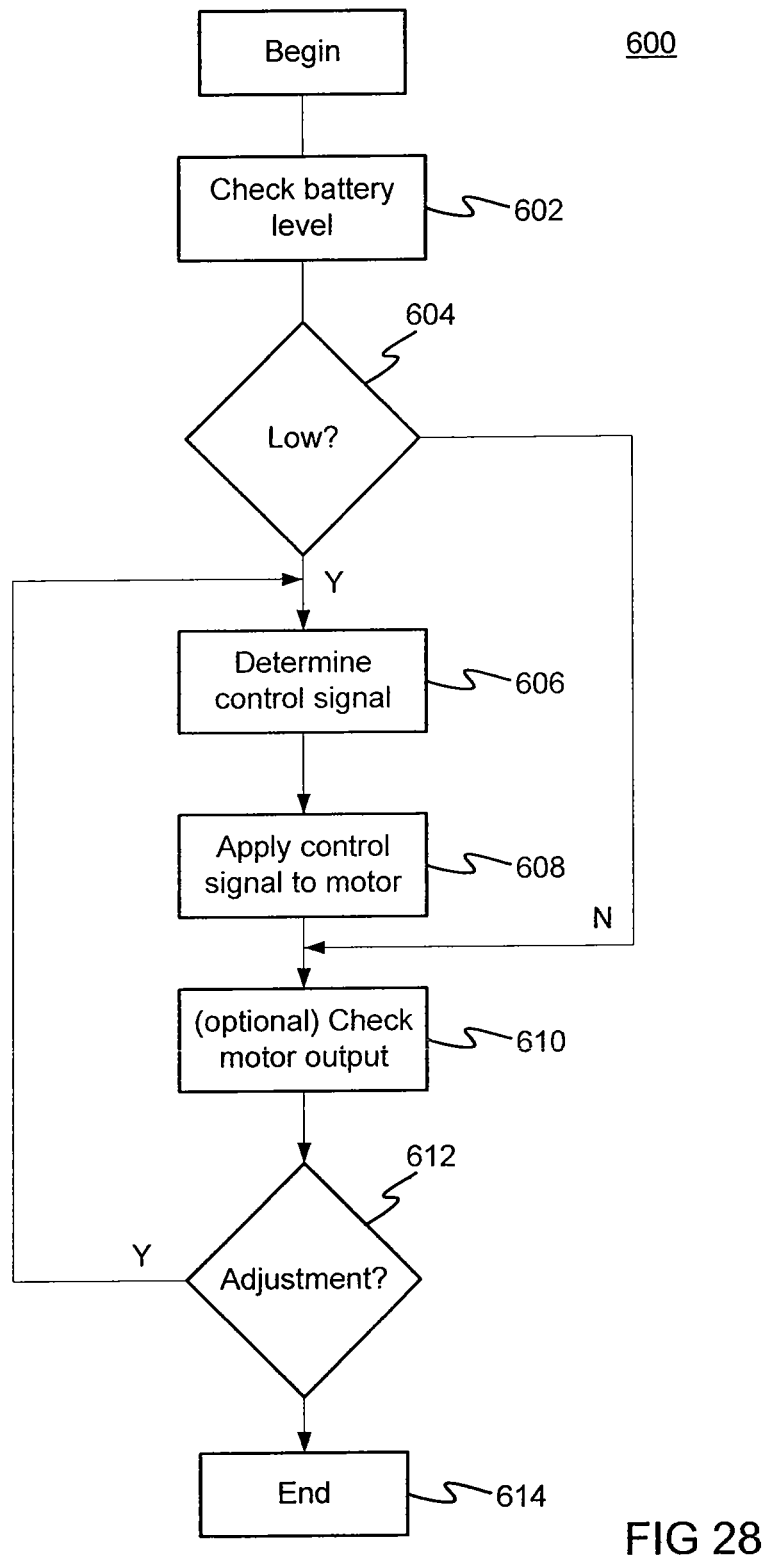
FIG. 28 is a flow chart illustrating a method for maintaining a substantially constant movement output for the toothbrush.

A method for using the motor control module 500 to vary the output of the motor 114 will now be discussed. FIG. 28 is a flow chart illustrating an example method of controlling the output of the motor. The method 600 may begin with operation 602 the battery level (e.g., charge level) may be checked. For example, the control chip 340 may pull power from the battery 152 and determine whether the output voltage is below a predetermined threshold. The method 600 may then proceed to operation 604 and the control chip 340 may determine whether the battery level is below a predetermined threshold. As the battery reduces in charge, the output voltage may also decrease and if the battery level decreases past a predetermined threshold, the output voltage may affect the output of the motor 114 that is powered by the battery 152. This is because, the control chip may believe a certain power level is being applied to the battery, when in fact the power level may be below the desired level, which may reduce the speed of the motor.

In operation 604 if the battery charge is low (or otherwise below the predetermined threshold), the method 600 may proceed to operation 606. In operation 606, the control circuit 340 may determine a desired control signal 530, 540. The control signal may be selected based on a desired duty cycle that may be applied to the motor, e.g., the magnitude and duration of a voltage applied to the motor. For example, the control signal may be selected to maintain a constant frequency or speed of the drive shaft 124 as compared with a high or fully charged battery state. Continuing with these examples, a control signal with an increased duty cycle as compared to normal mode may be selected, which may pull extra charge from the battery (which in its reduced state may equal the normal power level typically applied). In these examples, the control signal may be selected to pull additional power from the battery to provide the required voltage to the motor.

After operation 606, the method 600 may proceed to operation 608 and the control signal may be applied to the motor 114. For example, the signal generator 502 may create the control signal and apply power to the motor 114 (from the battery) based on the control signal. As the motor receives the control signal, the motor 114 may begin to rotate the drive shaft 124 accordingly, which as described above, rotates/vibrates the bristles 105.

After operation 608 or if in operation 604, the battery level was not below the predetermined threshold, the method 600 may proceed to optional operation 610. In operation 610, the control chip 342 may receive feedback from the motor output. For example, the toothbrush may include one or more output sensors (not shown) that may monitor the output speed of the drive shaft 124 or other characteristics of the motor to determine the motor output. The motor output may be used as feedback to determine if the motor needs further adjustment.

After operation 610, the method 600 may proceed to optional operation 612. In operation 612, the control chip 340 may determine whether the motor output may need adjustment. For example, the control chip 340 may analyze the RPM of the drive shaft 124 to determine if the control signal should be increased, decreased, or the like, in order to produce the desired output speed. In operation 612, if the motor 114 does need adjustment the method 600 may return to operation 606 and a new or adjusted control signal may be determined to adjust the output of the motor. However, if in operation 612 the motor does not need to be adjusted, the method 600 may proceed to end state 614.

Figure 29:
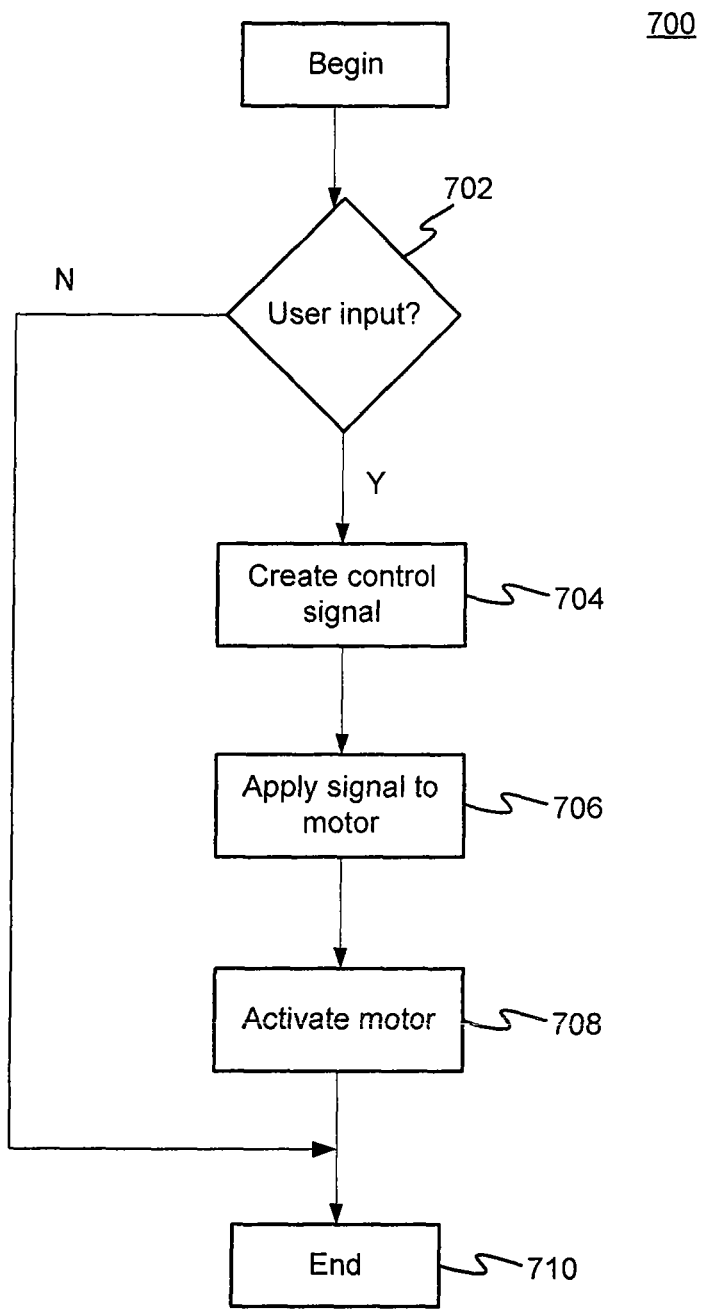
FIG. 29 is a flow charge for selectively varying the movement output of the toothbrush.

In some embodiments, the motor control module 500 may be used to modify the motor speed based on a user input. For example, certain users may prefer faster or slower bristle movement speeds. FIG. 29 is a flow chart illustrating a method for varying one or more output characteristics of the motor based on a user input. The method 700 may begin with operation 702 and the control chip 342 may determine if a user input has been received. For example, the control chip 342 may determine if the button 110 has activated the button circuit or if another input button has been activated.

If a user input has been received, the method 700 may proceed to operation 704. In operation 704 the control chip 342 may create or determine a control signal to be applied. The control signal may be determined based on the user input. For example, if the user input is to increase the bristle 105 speed, the duty cycle of the input signal may be increased as compared to if the user input is to reduce the bristle speed, in which case the duty cycle for the control signal may be reduced.

After operation 704, the method 700 may proceed to operation 706. In operation 706, the signal generator 502 may apply the control signal to the motor 114. For example, the signal may be amplified by the amplifier 504 and then the gate 508 may be activated, providing the signal to the motor 114. As the motor receives the control signal, the method 700 may proceed to operation 708. In operation 708 the motor 114 may be activated, rotating the drive shaft 124 and causing the bristles 105 to move at the desired speed or frequency. After operation 708, the method 700 may proceed to an end state 710 and terminate.

The methods 600 and 700, as well as the motor control module 500 may allow one or more output characteristics of the motor 114 to be selectively varied. In some embodiments, the input signal of the motor from the battery may be varied such that the output speed of the motor may remain constant, even as the battery charge is drained. In these examples, there may not be a decrease in performance for the toothbrush, even at very low battery charge levels. In other examples, the movement speed or frequency of the bristles may be varied by a user, which may allow a user to select a desired speed to enhance the user experience with the toothbrush.

Conclusion

The foregoing description has broad application. For example, while examples disclosed herein may focus on toothbrush, it should be appreciated that the concepts disclosed herein may equally apply to other types of motor powered devices where vibration isolation and noise reduction may be desired. Similarly, although the toothbrush is discussed with respect to a single speed motor, the devices and techniques disclosed herein are equally applicable to other types of drive mechanisms. Accordingly, the discussion of any embodiment is meant only to be exemplary and is not intended to suggest that the scope of the disclosure, including the claims, is limited to these examples.

The housing, chassis, chassis cover, and other elements of the various examples of the toothbrush assembly may be integrally formed or may be made of two or more separate components that are joined together by mechanical fasteners, sonic or heat welds, adhesives, chemical bonds, any other suitable method, or any combination thereof.

All directional references (e.g., upper, lower, upward, downward, left, right, leftward, rightward, top, bottom, above, below, vertical, horizontal, clockwise, and counterclockwise) are only used for identification purposes to aid the reader's understanding of the examples of the invention, and do not create limitations, particularly as to the position, orientation, or use of the invention unless specifically set forth in the claims. Joinder references (e.g., attached, coupled, connected, joined and the like) are to be construed broadly and may include intermediate members between the connection of elements and relative movement between elements. As such, joinder references do not necessarily infer that two elements are directly connected and in fixed relation to each other.

What is claimed is:

1. An electrically driven toothbrush comprising
a handle housing;
a brush head releasably connected to the handle housing and including a plurality of bristles;
an output shaft connected to the brush head;
a motor coupled to the output shaft via a linkage assembly, wherein a motor rotates the output shaft to pivot the brush head in a first direction and a second direction along the rotation arc;
a first deformable member connected to a first side of the output shaft; and
a second deformable member connected to a second side of the output shaft, wherein
the first deformable member absorbs kinetic energy from the output shaft only at an end of the first direction of the rotation arc and imparts stored kinetic energy to the output shaft only at a beginning of the second direction of the rotation arc; and
the second deformable member imparts stored kinetic energy to the output shaft only at a beginning of the first direction of the rotation arc and absorbs kinetic energy from output shaft only at an end of the second direction of the rotation arc.

2. The electrically driven toothbrush of claim 1, further comprising a connecting member coupled to the first deformable member and the second deformable member, wherein the connecting member connects the first deformable member and the second deformable member to the output shaft.

3. The electrically driven toothbrush of claim 1, wherein the linkage assembly comprises
a link coupler operably coupled to a drive shaft of the motor;
a drive pin connected to the link coupler; and
a rocker connected to the drive pin and the output shaft.

4. The electrically driven toothbrush of claim 1, further comprising a boot seal positioned around the output shaft and against an interior surface of the handle housing.

5. The electrically driven toothbrush of claim 1, further comprising one or more bearings received around the output shaft.

6. The electrically driven toothbrush of claim 1, wherein
the first deformable member imparts the stored kinetic energy to the output shaft at the beginning of the second direction to assist the motor in rotating the output shaft in the second direction; and
the second deformable member imparts the stored kinetic energy to the output shaft at the beginning of the first direction to assist the motor in rotating the output shaft in the first direction.

* * * * *